(12) United States Patent
Luisi et al.

(10) Patent No.: US 8,674,108 B2
(45) Date of Patent: Mar. 18, 2014

(54) SOLID FORMS OF N-[2,4-BIS(1,1-DIMETHYLETHY)-5-HYDROXYPHENYL]-1,4-DIHYDRO-4-OXOQUINOLINE-3-CARBOXAMIDE

(75) Inventors: Brian Luisi, Mansfield, MA (US); Sneha Ghanshyam Arekar, Brighton, MA (US); Adriana Costache, Cambridge, MA (US); Kirk Raymond Dinehart, Holliston, MA (US); Steven C. Johnston, Litchfield, NH (US); Bobbianna J. Neubert-Langille, Sudbury, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/452,758

(22) Filed: Apr. 20, 2012

(65) Prior Publication Data

US 2013/0281487 A1 Oct. 24, 2013

(51) Int. Cl.
*C07D 215/38* (2006.01)
(52) U.S. Cl.
USPC .......................................... 546/159; 514/312
(58) Field of Classification Search
USPC .......................................... 546/159; 514/312
See application file for complete search history.

(56) References Cited

U.S. PATENT DOCUMENTS

| | | | |
|---|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Hadida Ruah et al. |
| 8,124,781 B2 | 2/2012 | Siesel |
| 8,163,772 B2 | 4/2012 | Demattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Hadida Ruah et al. |
| 2005/0059687 A1 | 3/2005 | Makings et al. |
| 2005/0113423 A1 | 5/2005 | Van Goor et al. |
| 2006/0052358 A1 | 3/2006 | Hadida Ruah et al. |
| 2007/0105833 A1 | 5/2007 | Hadida Ruah et al. |
| 2007/0238775 A1 | 10/2007 | Hadida Ruah et al. |
| 2008/0071095 A1 | 3/2008 | Hadida Ruah et al. |
| 2008/0306062 A1 | 12/2008 | Hadida Ruah et al. |
| 2009/0105272 A1 | 4/2009 | Grootenhuis et al. |
| 2009/0143381 A1 | 6/2009 | Hadida Ruah et al. |
| 2009/0170905 A1 | 7/2009 | Keshavarz-Shokri et al. |
| 2009/0176839 A1 | 7/2009 | Keshavarz-Shokri et al. |
| 2009/0221597 A1 | 9/2009 | Hadida Ruah et al. |
| 2009/0246820 A1 | 10/2009 | Singh et al. |
| 2009/0253736 A1 | 10/2009 | Hadida-Ruah et al. |
| 2009/0298876 A1 | 12/2009 | Hadida Ruah et al. |
| 2010/0036130 A1 | 2/2010 | Siesel |
| 2010/0074949 A1 | 3/2010 | Rowe et al. |
| 2010/0087490 A1 | 4/2010 | Young |
| 2010/0113508 A1 | 5/2010 | Binch et al. |
| 2010/0113509 A1 | 5/2010 | Binch et al. |
| 2010/0113555 A1 | 5/2010 | Hadida Ruah et al. |
| 2010/0125090 A1 | 5/2010 | Hadida Ruah et al. |
| 2010/0130547 A1 | 5/2010 | Zhang et al. |
| 2010/0144798 A1 | 6/2010 | Van Goor et al. |
| 2010/0168094 A1 | 7/2010 | Binch et al. |
| 2010/0168158 A1 | 7/2010 | Binch et al. |
| 2010/0184739 A1 | 7/2010 | Sheth et al. |
| 2010/0249113 A1 | 9/2010 | Hadida Ruah et al. |
| 2010/0249180 A1 | 9/2010 | Gallardo-Godoy |
| 2010/0256184 A1 | 10/2010 | Rowe et al. |
| 2010/0267768 A1 | 10/2010 | Demattei et al. |
| 2010/0331344 A1 | 12/2010 | Hadida Ruah et al. |
| 2011/0008259 A1 | 1/2011 | Binch et al. |
| 2011/0060024 A1 | 3/2011 | Hadida Ruah et al. |
| 2011/0064811 A1 | 3/2011 | Hurter et al. |
| 2011/0065928 A1 | 3/2011 | Ambhaikar et al. |
| 2011/0071206 A1 | 3/2011 | Hadida Ruah et al. |
| 2011/0098311 A1 | 4/2011 | Van Goor et al. |
| 2011/0123449 A1 | 5/2011 | Zhang et al. |
| 2011/0124869 A1 | 5/2011 | Ambhaikar et al. |
| 2011/0172229 A1 | 7/2011 | Hadida Ruah et al. |

(Continued)

FOREIGN PATENT DOCUMENTS

| | | | |
|---|---|---|---|
| WO | 2007/079139 | * | 7/2007 |
| WO | 2007079139 A2 | | 7/2007 |
| WO | 2009038683 A2 | | 3/2009 |
| WO | 2011116397 A1 | | 9/2011 |

OTHER PUBLICATIONS

International Search Report for PCT/US2012/034578, dated Mar. 21, 2013, 6 pages.

*Primary Examiner* — D M Seaman
(74) *Attorney, Agent, or Firm* — Honigman Miller Schwartz and Cohn LLP; Christopher C. Forbes; Jonathan P. O'Brien

(57) ABSTRACT

The present invention relates to crystalline solvate forms of N-[2,4-bis(1,1-dimethylethyl)-5-hydroxyphenyl]-1,4-dihydro-4-oxoquinoline-3-carboxamide (Compound 1) and methods for their preparation. The present invention further relates to pharmaceutical compositions comprising the crystalline solvate forms, as well as methods of treatment therewith.

28 Claims, 39 Drawing Sheets

(56) References Cited

U.S. PATENT DOCUMENTS

| | | |
|---|---|---|
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Van Goor et al. |
| 2011/0263654 A1 | 10/2011 | Keshavarz-Shokri et al. |
| 2011/0288121 A1 | 11/2011 | Sun et al. |
| 2011/0288122 A1 | 11/2011 | Van Goor et al. |
| 2011/0306637 A1 | 12/2011 | Hadida Ruah et al. |
| 2011/0312958 A1 | 12/2011 | Hadida Ruah et al. |
| 2012/0004216 A1 | 1/2012 | Hadida Ruah et al. |
| 2012/0010257 A1 | 1/2012 | Hadida Ruah et al. |
| 2012/0015999 A1 | 1/2012 | Alargova et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | Demattei et al. |
| 2012/0122922 A1 | 5/2012 | Young et al. |
| 2012/0165372 A1 | 6/2012 | Demattei et al. |
| 2012/0184583 A1 | 7/2012 | Van Goor et al. |
| 2012/0190856 A1 | 7/2012 | Siesel |
| 2012/0203006 A1 | 8/2012 | Siesel |
| 2012/0208841 A1 | 8/2012 | Binch et al. |

* cited by examiner

TGA

TGA

US 8,674,108 B2

SOLID FORMS OF N-[2,4-BIS(1,1-DIMETHYLETHY)-5-HYDROXYPHENYL]-1,4-DIHYDRO-4-OXOQUINOLINE-3-CARBOXAMIDE

TECHNICAL FIELD OF THE INVENTION

The present invention relates to solid state forms, for example, crystalline solvate forms of N-[2,4-bis(1,1-dimethylethyl)-5-hydroxyphenyl]-1,4-dihydro-4-oxoquinoline-3-carboxamide (Compound 1), which is a modulator of cystic fibrosis transmembrane conductance regulator ("CFTR"). The invention also relates to pharmaceutical compositions including crystalline forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide, and methods therewith.

BACKGROUND OF THE INVENTION

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF. Potentiators of this type are disclosed in WO 2006/002421, which is herein incorporated by reference in its entirety. Another potential therapeutic strategy involves small molecule drugs known as CF correctors that increase the number and function of CFTR channels. Correctors of this type are disclosed in WO 2005/075435, which are herein incorporated by reference in their entirety.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$-$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$-$K^+$-ATPase pump and $Cl^-$ ion channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

N-[2,4-bis(1,1-dimethylethyl)-5-hydroxyphenyl]-1,4-dihydro-4-oxoquinoline-3-carboxamide (Compound 1) is a potent and selective CFTR potentiator of wild-type and mutant (including e.g., ΔF508, R117H, and G551D) forms of human CFTR. N-[2,4-bis(1,1-dimethylethyl)-5-hydroxyphenyl]-1,4-dihydro-4-oxoquinoline-3-carboxamide is useful for treatment of adult patients with cystic fibrosis and at least one G551D-CFTR allele.

Accordingly, there is a need for stable bioavailable pharmaceutical compositions of N-[2,4-bis(1,1-dimethylethyl)-5-hydroxyphenyl]-1,4-dihydro-4-oxoquinoline-3-carboxamide useful for treating patients suffering from CF and methods of administering the same.

SUMMARY OF THE INVENTION

Solid forms of N-[2,4-bis(1,1-dimethylethyl)-5-hydroxyphenyl]-1,4-dihydro-4-oxoquinoline-3-carboxamide (Compound 1), which are crystalline solvates are described herein.

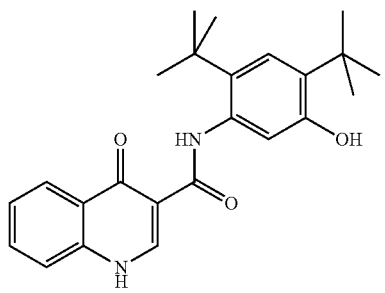

The crystalline solvates forms of Compound 1 (or "crystalline solvates"), disclosed herein are designated as Forms D, E, F, G, H, I, J, K, L, M, N, O, P, Q, R, S, T, W, or Hydrate B, respectively.

The present invention is also directed to processes for making crystalline solvates of compound 1 designated as Forms D, E, F, G, H, I, J, K, L, M, N, O, P, Q, R, S, T, W, or Hydrate B, respectively.

The present invention is further directed to pharmaceutical compositions comprising a crystalline solvate of Compound 1 selected from Forms D, E, F, G, H, I, J, K, L, M, N, O, P, Q, R, S, T, W, or Hydrate B, respectively, and a pharmaceutically acceptable carrier or excipient.

The invention is further directed to therapeutic methods for treating CFTR-mediated diseases such as cystic fibrosis.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cfte, for CFTR mutations).

The term "modulating" as used herein means increasing or decreasing by a measurable amount.

The term "treatment", as used herein, unless otherwise indicated, means the treatment or prevention of a CFTR related disorder as provided in the methods described herein, including curing, reducing the symptoms of or slowing the progress of said disorder. The terms "treat" and "treating" are defined in accord the foregoing term "treatment". The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function. The term "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

"Solvate" as in the phrase "crystalline solvate" is a crystalline solid containing either stoichiometric or nonstoichiometric amounts of a solvent incorporated within the crystal structure. For example, if the incorporated solvent is water, the solvates are also commonly known as hydrates.

Crystalline Solvate Forms

The present invention is directed to crystalline solvates of N-[2,4-bis(1,1-dimethylethyl)-5-hydroxyphenyl]-1,4-dihydro-4-oxoquinoline-3-carboxamide (Compound 1) having the structural formula:

Compound 1

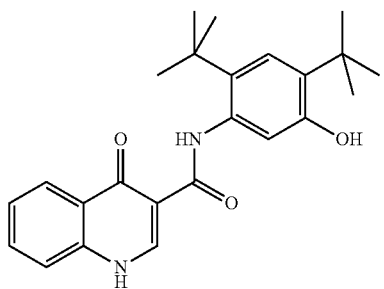 [SMILES: CC(C)(C)c1cc(C(C)(C)C)c(NC(=O)c2c[nH]c3ccccc3c2=O)cc1O]

In one aspect, the invention includes a crystalline solvate of Compound 1, wherein the crystalline solvate is designated as a solid form selected from the group consisting of Form D, Form E, Form F, Form G, Form H, Form I, Form J, Form K, Form L, Form M, Form N, Form O, Form P, Form Q, Form R, Form S, Form T, Form W, and Hydrate B.

Figure 2:
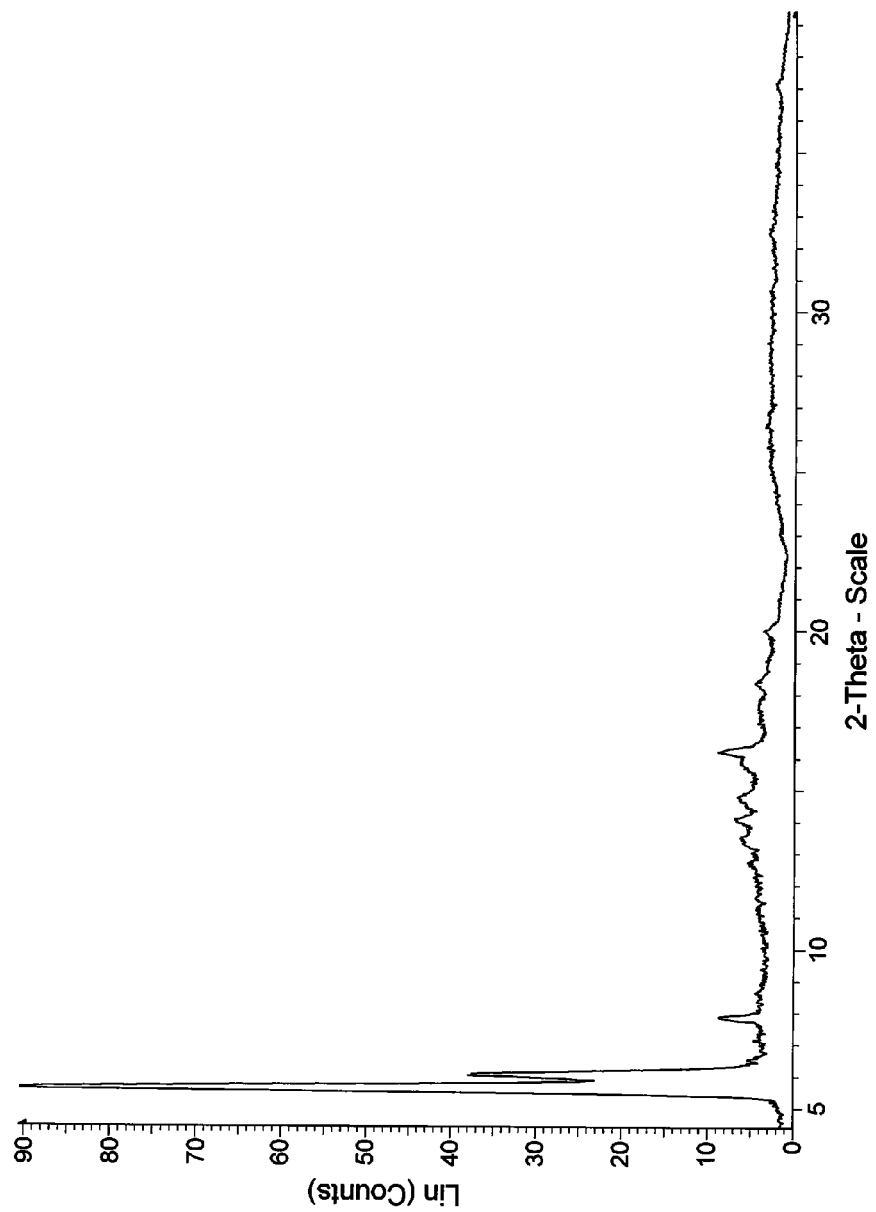
FIG. 2 is an XRPD pattern of Form D of Compound 1.

In another aspect, the invention provides a crystalline solvate Form D of Compound I, which has an XRPD pattern as depicted in FIG. 2. This crystalline solvate form is an acetonitrile solvate, or an acetonitrile/water 75/25 solvate.

In a further embodiment of this aspect, crystalline solvate Form D is characterized by one or more peaks selected from the group consisting of 5.6±0.2 degrees, 6.0±0.2 degrees, 7.8±0.2 degrees, 13.5±0.2 degrees, 14.1±0.2 degrees, 14.7±0.2 degrees, and 16.2±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form D is characterized by a peak at 5.6±0.2 degrees, a peak at 6.0±0.2 degrees, a peak at 7.8±0.2 degrees, a peak at 13.5±0.2 degrees, a peak at 14.1±0.2 degrees, a peak at 14.7±0.2 degrees, and a peak at 16.2±0.2 degrees on a 2θ scale in an X-ray powder diffraction pattern. In a further embodiment, the X-ray powder diffraction pattern is obtained using Cu K alpha radiation.

Figure 3:
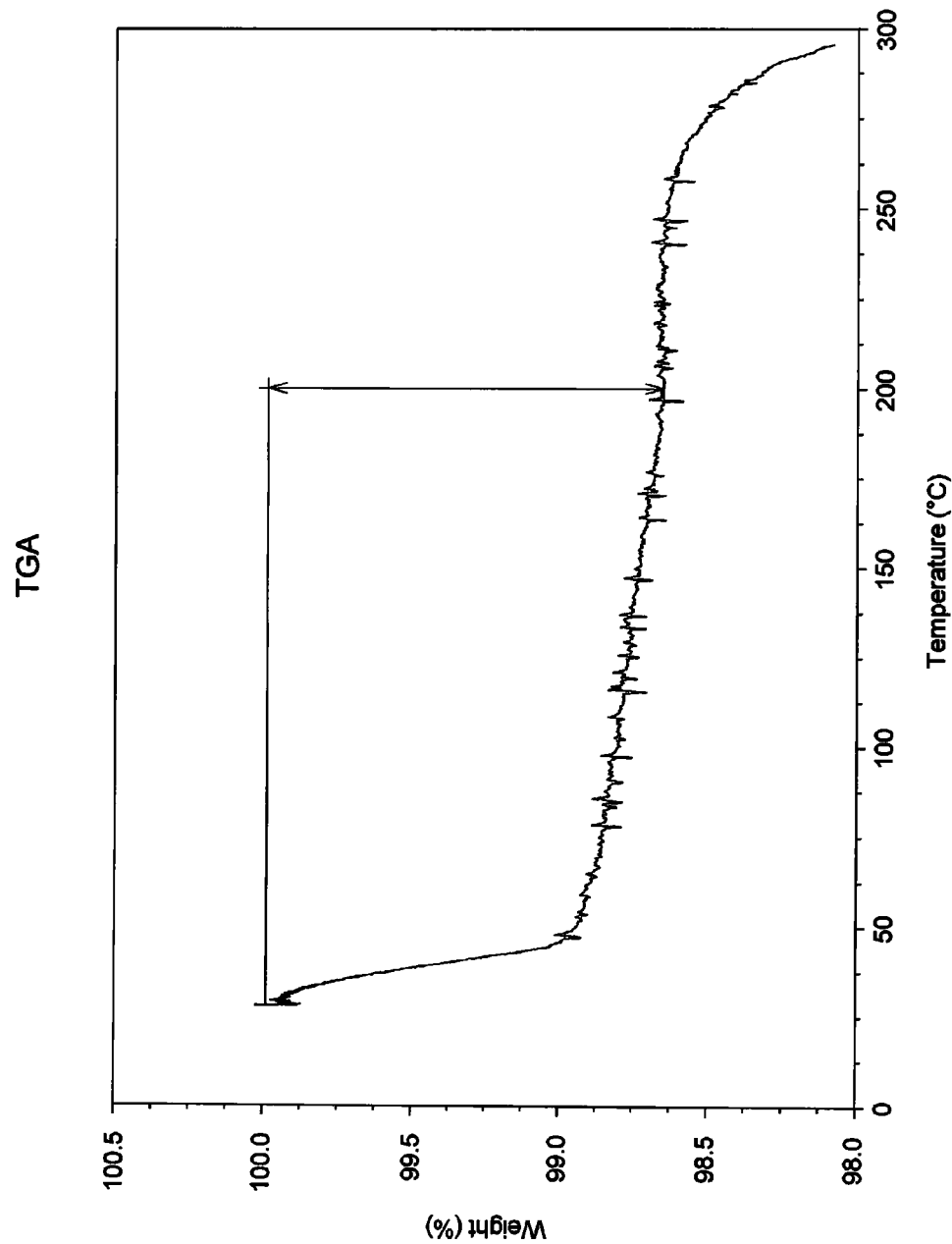
FIG. 3 is a thermogravimetric trace of Form D of Compound 1.

A thermogravimetric trace of Form D is provided as FIG. 3.

Figure 4:
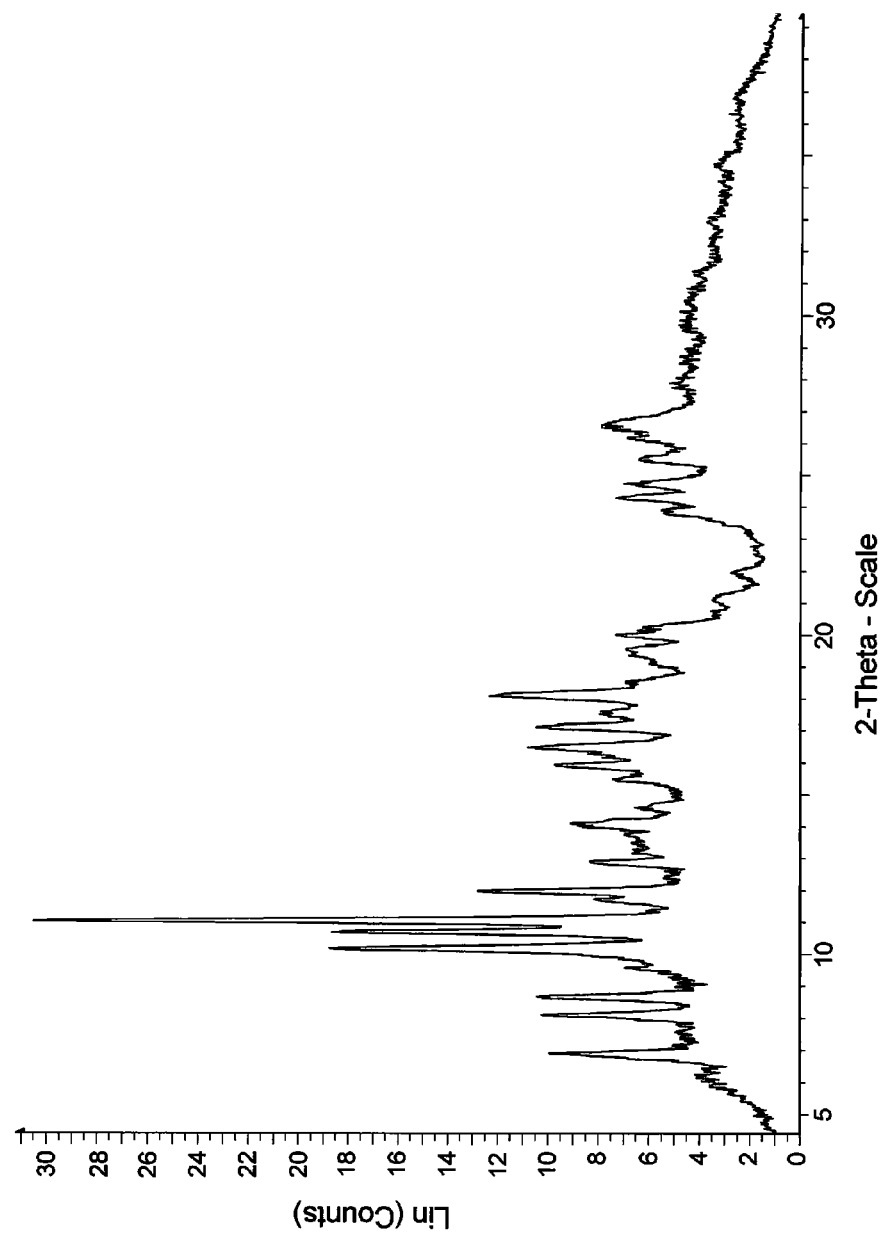
FIG. 4 is an XRPD pattern of Form E of Compound 1.

In another aspect, the invention provides a crystalline solvate Form E of Compound 1, which has an XRPD pattern as depicted in FIG. 4. This crystalline solvate form is a methylethyl ketone (MEK) solvate, a MEK/water 99/1 solvate, MEK/water 90/10 solvate, or a MEK/water 80/20 solvate.

In a further embodiment of this aspect, crystalline solvate Form E is characterized by one or more peaks selected from the group consisting of 8.0±0.2 degrees, 8.6±0.2 degrees, 10.1±0.2 degrees, 11.0±0.2 degrees, 11.9±0.2 degrees, 16.5±0.2 degrees, 17.1±0.2 degrees, and 18.1±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form E is characterized by a peak at 8.0±0.2 degrees, a peak at 8.6±0.2 degrees, a peak at 10.1±0.2 degrees, a peak at 11.0±0.2 degrees, a peak at 11.9±0.2 degrees, a peak at 16.5±0.2 degrees, a peak at 17.1±0.2 degrees, and a peak at 18.1±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form E is characterized by one or more peaks selected from the group consisting of 6.8±0.2 degrees, 8.0±0.2 degrees, 8.6±0.2 degrees, 10.1±0.2 degrees, 10.7±0.2 degrees, 11.0±0.2 degrees, 11.9±0.2 degrees, 12.9±0.2 degrees, 14.0±0.2 degrees, 15.9±0.2 degrees, 16.5±0.2 degrees, 17.1±0.2 degrees, 18.1±0.2 degrees, 20.2±0.2 degrees, 21.1±0.2 degrees, 23.8±0.2 degrees, 24.3±0.2 degrees, 24.7±0.2 degrees, 25.5±0.2 degrees, and 26.6±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form E is characterized by a peak at 6.8±0.2 degrees, a peak at 8.0±0.2 degrees, a peak at 8.6±0.2 degrees, a peak at 10.1±0.2 degrees, a peak at 10.7±0.2 degrees, a peak at 11.0±0.2 degrees, a peak at 11.9±0.2 degrees, a peak at 12.9±0.2 degrees, a peak at 14.0±0.2 degrees, a peak at 15.9±0.2 degrees, a peak at 16.5±0.2 degrees, a peak at 17.1±0.2 degrees, a peak at 18.1±0.2 degrees, a peak at 20.2±0.2 degrees, a peak at 21.1±0.2 degrees, a peak at 23.8±0.2 degrees, a peak at 24.3±0.2 degrees, a peak at 24.7±0.2 degrees, a peak at 25.5±0.2 degrees, and a peak at 26.6±0.2 degrees on a 2θ scale in an X-ray powder diffraction pattern. In a further embodiment, the X-ray powder diffraction pattern is obtained using Cu K alpha radiation.

Figure 5:
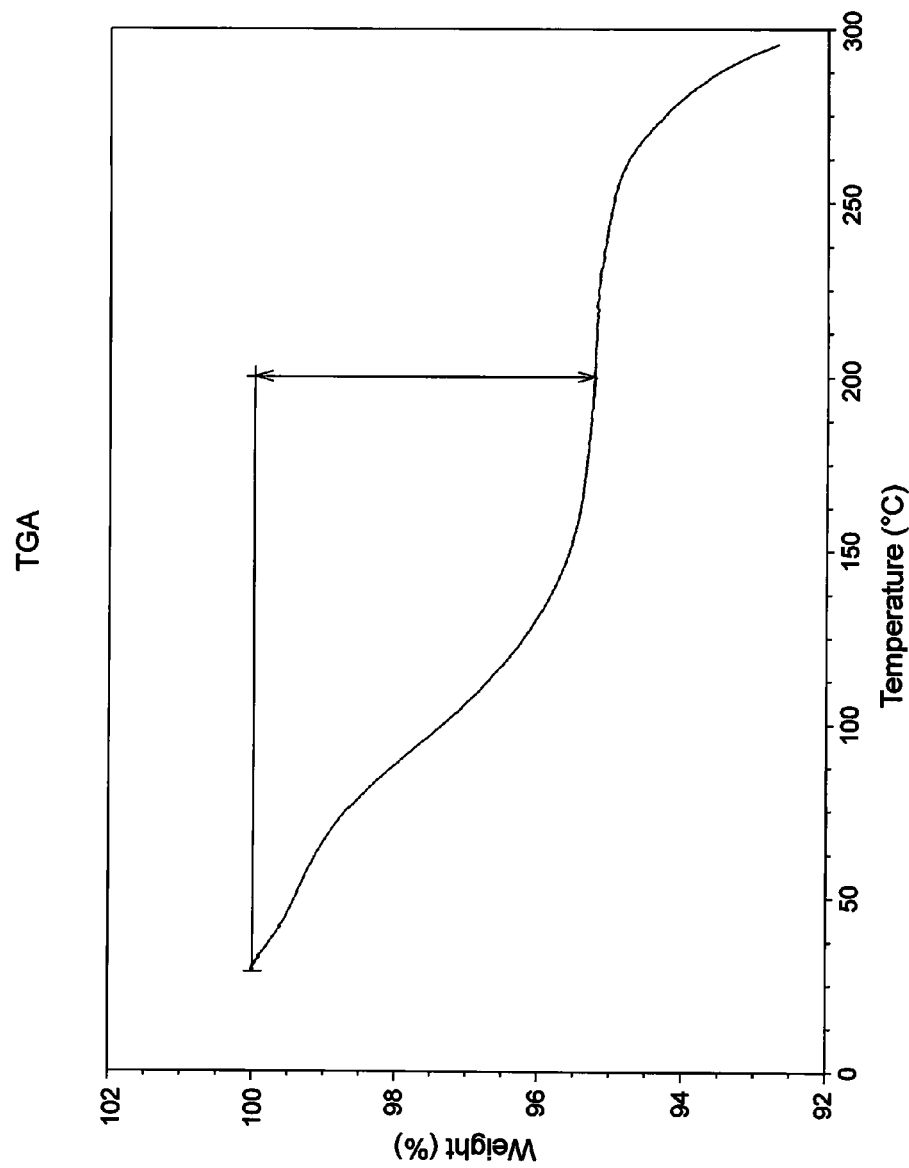
FIG. 5 is a thermogravimetric trace of Form E of Compound 1.

A thermogravimetric trace of Form E is provided as FIG. 5.

Figure 6:
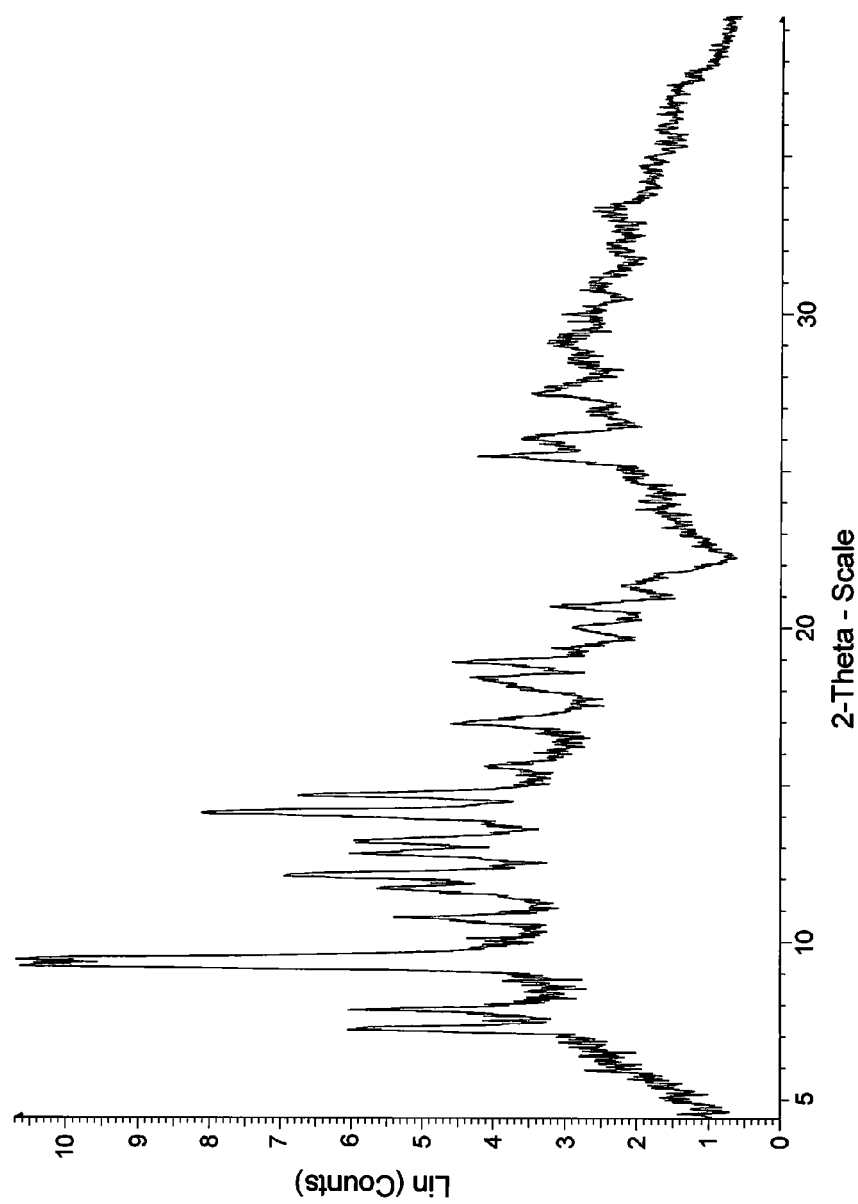
FIG. 6 is an XRPD pattern of Form F of Compound 1.

In another aspect, the invention provides a crystalline solvate Form F of Compound 1, which has an XRPD pattern as depicted in FIG. 6. This crystalline solvate form is an acetonitrile/water 75/25 solvate.

In one embodiment of this aspect, Form F is characterized by one or more peaks selected from the group consisting of 7.2±0.2 degrees, 7.8±0.2 degrees, 9.4±0.2 degrees, 10.7±0.2 degrees, 12.1±0.2 degrees, 12.8±0.2 degrees, 14.1±0.2 degrees, and 14.7±0.2 degrees on a 2θ scale in an X-ray powder diffraction pattern. In a further embodiment, the X-ray powder diffraction pattern is obtained using Cu K alpha radiation.

In one embodiment of this aspect, Form F is characterized by a peak at 7.2±0.2 degrees, a peak at 7.8±0.2 degrees, a peak at 9.4±0.2 degrees, a peak at 10.7±0.2 degrees, a peak at 12.1±0.2 degrees, a peak at 12.8±0.2 degrees, a peak at 14.1±0.2 degrees, and a peak at 14.7±0.2 degrees on a 2θ scale in an X-ray powder diffraction pattern. In a further embodiment, the X-ray powder diffraction pattern is obtained using Cu K alpha radiation.

In one embodiment of this aspect, Form F is characterized by one or more peaks selected from the group consisting of 7.2±0.2 degrees, 7.8±0.2 degrees, 9.4±0.2 degrees, 10.7±0.2 degrees, 11.7±0.2 degrees, 12.1±0.2 degrees, 12.8±0.2 degrees, 13.2±0.2 degrees, 14.1±0.2 degrees, 14.7±0.2 degrees 15.6±0.2 degrees, 17.0±0.2 degrees, 18.3±0.2 degrees, 18.9±0.2 degrees, 20.0±0.2 degrees, 20.6±0.2 degrees, 21.3±0.2 degrees, 25.5±0.2 degrees, 26.0±0.2 degrees, and 27.4±0.2 degrees on a 2θ scale in an X-ray powder diffraction pattern. In a further embodiment, the X-ray powder diffraction pattern is obtained using Cu K alpha radiation.

In one embodiment of this aspect, Form F is characterized by a peak at 7.2±0.2 degrees, a peak at 7.8±0.2 degrees, a peak at 9.4±0.2 degrees, a peak at 10.7±0.2 degrees, a peak at 11.7±0.2 degrees, a peak at 12.1±0.2 degrees, a peak at 12.8±0.2 degrees, a peak at 13.2±0.2 degrees, a peak at 14.1±0.2 degrees, a peak at 14.7±0.2 degrees a peak at 15.6±0.2 degrees, a peak at 17.0±0.2 degrees, a peak at 18.3±0.2 degrees, a peak at 18.9±0.2 degrees, a peak at 20.0±0.2 degrees, a peak at 20.6±0.2 degrees, a peak at 21.3±0.2 degrees, a peak at 25.5±0.2 degrees, a peak at 26.0±0.2 degrees, and a peak at 27.4±0.2 degrees on a 2θ scale in an X-ray powder diffraction pattern. In a further embodiment, the X-ray powder diffraction pattern is obtained using Cu K alpha radiation.

Figure 7:
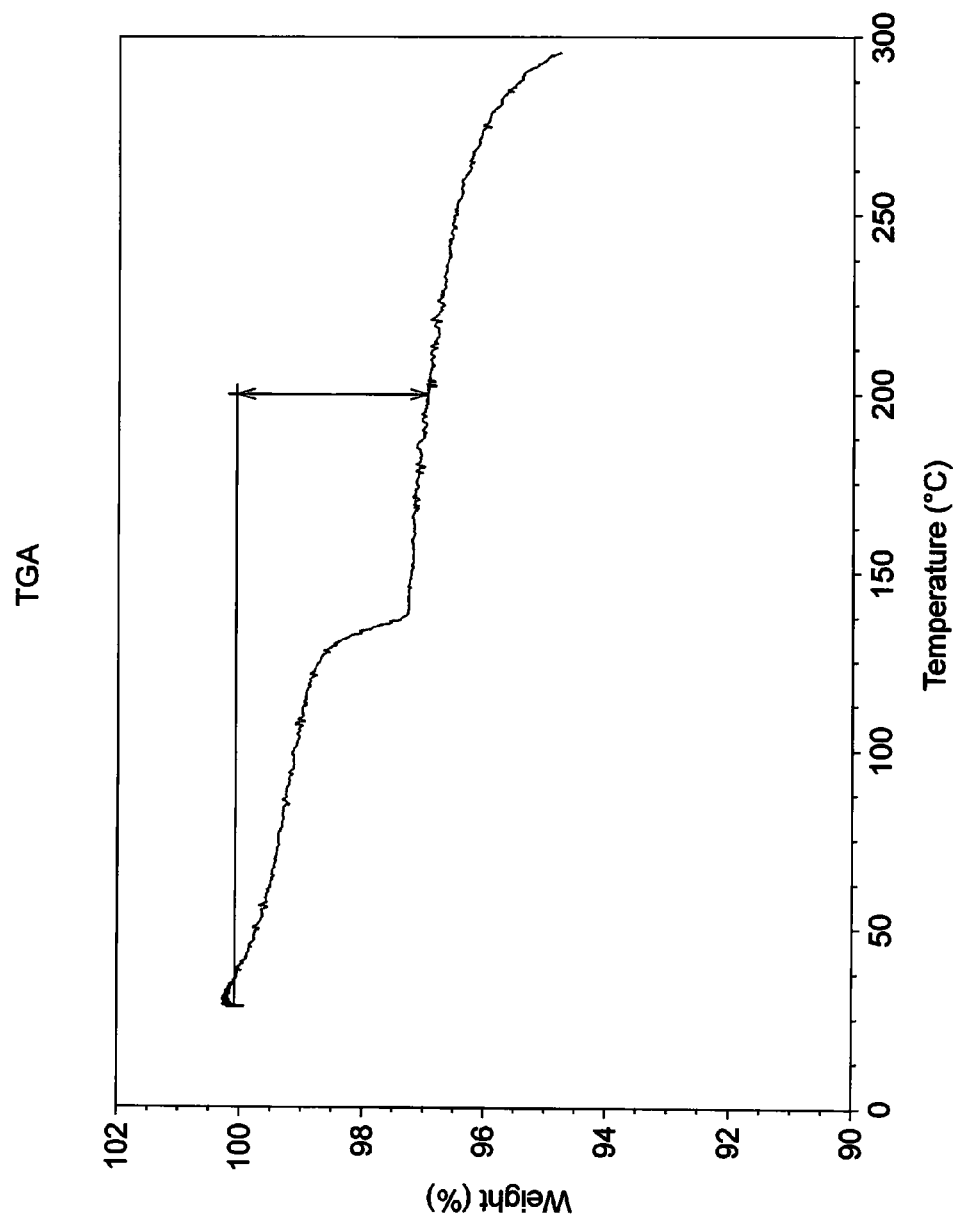
FIG. 7 is a thermogravimetric trace of Form F of Compound 1.

A thermogravimetric trace of Form F is provided as FIG. 7.

Figure 8:
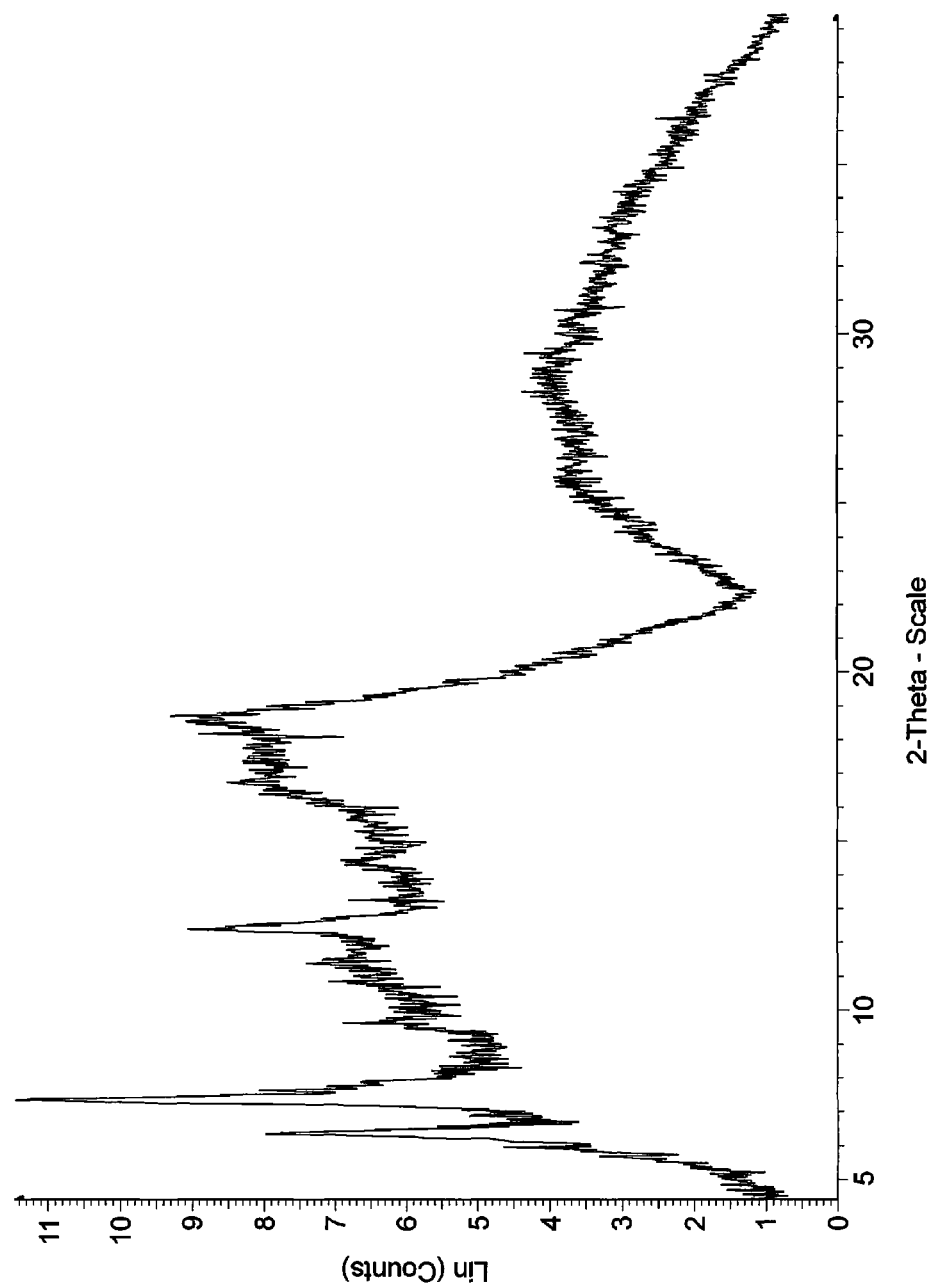
FIG. 8 is an XRPD pattern of Form G of Compound 1.

In another aspect, the invention provides a crystalline solvate Form G of Compound 1, which has an XRPD pattern as depicted in FIG. 8. This crystalline solvate form is an isopropyl acetate solvate.

In one embodiment of this aspect, Form G is characterized by one or more peaks selected from the group consisting of 6.3±0.2 degrees, 7.3±0.2 degrees, and 12.4±0.2 degrees on a 2θ scale in an X-ray powder diffraction pattern. In a further embodiment, the X-ray powder diffraction pattern is obtained using Cu K alpha radiation.

In one embodiment of this aspect, Form G is characterized by a peak at 6.3±0.2 degrees, a peak at 7.3±0.2 degrees, and a peak at 12.4±0.2 degrees on a 2θ scale in an X-ray powder diffraction pattern. In a further embodiment, the X-ray powder diffraction pattern is obtained using Cu K alpha radiation.

Figure 9:
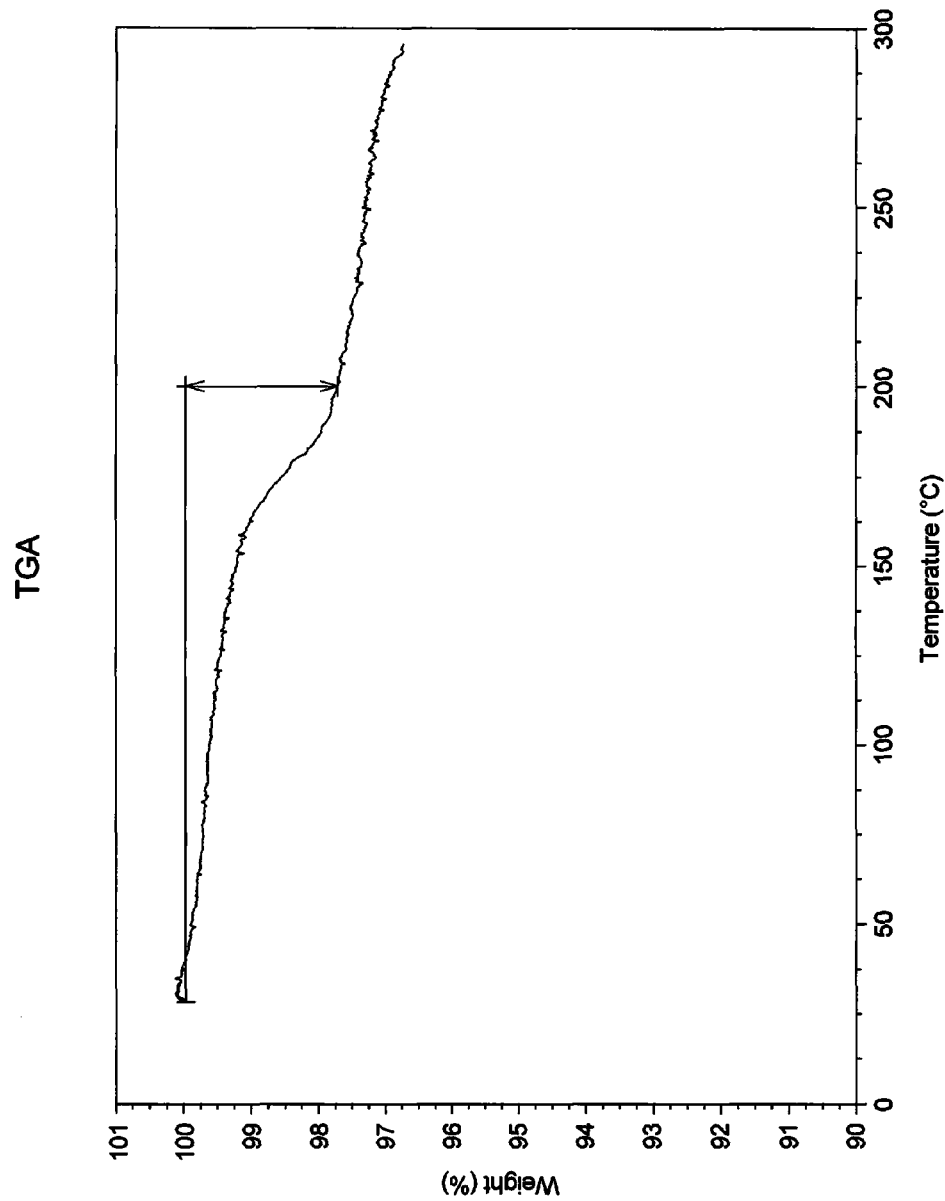
FIG. 9 is a thermogravimetric trace of Form G of Compound 1.

A thermogravimetric trace of Form G is provided as FIG. 9.

Figure 10:
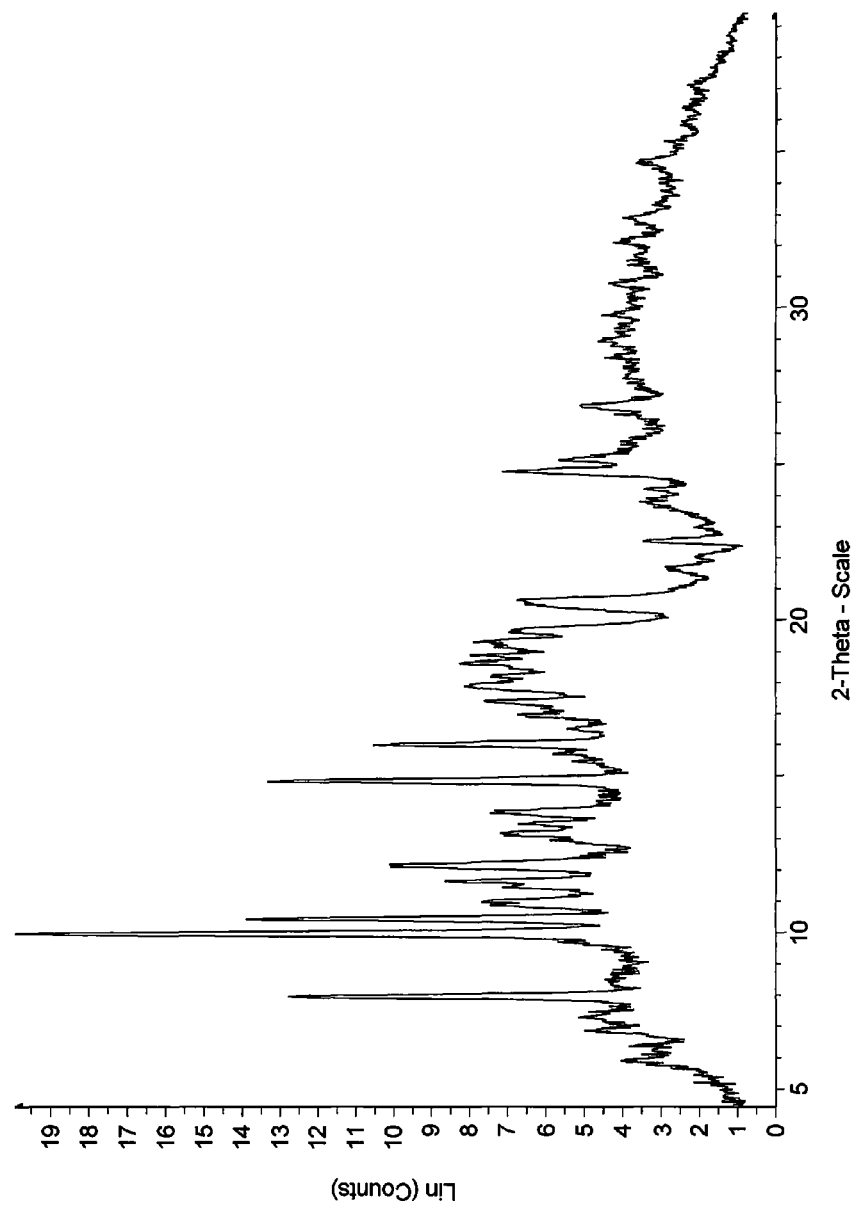
FIG. 10 is an XRPD pattern of Form H of Compound 1.

In another aspect, the invention provides a crystalline solvate Form H of Compound I, which has an XRPD pattern as depicted in FIG. 10. This crystalline solvate form is an isopropyl acetate/water 95/5 solvate.

In a further embodiment of this aspect, crystalline solvate Form H is characterized by one or more peaks selected from the group consisting of 7.9±0.2 degrees, 9.9±0.2 degrees, 10.4±0.2 degrees, 11.6±0.2 degrees, 12.1±0.2 degrees, 14.8±0.2 degrees, 16.0±0.2 degrees, and 17.9±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form H is characterized by a peak at 7.9±0.2 degrees, a peak at 9.9±0.2 degrees, a peak at 10.4±0.2 degrees, a peak at 11.6±0.2 degrees, a peak at 12.1±0.2 degrees, a peak at 14.8±0.2 degrees, a peak at 16.0±0.2 degrees, and a peak at 17.9±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form H is characterized by one or more peaks selected from the group consisting of 5.9±0.2 degrees, 7.9±0.2 degrees, 9.9±0.2 degrees, 10.4±0.2 degrees, 10.9±0.2 degrees, 11.6±0.2 degrees, 12.1±0.2 degrees, 13.2±0.2 degrees, 13.8±0.2 degrees, 14.8±0.2 degrees, 16.0±0.2 degrees, 17.4±0.2 degrees, 17.9±0.2 degrees, 19.6±0.2 degrees, 20.6±0.2 degrees, 21.6±0.2 degrees, 22.5±0.2 degrees, 23.8±0.2 degrees, 24.8±0.2 degrees, and 26.9±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form H is characterized by a peak at 5.9±0.2 degrees, a peak at 7.9±0.2 degrees, a peak at 9.9±0.2 degrees, a peak at 10.4±0.2 degrees, a peak at 10.9±0.2 degrees, a peak at 11.6±0.2 degrees, a peak at 12.1±0.2 degrees, a peak at 13.2±0.2 degrees, a peak at 13.8±0.2 degrees, a peak at 14.8±0.2 degrees, a peak at 16.0±0.2 degrees, a peak at 17.4±0.2 degrees, a peak at 17.9±0.2 degrees, a peak at 19.6±0.2 degrees, a peak at 20.6±0.2 degrees, a peak at 21.6±0.2 degrees, a peak at 22.5±0.2 degrees, a peak at 23.8±0.2 degrees, a peak at 24.8±0.2 degrees, and a peak at 26.9±0.2 degrees on a 2θ scale in an X-ray powder diffraction pattern. In a further embodiment, the X-ray powder diffraction pattern is obtained using Cu K alpha radiation.

Figure 11:
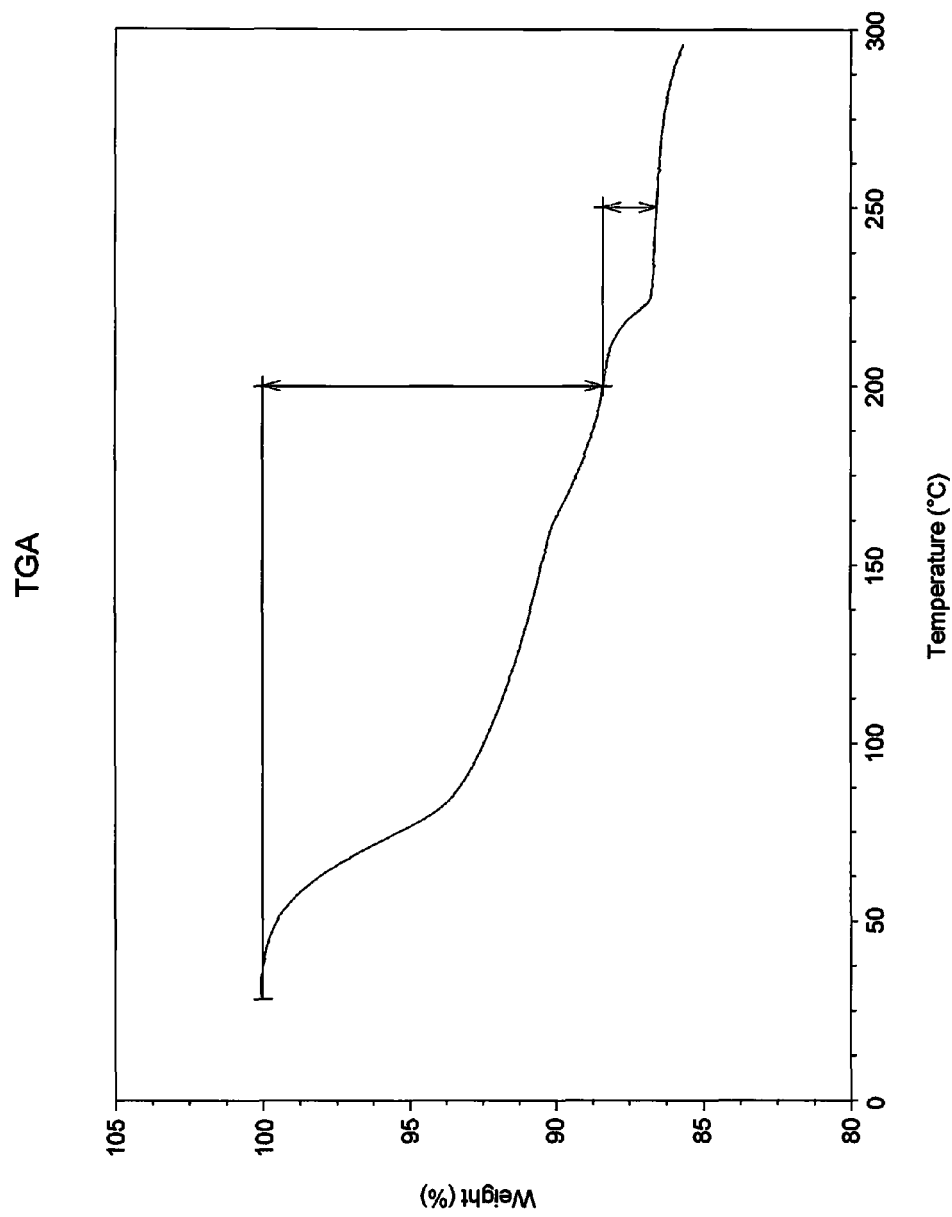
FIG. 11 is a thermogravimetric trace of Form H of Compound 1.

A thermogravimetric trace of Form H is provided as FIG. 11.

Figure 12:
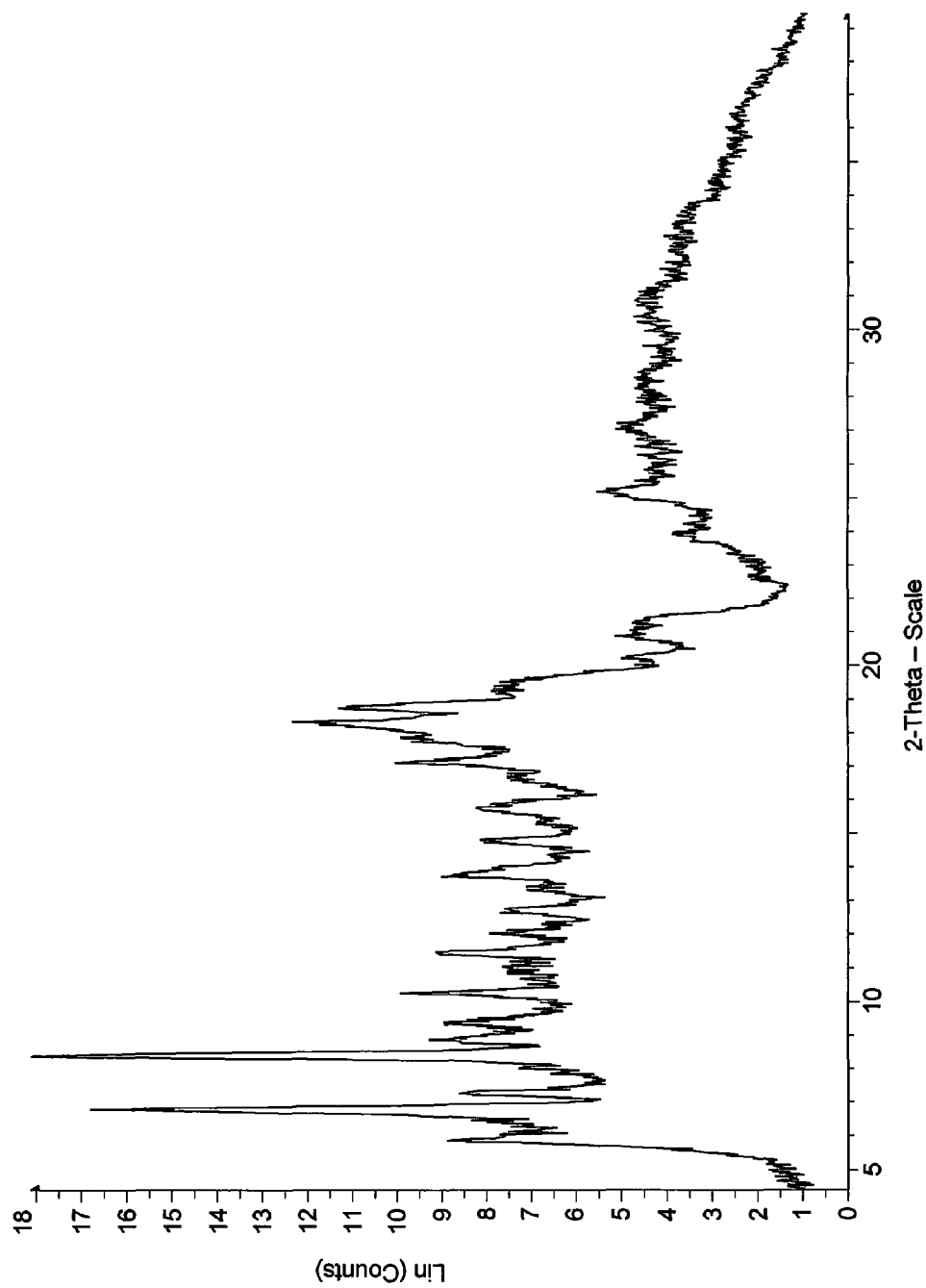
FIG. 12 is an XRPD pattern of Form I of Compound 1.

In another aspect, the invention provides a crystalline solvate Form I of Compound 1, which has an XRPD pattern as depicted in FIG. 12. This crystalline solvate form is a MEK solvate.

In a further embodiment of this aspect, crystalline solvate Form I is characterized by one or more peaks selected from the group consisting of 6.8±0.2 degrees, 8.4±0.2 degrees, 9.4±0.2 degrees, 10.2±0.2 degrees, 11.4±0.2 degrees, 17.1±0.2 degrees, 17.8±0.2 degrees, and 18.3±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form I is characterized by a peak at 6.8±0.2 degrees, a peak at 8.4±0.2 degrees, a peak at 9.4±0.2 degrees, a peak at 10.2±0.2 degrees, a peak at 11.4±0.2 degrees, a peak at 17.1±0.2 degrees, a peak at 17.8±0.2 degrees, and a peak at 18.3±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form I is characterized by one or more peaks selected from the group consisting of 5.8±0.2 degrees, 6.8±0.2 degrees, 7.2±0.2 degrees, 8.4±0.2 degrees, 8.8±0.2 degrees, 9.4±0.2 degrees, 10.2±0.2 degrees, 11.4±0.2 degrees, 12.7±0.2 degrees, 13.7±0.2 degrees, 14.8±0.2 degrees, 15.7±0.2 degrees, 17.1±0.2 degrees, 17.8±0.2 degrees, 18.3±0.2 degrees, 18.8±0.2 degrees, 20.2±0.2 degrees, 21.3±0.2 degrees, 23.9±0.2 degrees, and 25.2±0.2 degrees, on a 2θ scale in an X-ray powder diffraction pattern. In a further embodiment, the X-ray powder diffraction pattern is obtained using Cu K alpha radiation.

In a further embodiment of this aspect, crystalline solvate Form I is characterized by a peak at 5.8±0.2 degrees, a peak at 6.8±0.2 degrees, a peak at 7.2±0.2 degrees, a peak at 8.4±0.2 degrees, a peak at 8.8±0.2 degrees, a peak at 9.4±0.2 degrees, a peak at 10.2±0.2 degrees, a peak at 11.4±0.2 degrees, a peak at 12.7±0.2 degrees, a peak at 13.7±0.2 degrees, a peak at 14.8±0.2 degrees, a peak at 15.7±0.2 degrees, a peak at 17.1±0.2 degrees, a peak at 17.8±0.2 degrees, a peak at 18.3±0.2 degrees, a peak at 18.8±0.2 degrees, a peak at 20.2±0.2 degrees, a peak at 21.3±0.2 degrees, a peak at 23.9±0.2 degrees, and a peak at 25.2±0.2 degrees, on a 2θ scale in an X-ray powder diffraction pattern. In a further embodiment, the X-ray powder diffraction pattern is obtained using Cu K alpha radiation.

Figure 13:
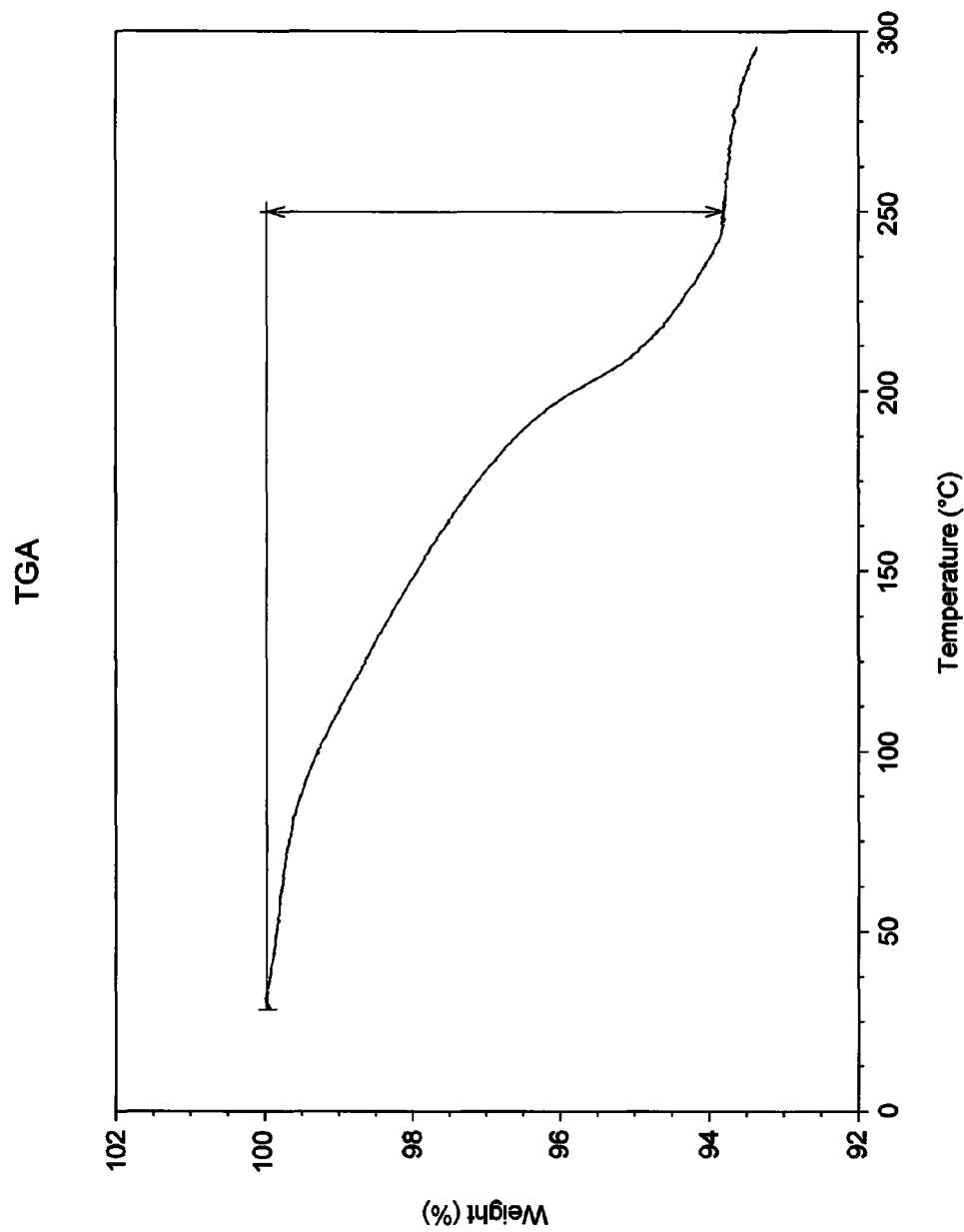
FIG. 13 is a thermogravimetric trace of Form I of Compound 1.

A thermogravimetric trace of Form I is provided as FIG. 13.

Figure 14:
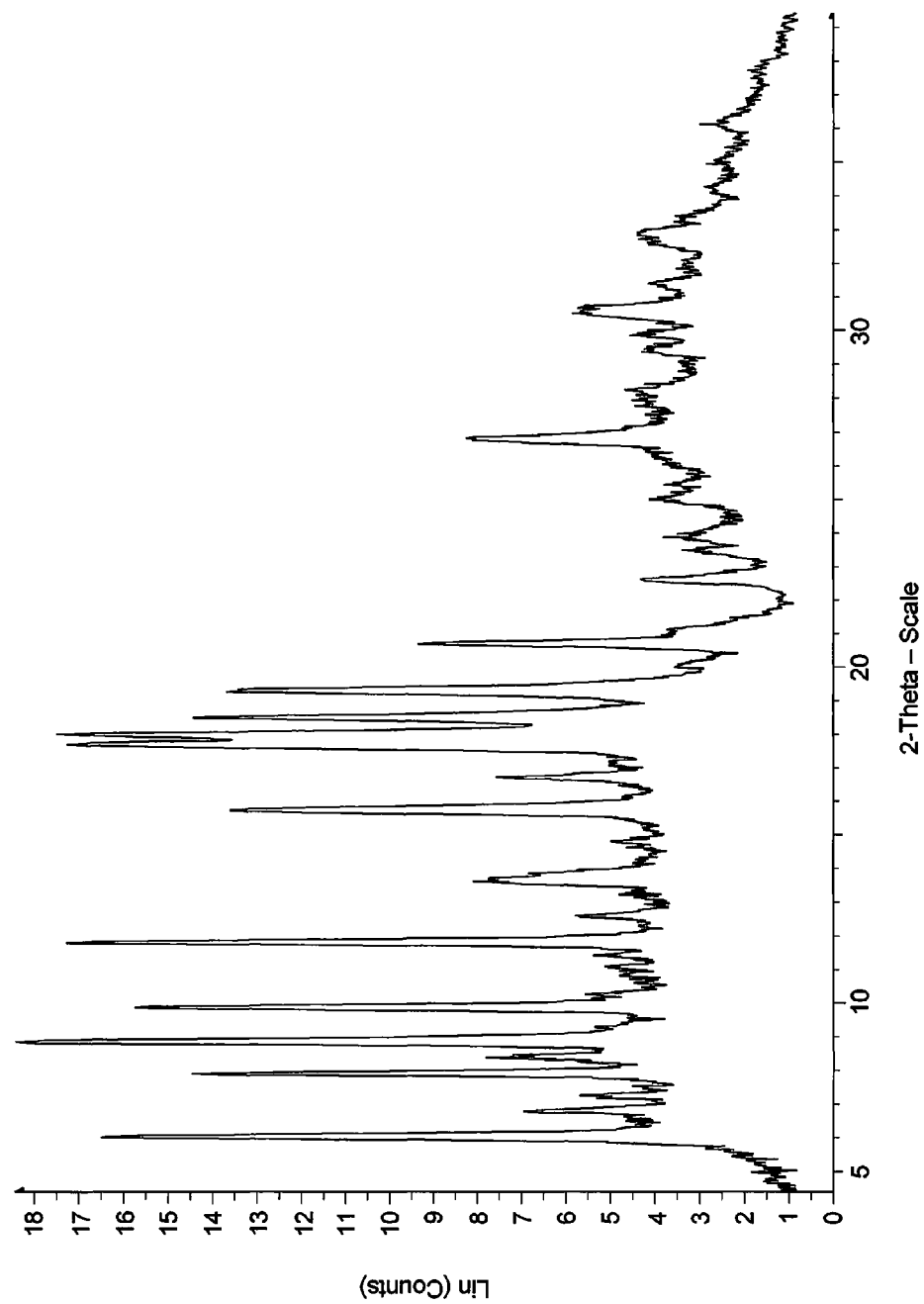
FIG. 14 is an XRPD pattern of Form J of Compound 1.

In another aspect, the invention provides a crystalline solvate Form J of Compound 1, which has an XRPD pattern as depicted in FIG. 14. This crystalline solvate form is a MEK/water 99/1 solvate.

In one embodiment of this aspect, Form J is characterized by one or more peaks selected from the group consisting of 6.0±0.2 degrees, 7.9±0.2 degrees, 8.8±0.2 degrees, 9.9±0.2 degrees, 11.8±0.2 degrees, 17.7±0.2 degrees, 18.0±0.2 degrees, and 18.5±0.2 degrees on a 2θ scale in an X-ray powder diffraction pattern. In a further embodiment, the X-ray powder diffraction pattern is obtained using Cu K alpha radiation.

In one embodiment of this aspect, Form J is characterized by a peak at 6.0±0.2 degrees, a peak at 7.9±0.2 degrees, a peak at 8.8±0.2 degrees, a peak at 9.9±0.2 degrees, a peak at 11.8±0.2 degrees, a peak at 17.7±0.2 degrees, a peak at 18.0±0.2 degrees, and a peak at 18.5±0.2 degrees on a 2θ scale in an X-ray powder diffraction pattern. In a further embodiment, the X-ray powder diffraction pattern is obtained using Cu K alpha radiation.

In one embodiment of this aspect, Form J is characterized by one or more peaks selected from the group consisting of 6.0±0.2 degrees, 6.8±0.2 degrees, 7.9±0.2 degrees, 8.4±0.2 degrees, 8.8±0.2 degrees, 9.9±0.2 degrees, 11.8±0.2 degrees, 12.6±0.2 degrees, 13.6±0.2 degrees, 15.7±0.2 degrees, 16.7±0.2 degrees, 17.7±0.2 degrees, 18.0±0.2 degrees, 18.5±0.2 degrees, 19.3±0.2 degrees, 20.7±0.2 degrees, 22.6±0.2 degrees, 26.8±0.2 degrees, and 29.4±0.2 degrees on a 2θ scale in an X-ray powder diffraction pattern. In a further embodiment, the X-ray powder diffraction pattern is obtained using Cu K alpha radiation.

In one embodiment of this aspect, Form J is characterized by a peak at 6.0±0.2 degrees, a peak at 6.8±0.2 degrees, a peak at 7.9±0.2 degrees, a peak at 8.4±0.2 degrees, a peak at 8.8±0.2 degrees, a peak at 9.9±0.2 degrees, a peak at 11.8±0.2 degrees, a peak at 12.6±0.2 degrees, a peak at 13.6±0.2 degrees, a peak at 15.7±0.2 degrees, a peak at 16.7±0.2 degrees, a peak at 17.7±0.2 degrees, a peak at 18.0±0.2 degrees, a peak at 18.5±0.2 degrees, a peak at 19.3±0.2 degrees, a peak at 20.7±0.2 degrees, a peak at 22.6±0.2 degrees, a peak at 26.8±0.2 degrees, and a peak at 29.4±0.2 degrees on a 2θ scale in an X-ray powder diffraction pattern. In a further embodiment, the X-ray powder diffraction pattern is obtained using Cu K alpha radiation.

Figure 15:
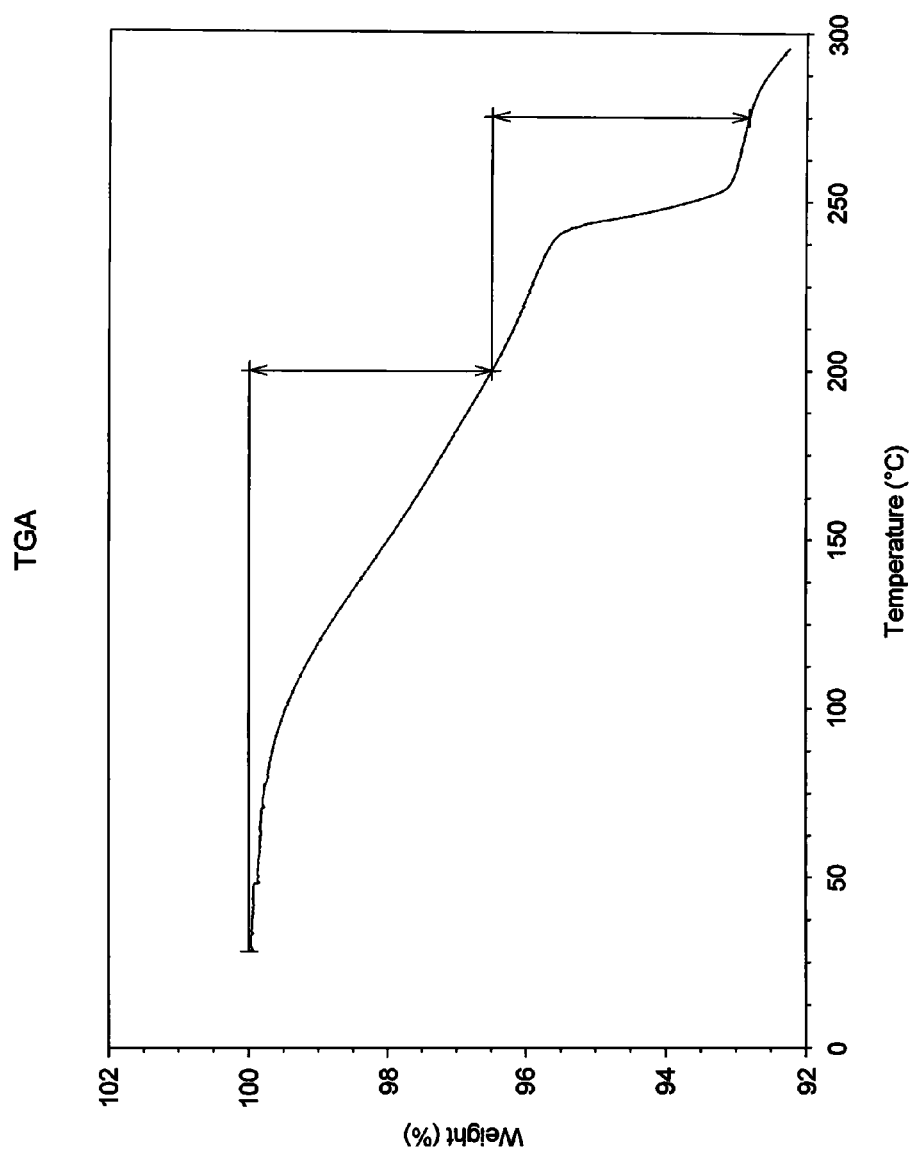
FIG. 15 is a thermogravimetric trace of Form J of Compound 1.

A thermogravimetric trace of Form J is provided as FIG. 15.

Figure 16:
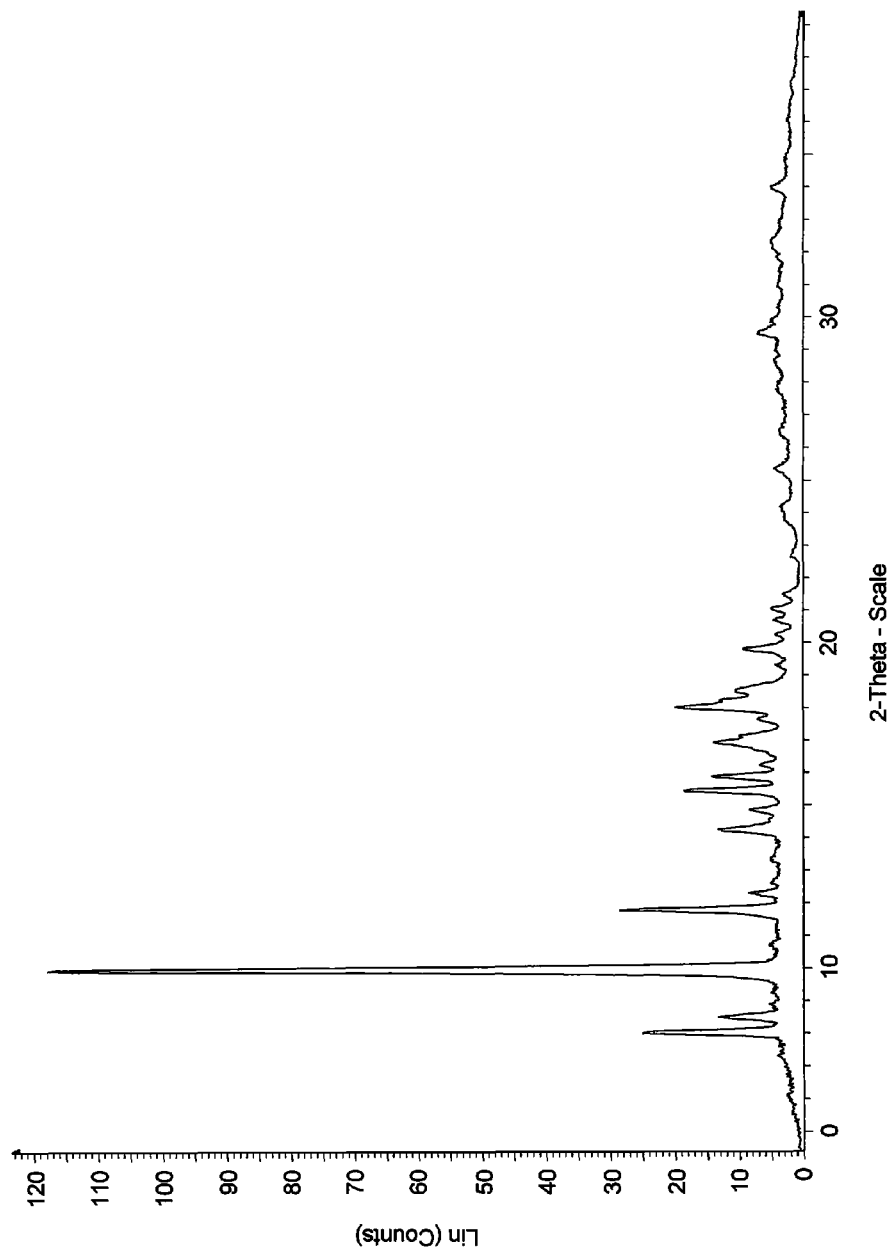
FIG. 16 is an XRPD pattern of Form K of Compound 1.

In another aspect, the invention provides a crystalline solvate Form K of Compound I, which has an XRPD pattern as depicted in FIG. 16. This crystalline solvate form is a methylethyl ketone (MEK) solvate, a MEK/water 99/1 solvate, MEK/water 90/10 solvate, or a MEK/water 80/20 solvate.

In a further embodiment of this aspect, crystalline solvate Form K is characterized by one or more peaks selected from the group consisting of 8.0±0.2 degrees, 8.5±0.2 degrees, 10.0±0.2 degrees, 11.8±0.2 degrees, 15.4±0.2 degrees, 15.9±0.2 degrees, 16.9±0.2 degrees, and 18.0±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form K is characterized by a peak at 8.0±0.2 degrees, a peak at 8.5±0.2 degrees, a peak at 10.0±0.2 degrees, a peak at 11.8±0.2 degrees, a peak at 15.4±0.2 degrees, a peak at 15.9±0.2 degrees, a peak at 16.9±0.2 degrees, and a peak at 18.0±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form K is characterized by one or more peaks selected from the group consisting of 8.0±0.2 degrees, 8.5±0.2 degrees, 10.0±0.2 degrees, 11.8±0.2 degrees, 12.3±0.2 degrees, 14.2±0.2 degrees, 14.8±0.2 degrees, 15.4±0.2 degrees, 15.9±0.2 degrees, 16.9±0.2 degrees, 18.0±0.2 degrees, 18.5±0.2 degrees, 19.8±0.2 degrees, 20.2±0.2 degrees, 20.7±0.2 degrees, 21.0±0.2 degrees, 21.5±0.2 degrees, 22.7±0.2 degrees, and 29.5±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form K is characterized by a peak at 8.0±0.2 degrees, a peak at 8.5±0.2 degrees, a peak at 10.0±0.2 degrees, a peak at 11.8±0.2 degrees, a peak at 12.3±0.2 degrees, a peak at 14.2±0.2 degrees, a peak at 14.8±0.2 degrees, a peak at 15.4±0.2 degrees, a peak at 15.9±0.2 degrees, a peak at 16.9±0.2 degrees, a peak at 18.0±0.2 degrees, a peak at 18.5±0.2 degrees, a peak at 19.8±0.2 degrees, a peak at 20.2±0.2 degrees, a peak at 20.7±0.2 degrees, a peak at 21.0±0.2 degrees, a peak at 21.5±0.2 degrees, a peak at 22.7±0.2 degrees, and a peak at 29.5±0.2 degrees on a 2θ scale in an X-ray powder diffraction pattern. In a further embodiment, the X-ray powder diffraction pattern is obtained using Cu K alpha radiation.

Figure 17:
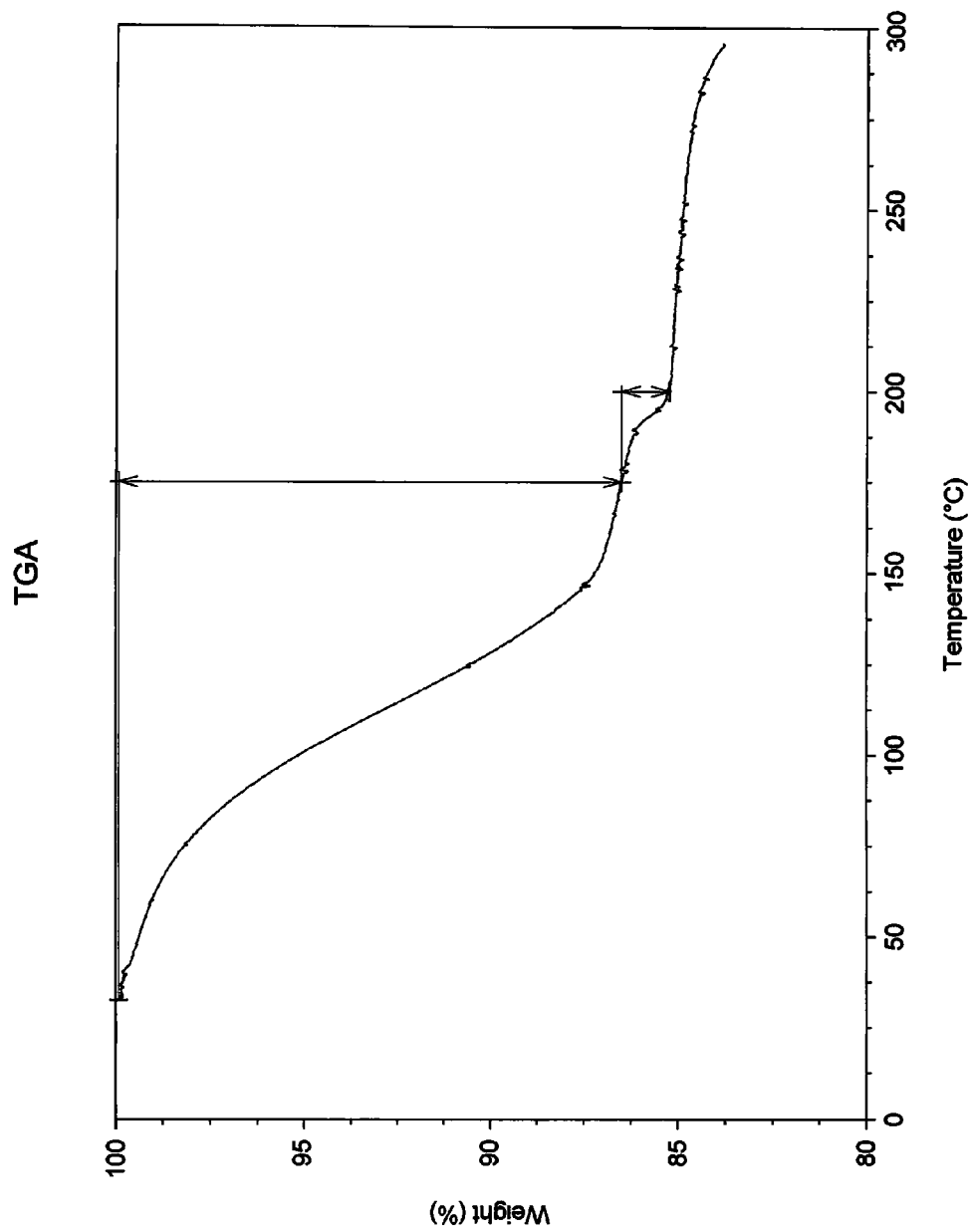
FIG. 17 is a thermogravimetric trace of Form K of Compound 1.

A thermogravimetric trace of Form K is provided as FIG. 17.

Figure 18:
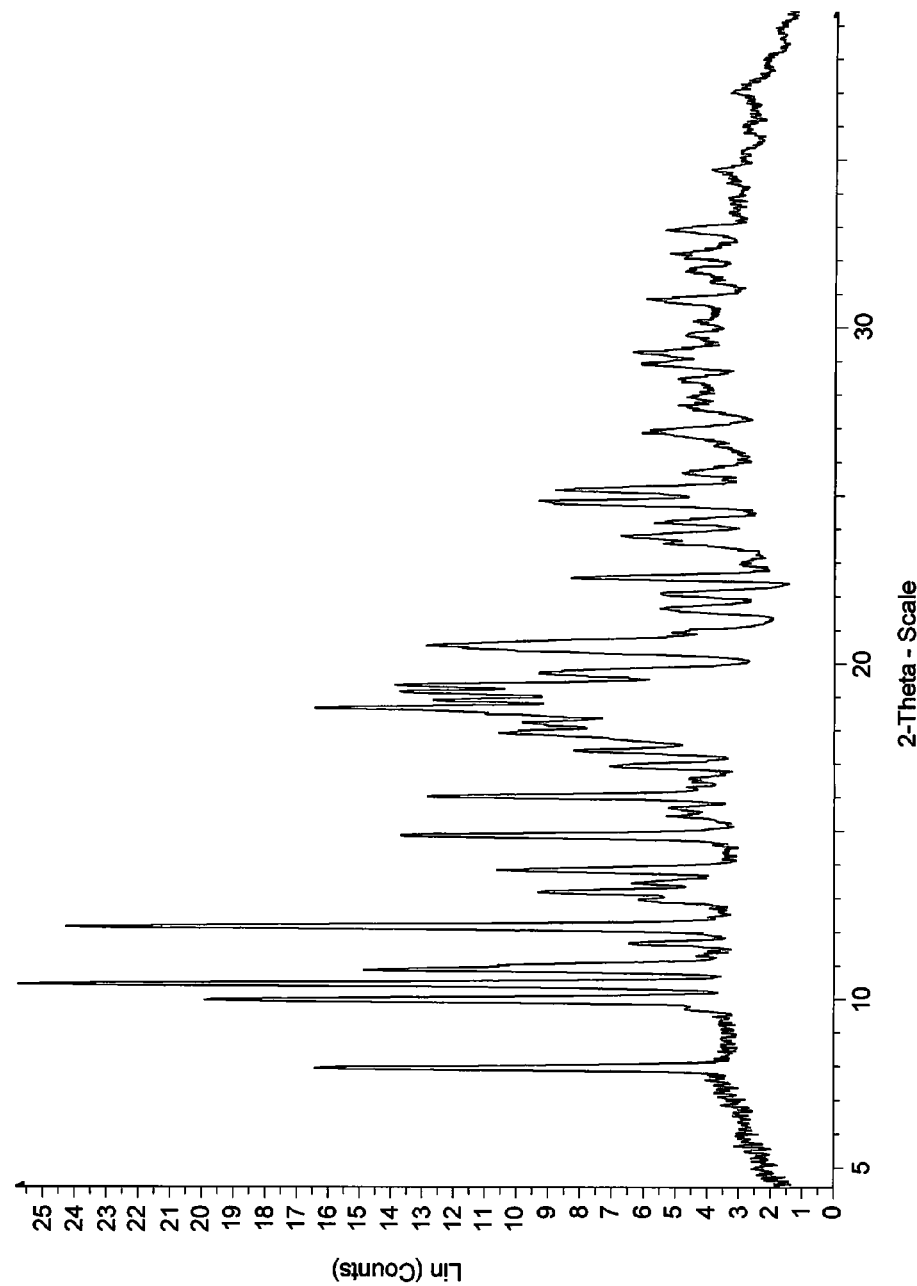
FIG. 18 is an XRPD pattern of Form L of Compound 1.

In another aspect, the invention provides a crystalline solvate Form L of Compound 1, which has an XRPD pattern as depicted in FIG. 18. This crystalline solvate form is an isopropyl acetate/water 95/5 solvate.

In a further embodiment of this aspect, crystalline solvate Form L is characterized by one or more peaks selected from the group consisting of 7.9±0.2 degrees, 10.4±0.2 degrees, 10.9±0.2 degrees, 12.1±0.2 degrees, 14.8±0.2 degrees, 16.0±0.2 degrees, 18.6±0.2 degrees, and 20.5±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form L is characterized by a peak at 7.9±0.2 degrees, a peak at 10.4±0.2 degrees, a peak at 10.9±0.2 degrees, a peak at 12.1±0.2 degrees, a peak at 14.8±0.2 degrees, a peak at 16.0±0.2 degrees, a peak at 18.6±0.2 degrees, and a peak at 20.5±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form L is characterized by one or more peaks selected from the group consisting of 7.9±0.2 degrees, 10.0±0.2 degrees, 10.4±0.2 degrees, 10.9±0.2 degrees, 12.1±0.2 degrees, 13.2±0.2 degrees, 13.8±0.2 degrees, 14.8±0.2 degrees, 16.0±0.2 degrees, 16.9±0.2 degrees, 17.4±0.2 degrees, 18.6±0.2 degrees, 19.7±0.2 degrees, 20.5±0.2 degrees, 21.6±0.2 degrees, 22.1±0.2 degrees, 22.5±0.2 degrees, 24.8±0.2 degrees, and 25.2±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form L is characterized by a peak at 7.9±0.2 degrees, a peak at 10.0±0.2 degrees, a peak at 10.4±0.2 degrees, a peak at 10.9±0.2 degrees, a peak at 12.1±0.2 degrees, a peak at 13.2±0.2 degrees, a peak at 13.8±0.2 degrees, a peak at 14.8±0.2 degrees, a peak at 16.0±0.2 degrees, a peak at 16.9±0.2 degrees, a peak at 17.4±0.2 degrees, a peak at 18.6±0.2 degrees, a peak at 19.7±0.2 degrees, a peak at 20.5±0.2 degrees, a peak at 21.6±0.2 degrees, a peak at 22.1±0.2 degrees, a peak at 22.5±0.2 degrees, a peak at 24.8±0.2 degrees, and a peak at 25.2±0.2 degrees on a 2θ scale in an X-ray powder diffraction pattern. In a further embodiment, the X-ray powder diffraction pattern is obtained using Cu K alpha radiation.

Figure 19:
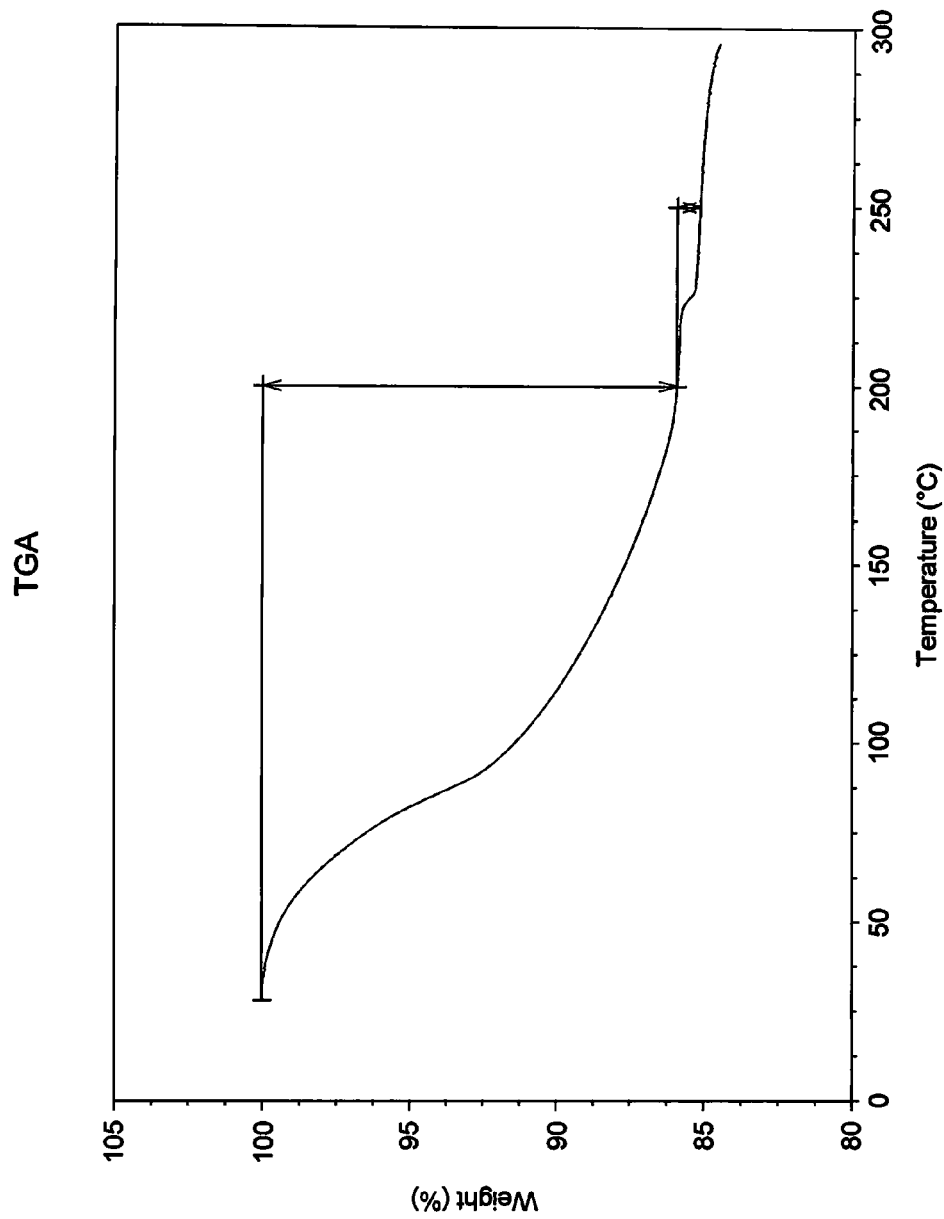
FIG. 19 is a thermogravimetric trace of Form L of Compound 1.

A thermogravimetric trace of Form L is provided as FIG. 19.

Figure 20:
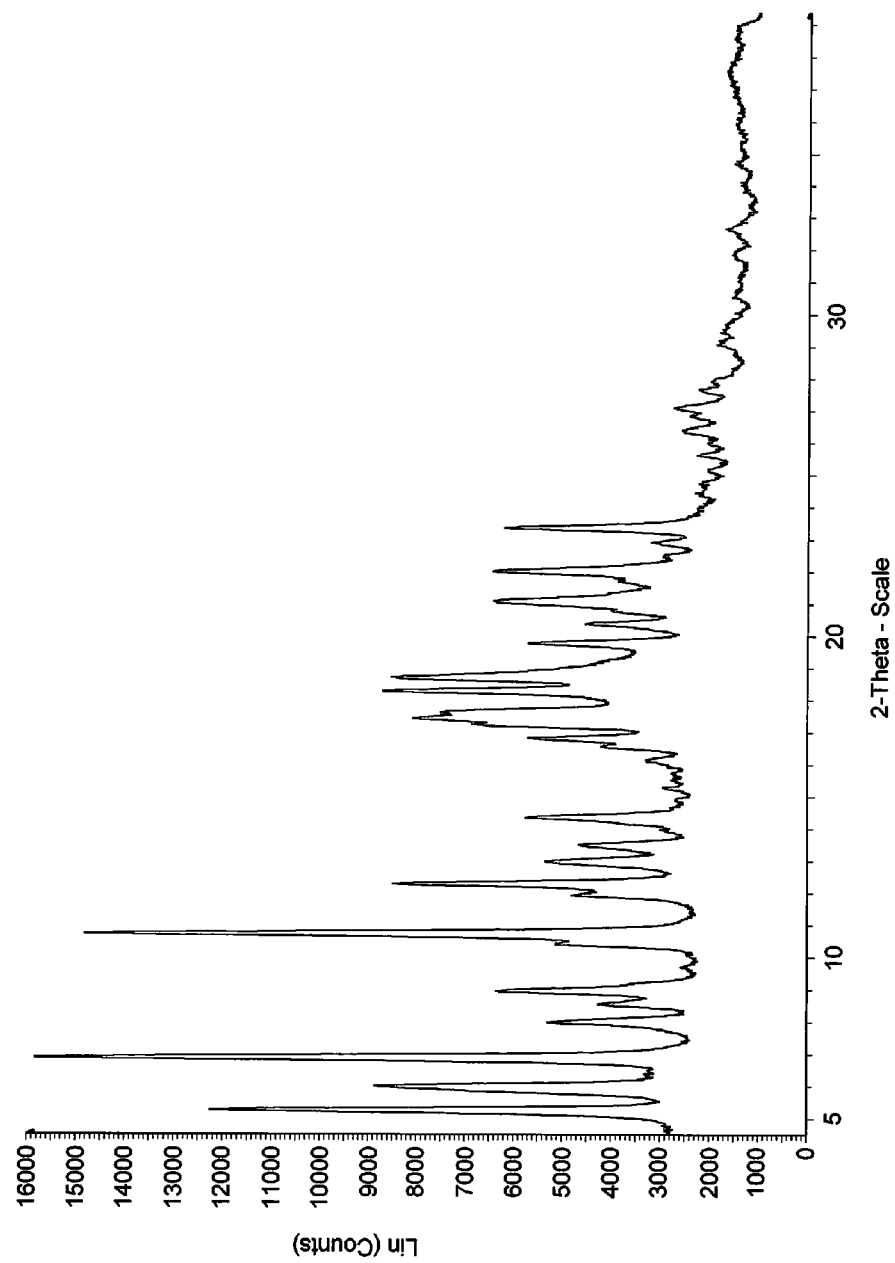
FIG. 20 is an XRPD pattern of Form M of Compound 1.

In another aspect, the invention provides a crystalline solvate Form M of Compound I, which has an XRPD pattern as depicted in FIG. 20. This crystalline solvate form is a methylethyl ketone (MEK) solvate, or a MEK/water 99/1 solvate.

In a further embodiment of this aspect, crystalline solvate Form M is characterized by one or more peaks selected from the group consisting of 5.2±0.2 degrees, 6.0±0.2 degrees, 6.9±0.2 degrees, 10.7±0.2 degrees, 12.3±0.2 degrees, 17.6±0.2 degrees, 18.3±0.2 degrees, and 21.1±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form M is characterized by a peak at 5.2±0.2 degrees, a peak at 6.0±0.2 degrees, a peak at 6.9±0.2 degrees, a peak at 10.7±0.2 degrees, a peak at 12.3±0.2 degrees, a peak at 17.6±0.2 degrees, a peak at 18.3±0.2 degrees, and a peak at 21.1±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form M is characterized by one or more peaks selected from the group consisting of 5.2±0.2 degrees, 6.0±0.2 degrees, 6.9±0.2 degrees, 8.0±0.2 degrees, 8.9±0.2 degrees, 10.7±0.2 degrees, 12.3±0.2 degrees, 13.0±0.2 degrees, 13.5±0.2 degrees, 14.4±0.2 degrees, 16.8±0.2 degrees, 17.3±0.2 degrees, 17.6±0.2 degrees, 18.3±0.2 degrees, 18.7±0.2 degrees, 19.8±0.2 degrees, 20.4±0.2 degrees, 21.1±0.2 degrees, 22.0±0.2 degrees, and 23.4±0.2 degrees, on a 2θ scale in an X-ray powder diffraction pattern. In a further embodiment, the X-ray powder diffraction pattern is obtained using Cu K alpha radiation.

In a further embodiment of this aspect, crystalline solvate Form M is characterized by a peak at 5.2±0.2 degrees, a peak at 6.0±0.2 degrees, a peak at 6.9±0.2 degrees, a peak at 8.0±0.2 degrees, a peak at 8.9±0.2 degrees, a peak at 10.7±0.2 degrees, a peak at 12.3±0.2 degrees, a peak at 13.0±0.2 degrees, a peak at 13.5±0.2 degrees, a peak at 14.4±0.2 degrees, a peak at 16.8±0.2 degrees, a peak at 17.3±0.2 degrees, a peak at 17.6±0.2 degrees, a peak at 18.3±0.2 degrees, a peak at 18.7±0.2 degrees, a peak at 19.8±0.2 degrees, a peak at 20.4±0.2 degrees, a peak at 21.1±0.2 degrees, a peak at 22.0±0.2 degrees, and a peak at 23.4±0.2 degrees, on a 2θ scale in an X-ray powder diffraction pattern. In a further embodiment, the X-ray powder diffraction pattern is obtained using Cu K alpha radiation.

Figure 21:
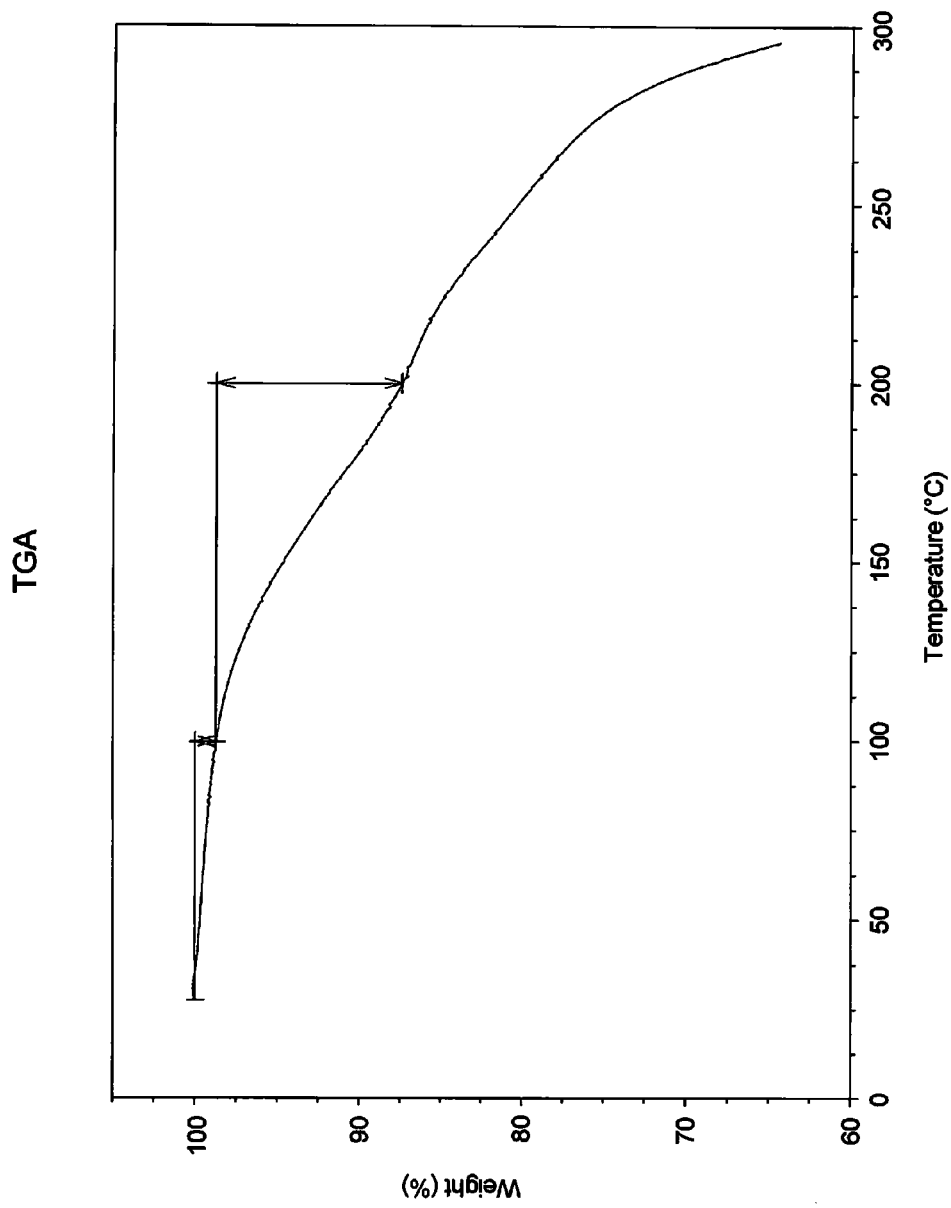
FIG. 21 is a thermogravimetric trace of Form M of Compound 1.

A thermogravimetric trace of Form M is provided as FIG. 21.

Figure 22:
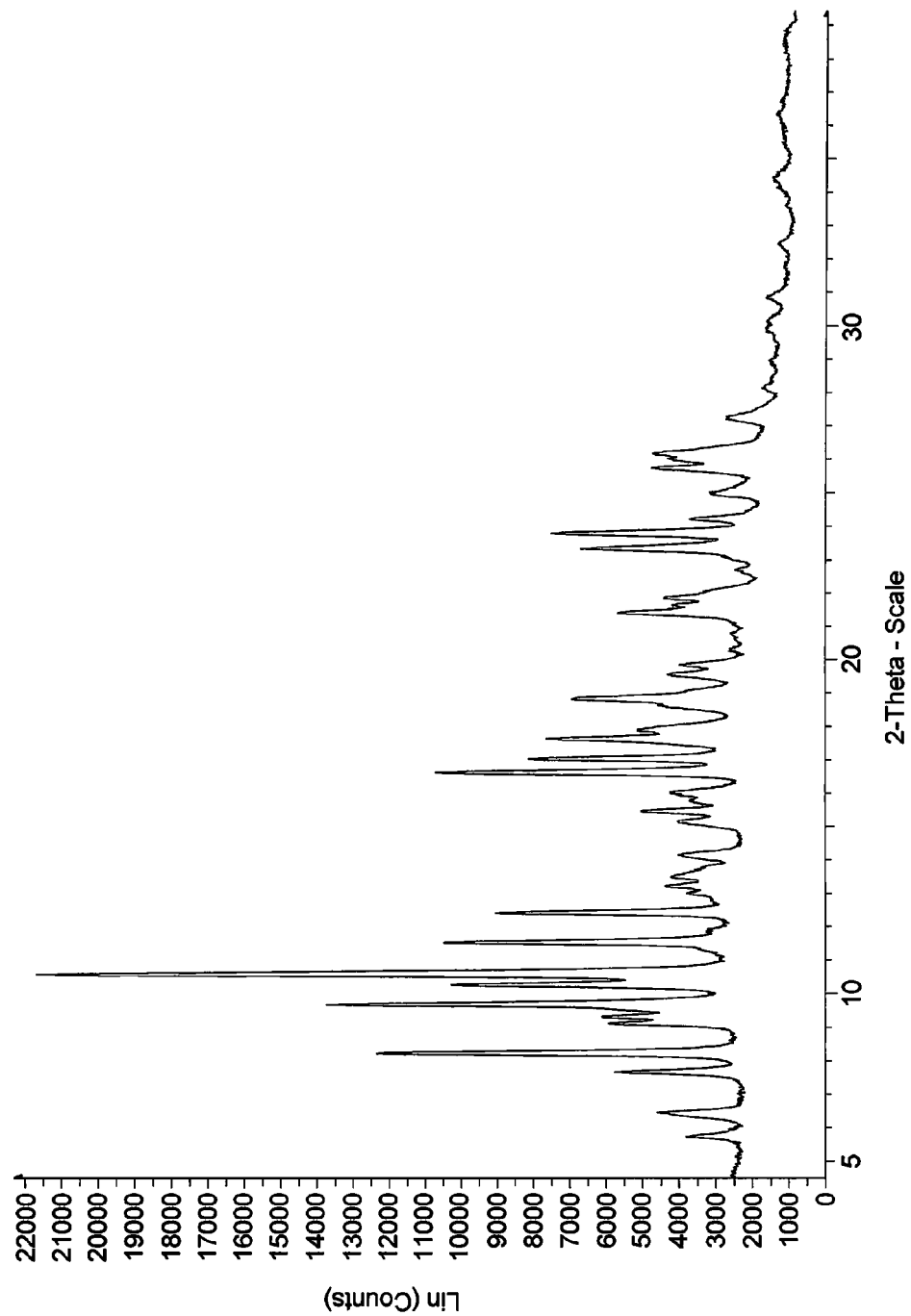
FIG. 22 is an XRPD pattern of Form N of Compound 1.

In another aspect, the invention provides a crystalline solvate Form N of Compound I, which has an XRPD pattern as depicted in FIG. 22. This crystalline solvate form is a MEK/water 90/10 solvate or a MEK/water 80/20 solvate.

In a further embodiment of this aspect, crystalline solvate Form N is characterized by one or more peaks selected from the group consisting of 8.2±0.2 degrees, 9.7±0.2 degrees, 10.6±0.2 degrees, 11.5±0.2 degrees, 12.4±0.2 degrees, 16.6±0.2 degrees, 17.6±0.2 degrees, and 23.8±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form N is characterized by a peak at 8.2±0.2 degrees, a peak at 9.7±0.2 degrees, a peak at 10.6±0.2 degrees, a peak at 11.5±0.2 degrees, a peak at 12.4±0.2 degrees, a peak at 16.6±0.2 degrees, a peak at 17.6±0.2 degrees, and a peak at 23.8±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form N is characterized by one or more peaks selected from the group consisting of 6.4±0.2 degrees, 7.6±0.2 degrees, 8.2±0.2 degrees, 9.1±0.2 degrees, 9.7±0.2 degrees, 10.2±0.2 degrees, 10.6±0.2 degrees, 11.5±0.2 degrees, 12.4±0.2 degrees, 14.1±0.2 degrees, 15.4±0.2 degrees, 16.6±0.2 degrees, 17.0±0.2 degrees, 17.6±0.2 degrees, 18.8±0.2 degrees, 21.4±0.2 degrees, 23.3±0.2 degrees, 23.8±0.2 degrees, 24.2±0.2 degrees, and 25.7±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form N is characterized by a peak at 6.4±0.2 degrees, a peak at 7.6±0.2 degrees, a peak at 8.2±0.2 degrees, a peak at 9.1±0.2 degrees, a peak at 9.7±0.2 degrees, a peak at 10.2±0.2 degrees, a peak at 10.6±0.2 degrees, a peak at 11.5±0.2 degrees, a peak at 12.4±0.2 degrees, a peak at 14.1±0.2 degrees, a peak at 15.4±0.2 degrees, a peak at 16.6±0.2 degrees, a peak at 17.0±0.2 degrees, a peak at 17.6±0.2 degrees, a peak at 18.8±0.2 degrees, a peak at 21.4±0.2 degrees, a peak at 23.3±0.2 degrees, a peak at 23.8±0.2 degrees, a peak at 24.2±0.2 degrees, and a peak at 25.7±0.2 degrees on a 2θ scale in an X-ray powder diffraction pattern. In a further embodiment, the X-ray powder diffraction pattern is obtained using Cu K alpha radiation.

Figure 23:
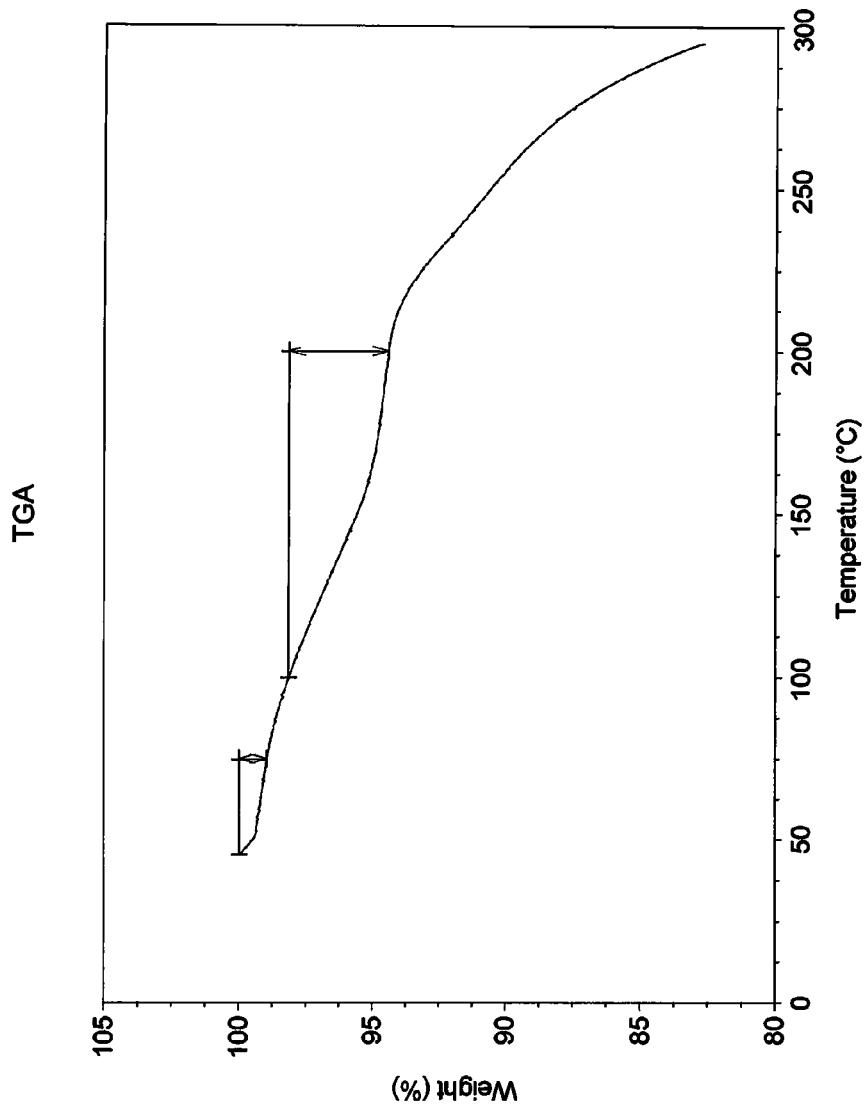
FIG. 23 is a thermogravimetric trace of Form N of Compound 1.

A thermogravimetric trace of Form N is provided as FIG. 23.

Figure 24:
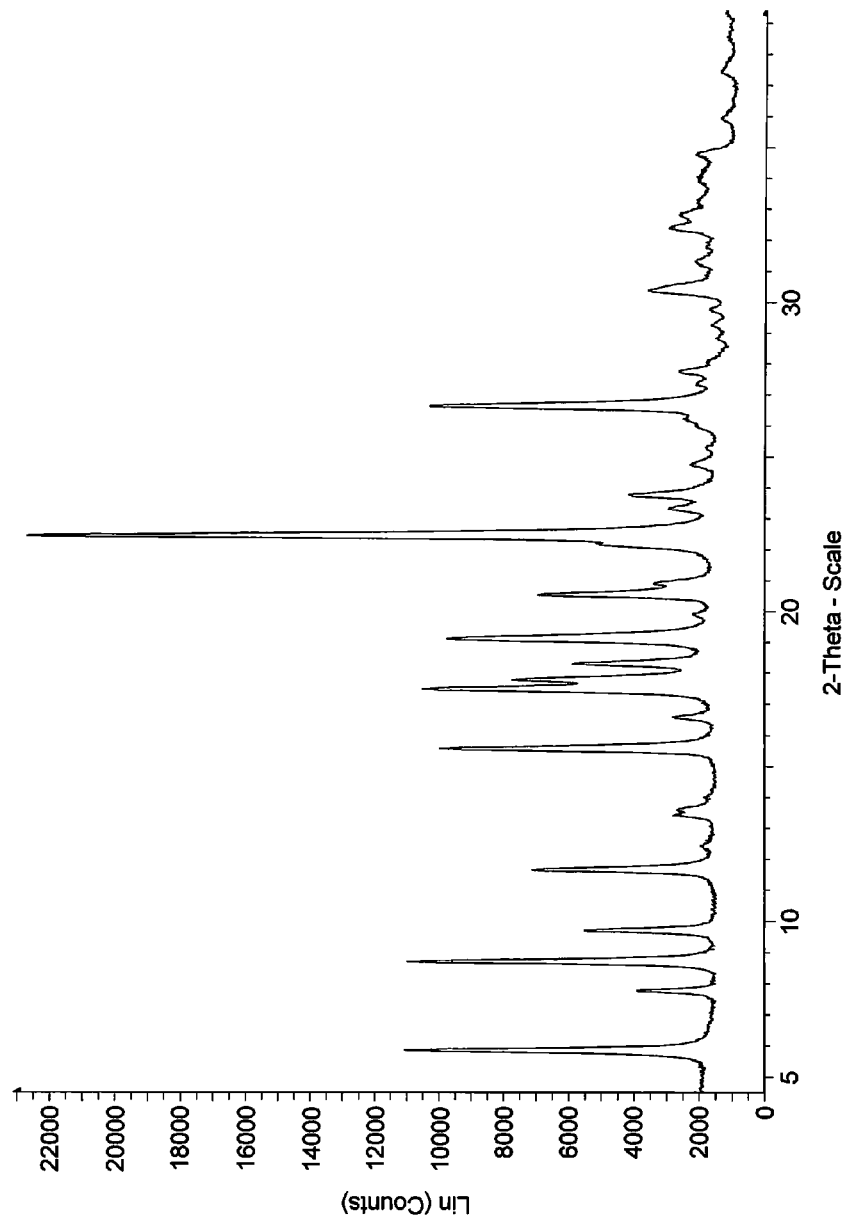
FIG. 24 is an XRPD pattern of Form O of Compound 1.

In another aspect, the invention provides a crystalline solvate Form O of Compound 1, which has an XRPD pattern as depicted in FIG. 24. This crystalline solvate form is a methylethyl ketone (MEK) solvate, or a MEK/water 99/1 solvate.

In a further embodiment of this aspect, crystalline solvate Form O is characterized by one or more peaks selected from the group consisting of 5.7±0.2 degrees, 8.5±0.2 degrees, 9.5±0.2 degrees, 11.4±0.2 degrees, 15.3±0.2 degrees, 17.2±0.2 degrees, 18.9±0.2 degrees, and 22.2±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form O is characterized by a peak at 5.7±0.2 degrees, a peak at 8.5±0.2 degrees, a peak at 9.5±0.2 degrees, a peak at 11.4±0.2 degrees, a peak at 15.3±0.2 degrees, a peak at 17.2±0.2 degrees, a peak at 18.9±0.2 degrees, and a peak at 22.2±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form O is characterized by one or more peaks selected from the group consisting of 5.7±0.2 degrees, 7.5±0.2 degrees, 8.5±0.2 degrees, 9.5±0.2 degrees, 11.4±0.2 degrees, 13.2±0.2 degrees, 15.3±0.2 degrees, 16.3±0.2 degrees, 17.2±0.2 degrees, 17.5±0.2 degrees, 18.0±0.2 degrees, 18.9±0.2 degrees, 20.3±0.2 degrees, 20.6±0.2 degrees, 22.2±0.2 degrees, 23.1±0.2 degrees, 23.5±0.2 degrees, and 26.4±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form O is characterized by a peak at 5.7±0.2 degrees, a peak at 7.5±0.2 degrees, a peak at 8.5±0.2 degrees, a peak at 9.5±0.2 degrees, a peak at 11.4±0.2 degrees, a peak at 13.2±0.2 degrees, a peak at 15.3±0.2 degrees, a peak at 16.3±0.2 degrees, a peak at 17.2±0.2 degrees, a peak at 17.5±0.2 degrees, a peak at 18.0±0.2 degrees, a peak at 18.9±0.2 degrees, a peak at 20.3±0.2 degrees, a peak at 20.6±0.2 degrees, a peak at 22.2±0.2 degrees, a peak at 23.1±0.2 degrees, a peak at 23.5±0.2 degrees, and a peak at 26.4±0.2 degrees on a 2θ scale in an X-ray powder diffraction pattern. In a further embodiment, the X-ray powder diffraction pattern is obtained using Cu K alpha radiation.

Figure 25:
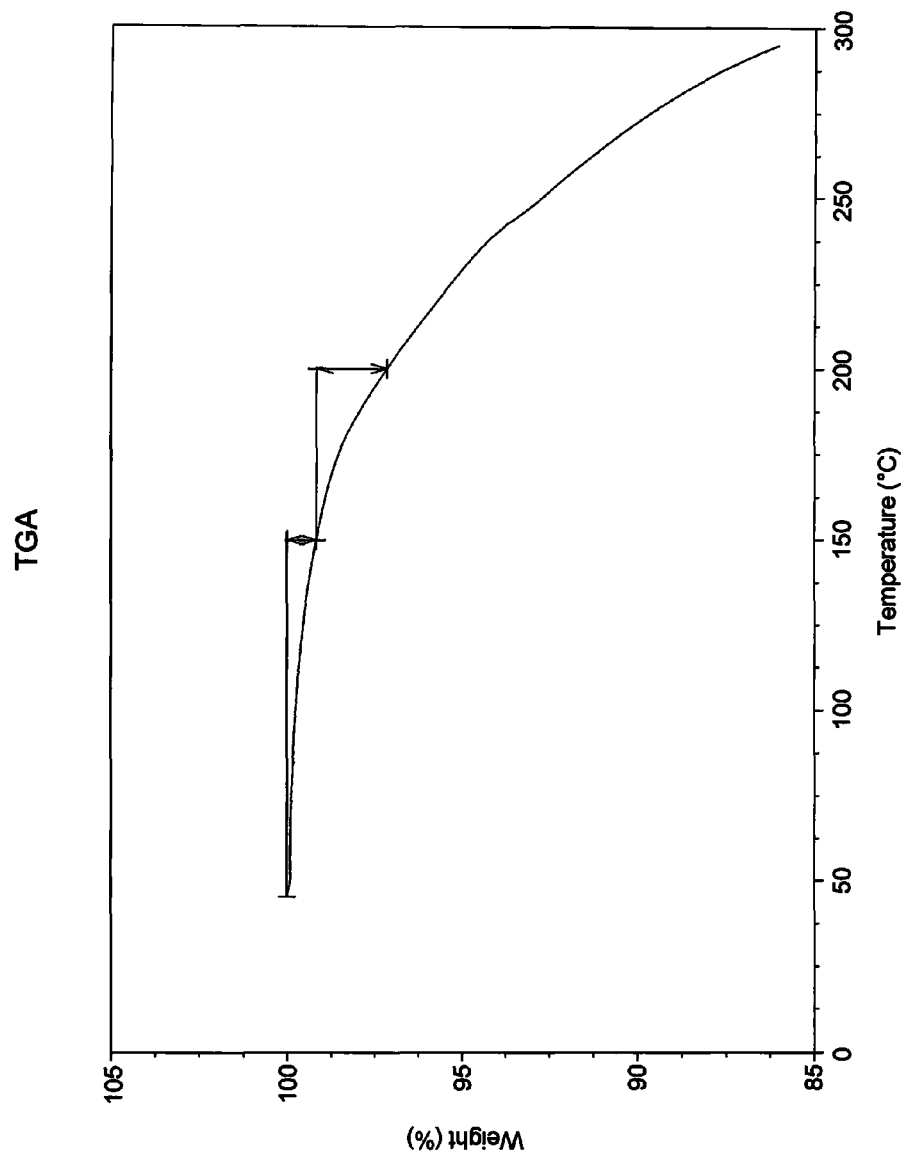
FIG. 25 is a thermogravimetric trace of Form O of Compound 1.

A thermogravimetric trace of Form O is provided as FIG. 25.

Figure 26:
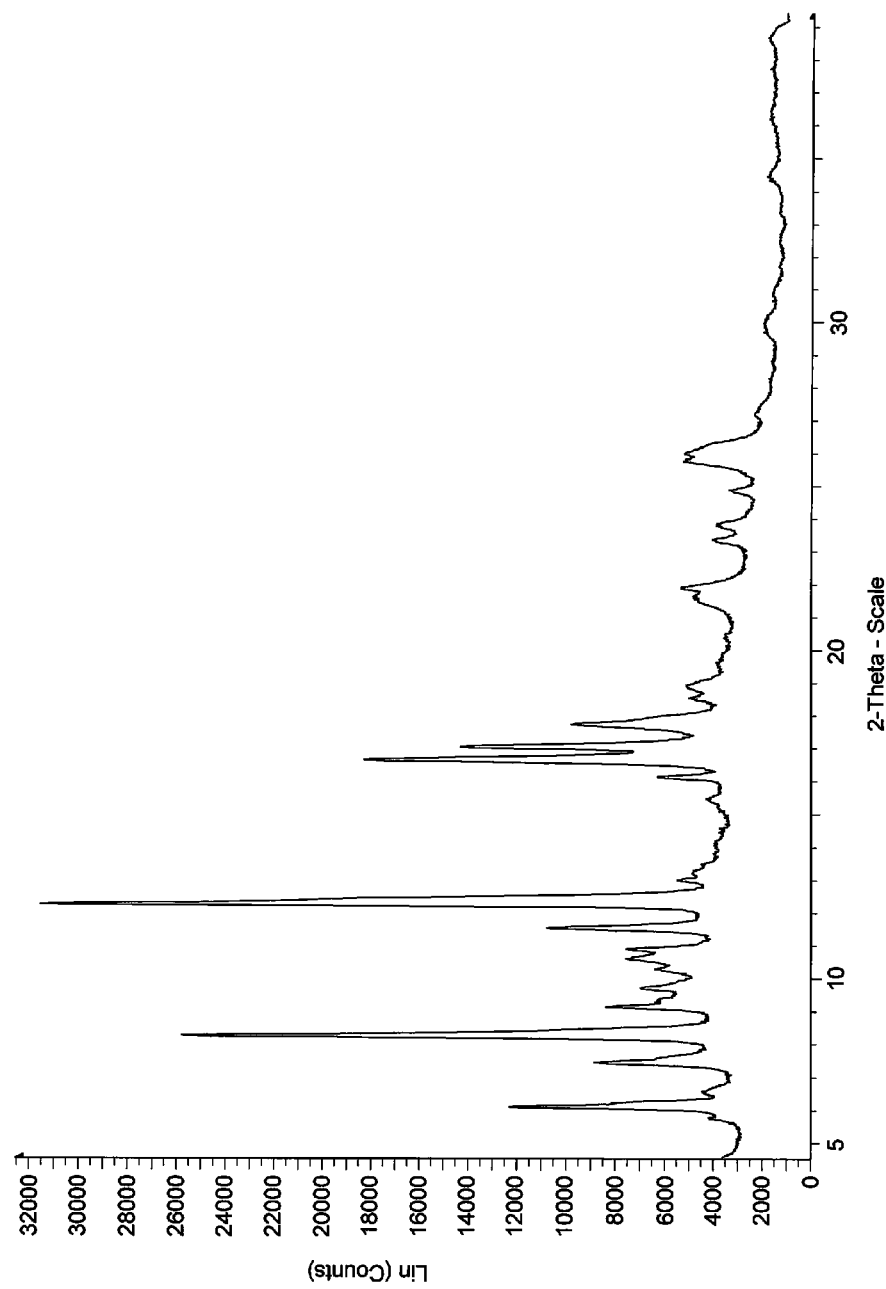
FIG. 26 is an XRPD pattern of Form P of Compound 1.

In another aspect, the invention provides a crystalline solvate Form P of Compound 1, which has an XRPD pattern as depicted in FIG. 26. This crystalline solvate form is a MEK/water 90/10 solvate or a MEK/water 80/20 solvate.

In a further embodiment of this aspect, crystalline solvate Form P is characterized by one or more peaks selected from the group consisting of 6.1±0.2 degrees, 7.4±0.2 degrees, 8.2±0.2 degrees, 9.1±0.2 degrees, 11.5±0.2 degrees, 12.3±0.2 degrees, 16.7±0.2 degrees, and 17.7±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form P is characterized by a peak at 6.1±0.2 degrees, a peak at 7.4±0.2 degrees, a peak at 8.2±0.2 degrees, a peak at 9.1±0.2 degrees, a peak at 11.5±0.2 degrees, a peak at 12.3±0.2 degrees, a peak at 16.7±0.2 degrees, and a peak at 17.7±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form P is characterized by one or more peaks selected from the group consisting of 6.1±0.2 degrees, 7.4±0.2 degrees, 8.2±0.2 degrees, 9.1±0.2 degrees, 9.7±0.2 degrees, 10.6±0.2 degrees, 10.9±0.2 degrees, 11.5±0.2 degrees, 12.3±0.2 degrees, 16.1±0.2 degrees, 16.7±0.2 degrees, 17.0±0.2 degrees, 17.7±0.2 degrees, 18.9±0.2 degrees, 21.9±0.2 degrees, 23.3±0.2 degrees, 23.8±0.2 degrees, 24.9±0.2 degrees, and 25.8±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form P is characterized by a peak at 6.1±0.2 degrees, a peak at 7.4±0.2 degrees, a peak at 8.2±0.2 degrees, a peak at 9.1±0.2 degrees, a peak at 9.7±0.2 degrees, a peak at 10.6±0.2 degrees, a peak at 10.9±0.2 degrees, a peak at 11.5±0.2 degrees, a peak at 12.3±0.2 degrees, a peak at 16.1±0.2 degrees, a peak at 16.7±0.2 degrees, a peak at 17.0±0.2 degrees, a peak at 17.7±0.2 degrees, a peak at 18.9±0.2 degrees, a peak at 21.9±0.2 degrees, a peak at 23.3±0.2 degrees, a peak at 23.8±0.2 degrees, a peak at 24.9±0.2 degrees, and a peak at 25.8±0.2 degrees on a 2θ scale in an X-ray powder diffraction pattern. In a further embodiment, the X-ray powder diffraction pattern is obtained using Cu K alpha radiation.

Figure 27:
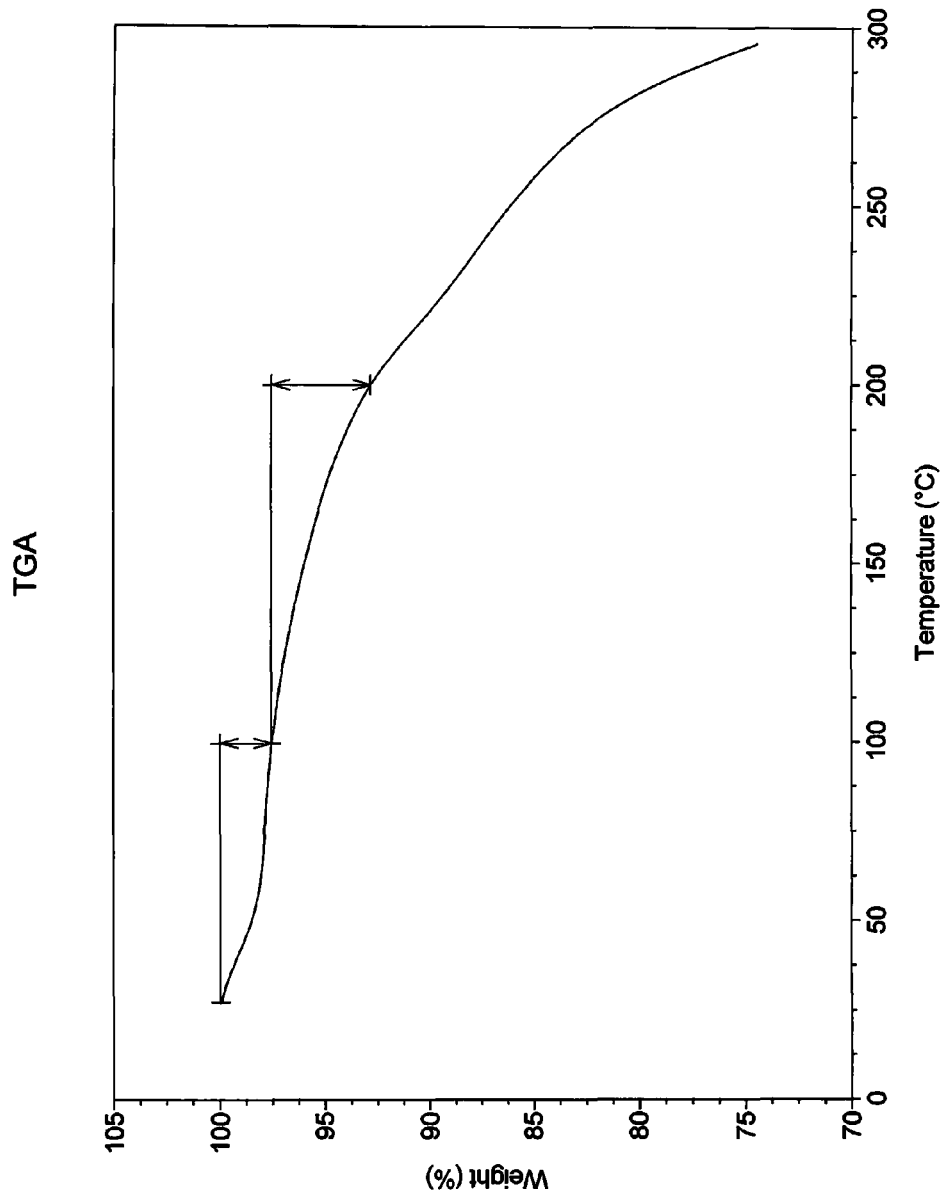
FIG. 27 is a thermogravimetric trace of Form P of Compound 1.

A thermogravimetric trace of Form P is provided as FIG. 27.

Figure 28:
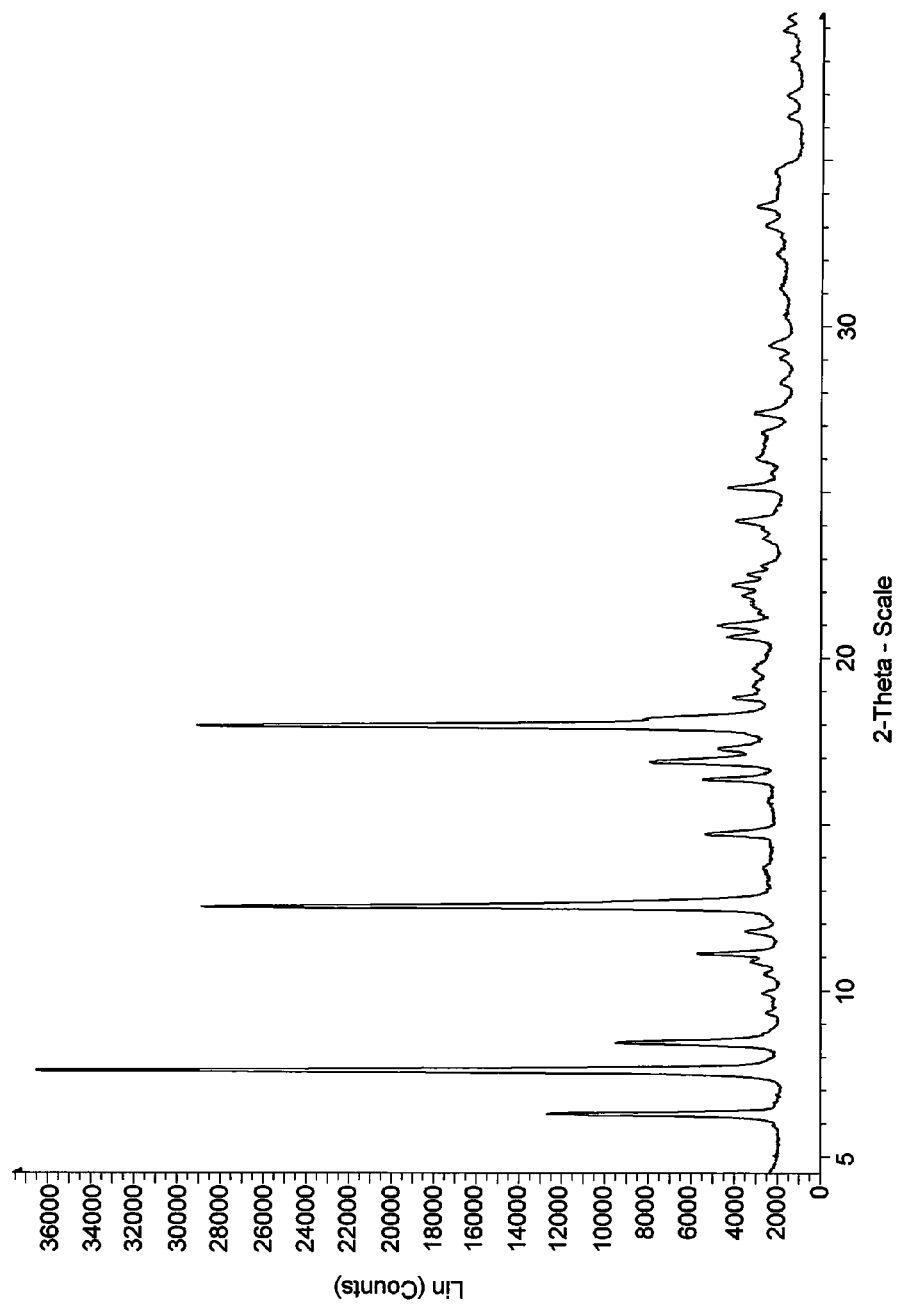
FIG. 28 is an XRPD pattern of Form Q of Compound 1.

In another aspect, the invention provides a crystalline solvate Form Q of Compound I, which has an XRPD pattern as depicted in FIG. 28. This crystalline solvate form is a MEK/water 80/20 solvate.

In one embodiment of this aspect, Form Q is characterized by one or more peaks selected from the group consisting of 6.3±0.2 degrees, 7.6±0.2 degrees, 8.4±0.2 degrees, 11.1±0.2 degrees, 12.5±0.2 degrees, 16.4±0.2 degrees, 16.9±0.2 degrees, and 18.0±0.2 degrees on a 2θ scale in an X-ray powder diffraction pattern. In a further embodiment, the X-ray powder diffraction pattern is obtained using Cu K alpha radiation.

In one embodiment of this aspect, Form Q is characterized by a peak at 6.3±0.2 degrees, a peak at 7.6±0.2 degrees, a peak at 8.4±0.2 degrees, a peak at 11.1±0.2 degrees, a peak at 12.5±0.2 degrees, a peak at 16.4±0.2 degrees, a peak at 16.9±0.2 degrees, and a peak at 18.0±0.2 degrees on a 2θ scale in an X-ray powder diffraction pattern. In a further embodiment, the X-ray powder diffraction pattern is obtained using Cu K alpha radiation.

In one embodiment of this aspect, Form Q is characterized by one or more peaks selected from the group consisting of 6.3±0.2 degrees, 7.6±0.2 degrees, 8.4±0.2 degrees, 11.1±0.2 degrees, 11.7±0.2 degrees, 12.5±0.2 degrees, 14.7±0.2 degrees, 16.4±0.2 degrees, 16.9±0.2 degrees, 17.3±0.2 degrees, 18.0±0.2 degrees, 18.8±0.2 degrees, 20.6±0.2 degrees, 21.0±0.2 degrees, 22.2±0.2 degrees, 24.1±0.2 degrees, 25.1±0.2 degrees, and 27.4±0.2 degrees on a 2θ scale in an X-ray powder diffraction pattern. In a further embodiment, the X-ray powder diffraction pattern is obtained using Cu K alpha radiation.

In one embodiment of this aspect, Form Q is characterized by a peak at 6.3±0.2 degrees, a peak at 7.6±0.2 degrees, a peak at 8.4±0.2 degrees, a peak at 11.1±0.2 degrees, a peak at 11.7±0.2 degrees, a peak at 12.5±0.2 degrees, a peak at 14.7±0.2 degrees, a peak at 16.4±0.2 degrees, a peak at 16.9±0.2 degrees, a peak at 17.3±0.2 degrees, a peak at 18.0±0.2 degrees, a peak at 18.8±0.2 degrees, a peak at 20.6±0.2 degrees, a peak at 21.0±0.2 degrees, a peak at 22.2±0.2 degrees, a peak at 24.1±0.2 degrees, a peak at 25.1±0.2 degrees, and a peak at 27.4±0.2 degrees on a 2θ scale in an X-ray powder diffraction pattern. In a further embodiment, the X-ray powder diffraction pattern is obtained using Cu K alpha radiation.

Figure 29:
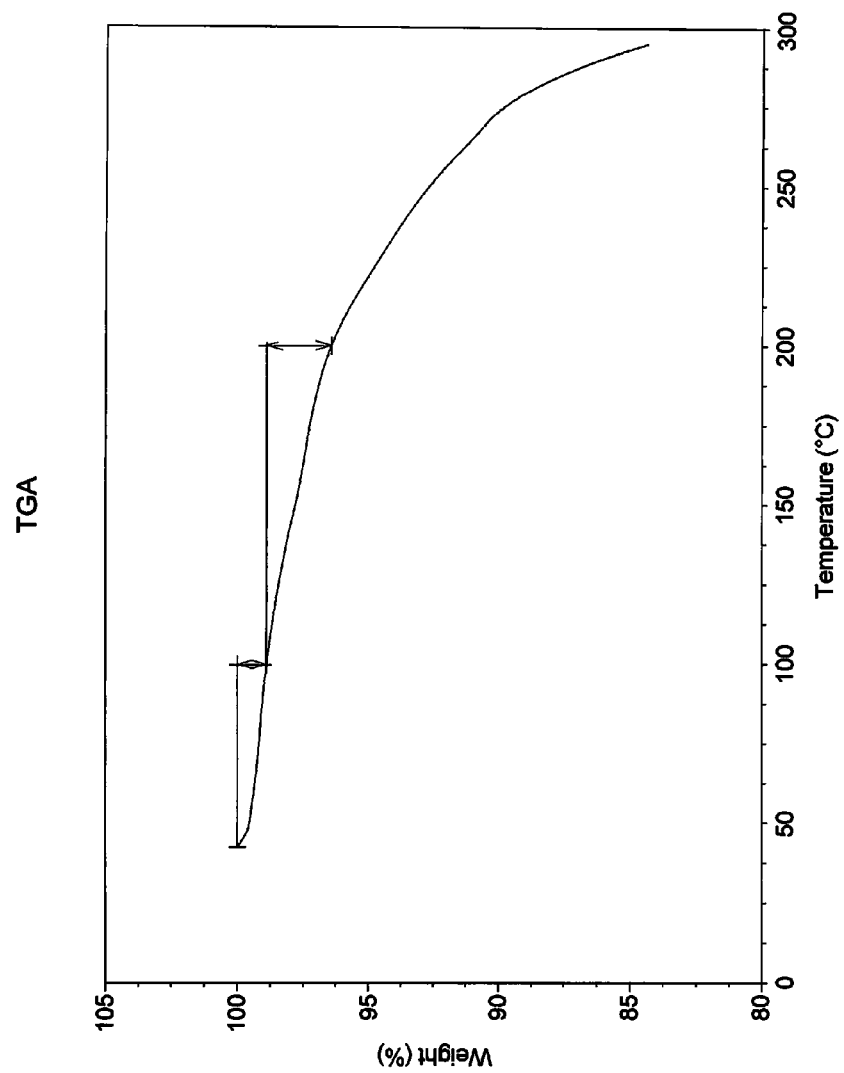
FIG. 29 is a thermogravimetric trace of Form Q of Compound 1.

A thermogravimetric trace of Form Q is provided as FIG. 29.

Figure 30:
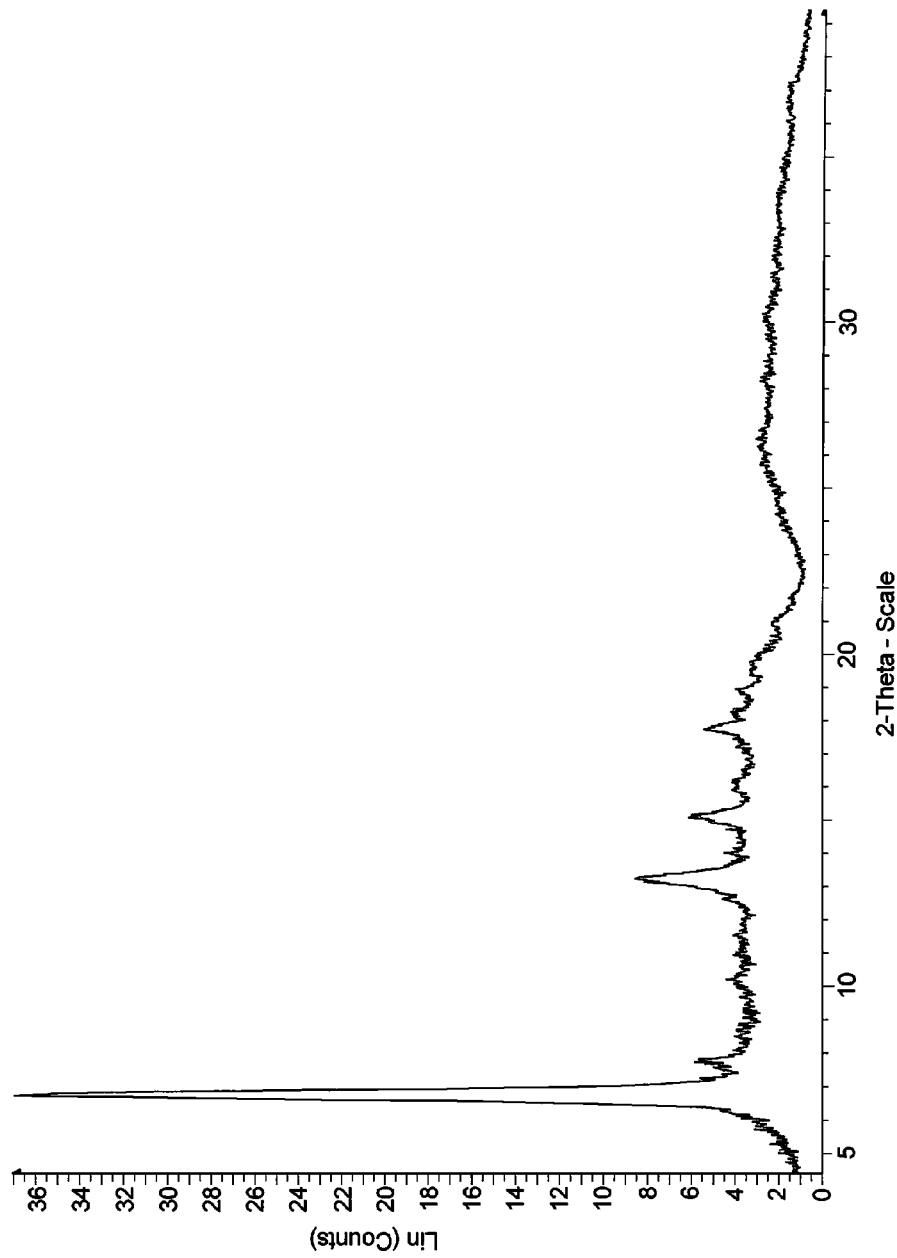
FIG. 30 is an XRPD pattern of Form R of Compound 1.

In another aspect, the invention provides a crystalline solvate Form R of Compound 1, which has an XRPD pattern as depicted in FIG. 30. This crystalline form is an acetonitrile solvate.

In a further embodiment of this aspect, crystalline solvate Form R is characterized by one or more peaks selected from the group consisting of 6.7±0.2 degrees, 7.7±0.2 degrees, 13.2±0.2 degrees, 15.1±0.2 degrees, and 17.8±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form R is characterized by a peak at 6.7±0.2 degrees, a peak at 7.7±0.2 degrees, a peak at 13.2±0.2 degrees, a peak at 15.1±0.2 degrees, and a peak at 17.8±0.2 degrees on a 2θ scale in an X-ray powder diffraction pattern. In a further embodiment, the X-ray powder diffraction pattern is obtained using Cu K alpha radiation.

Figure 31:
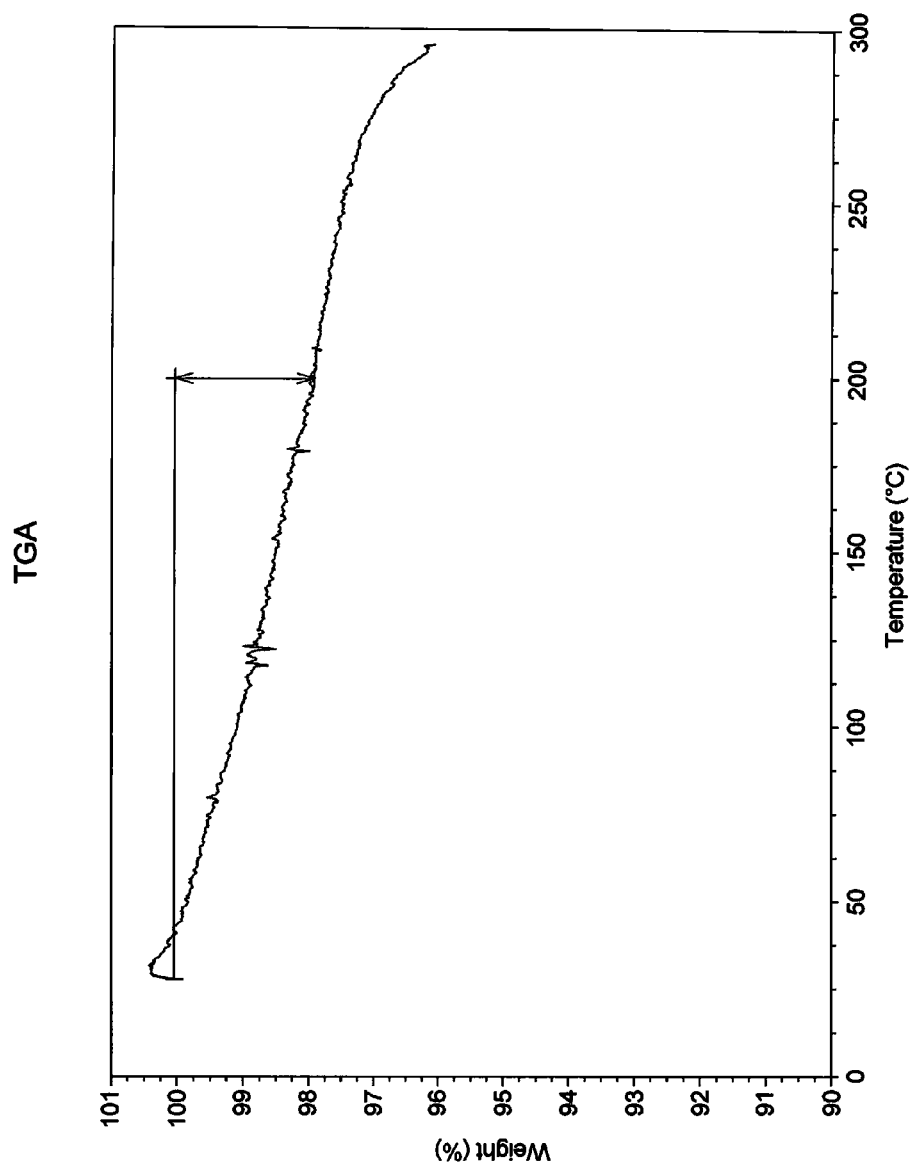
FIG. 31 is a thermogravimetric trace of Form R of Compound 1.

A thermogravimetric trace of Form R is provided as FIG. 31.

Figure 32:
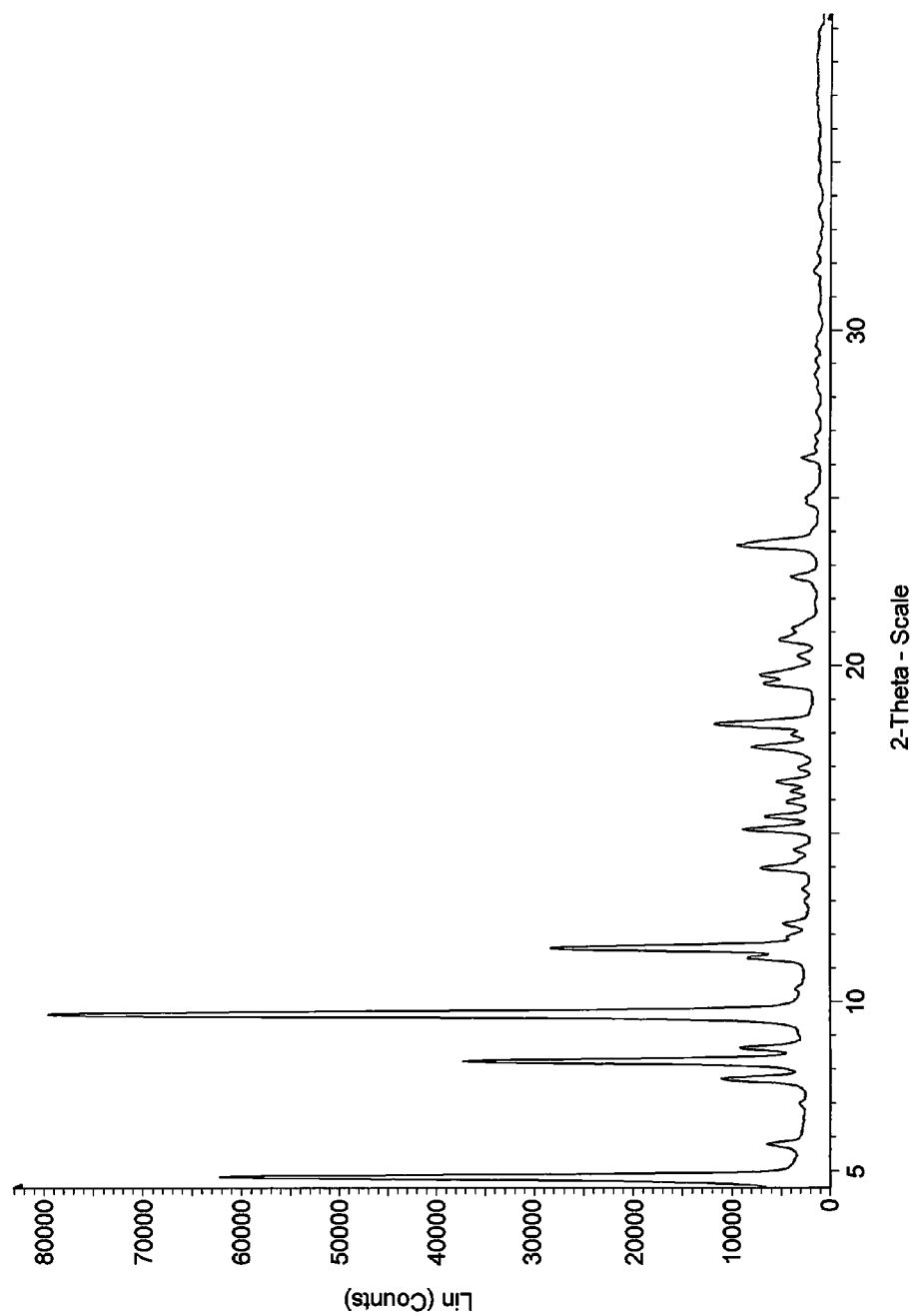
FIG. 32 is an XRPD pattern of Form S of Compound 1.

In another aspect, the invention provides a crystalline solvate Form S of Compound 1, which has an XRPD pattern as depicted in FIG. 32. This crystalline solvate form is a MEK/water 80/20 solvate.

In a further embodiment of this aspect, crystalline solvate Form S is characterized by one or more peaks selected from the group consisting of 4.8±0.2 degrees, 7.7±0.2 degrees, 8.2±0.2 degrees, 9.6±0.2 degrees, 11.6±0.2 degrees, 15.1±0.2 degrees, 18.3±0.2 degrees, and 23.6±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form S is characterized by a peak at 4.8±0.2 degrees, a peak at 7.7±0.2 degrees, a peak at 8.2±0.2 degrees, a peak at 9.6±0.2 degrees, a peak at 11.6±0.2 degrees, a peak at 15.1±0.2 degrees, a peak at 18.3±0.2 degrees, and a peak at 23.6±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form S is characterized by one or more peaks selected from the group consisting of 4.8±0.2 degrees, 5.7±0.2 degrees, 7.7±0.2 degrees, 8.2±0.2 degrees, 8.6±0.2 degrees, 9.6±0.2 degrees, 11.3±0.2 degrees, 11.6±0.2 degrees, 12.3±0.2 degrees, 13.9±0.2 degrees, 15.1±0.2 degrees, 15.5±0.2 degrees, 15.9±0.2 degrees, 16.5±0.2 degrees, 17.6±0.2 degrees, 18.3±0.2 degrees, 19.4±0.2 degrees, 19.7±0.2 degrees, 20.7±0.2 degrees, and 23.6±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form S is characterized by a peak at 4.8±0.2 degrees, a peak at 5.7±0.2 degrees, a peak at 7.7±0.2 degrees, a peak at 8.2±0.2 degrees, a peak at 8.6±0.2 degrees, a peak at 9.6±0.2 degrees, a peak at 11.3±0.2 degrees, a peak at 11.6±0.2 degrees, a peak at 12.3±0.2 degrees, a peak at 13.9±0.2 degrees, a peak at 15.1±0.2 degrees, a peak at 15.5±0.2 degrees, a peak at 15.9±0.2 degrees, a peak at 16.5±0.2 degrees, a peak at 17.6±0.2 degrees, a peak at 18.3±0.2 degrees, a peak at 19.4±0.2 degrees, a peak at 19.7±0.2 degrees, a peak at 20.7±0.2 degrees, and a peak at 23.6±0.2 degrees on a 2θ scale in an X-ray powder diffraction pattern. In a further embodiment, the X-ray powder diffraction pattern is obtained using Cu K alpha radiation.

Figure 33:
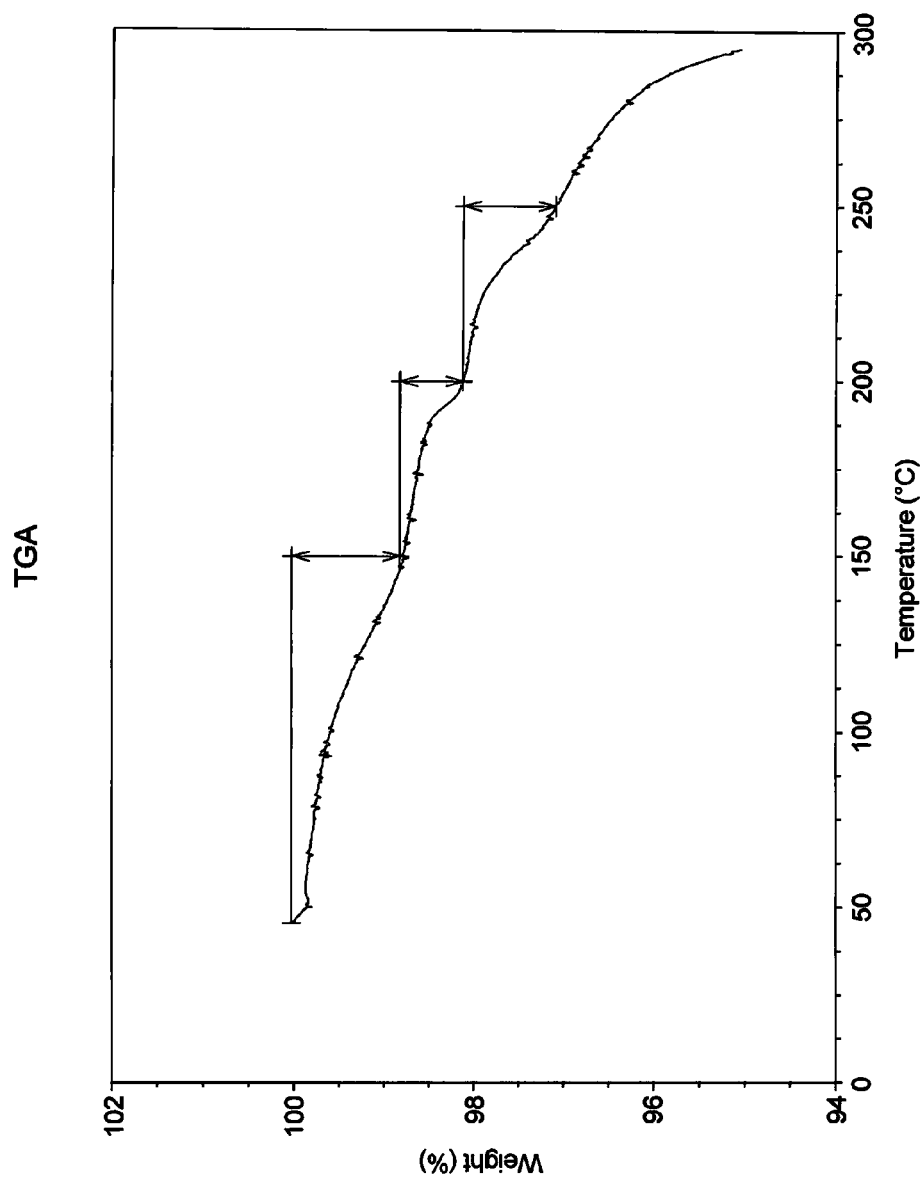
FIG. 33 is a thermogravimetric trace of Form S of Compound 1.

A thermogravimetric trace of Form S is provided as FIG. 33.

Figure 34:
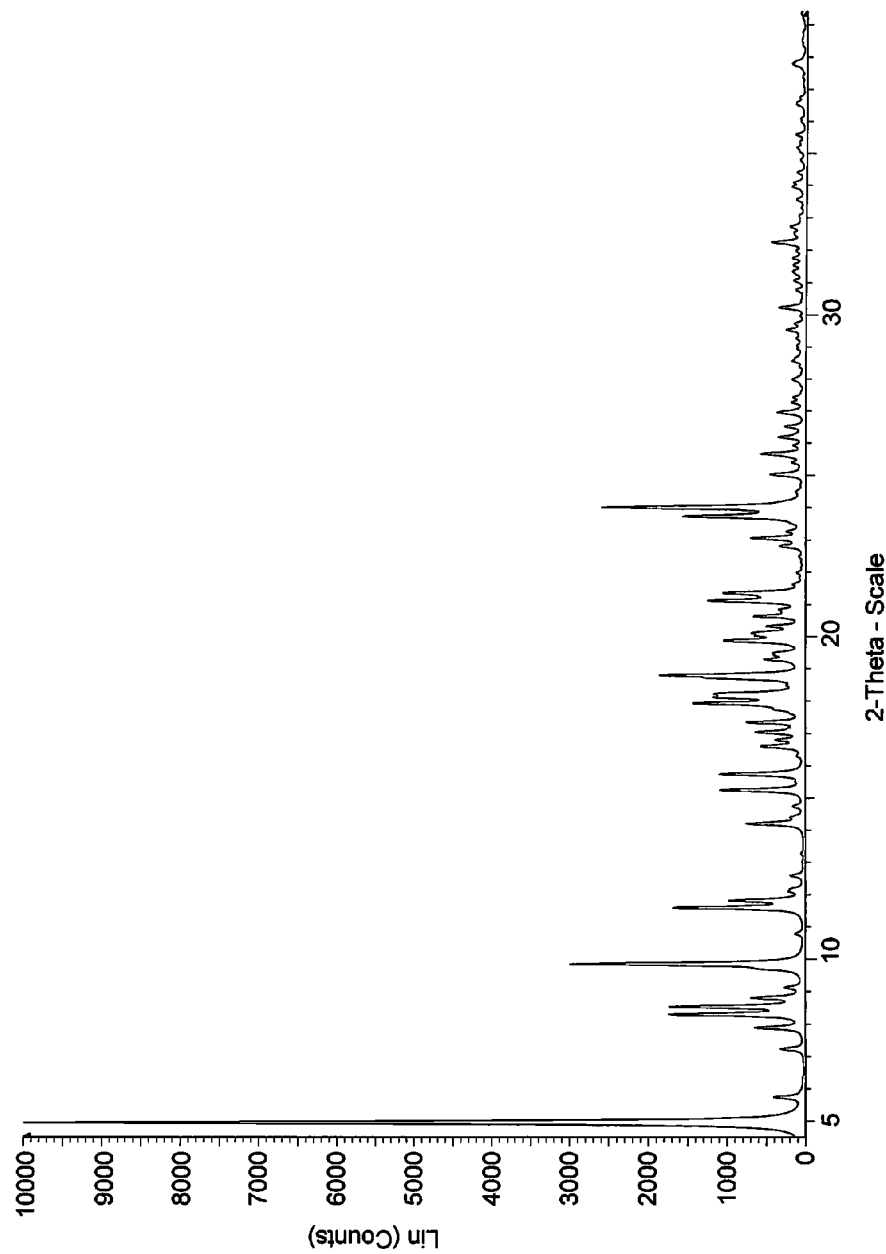
FIG. 34 is an XRPD pattern of Form T of Compound 1.

In another aspect, the invention provides a crystalline solvate Form T of Compound 1, which has an XRPD pattern as depicted in FIG. 34. This crystalline solvate form is an isopropyl acetate/water 95/5 solvate.

In a further embodiment of this aspect, crystalline solvate Form T is characterized by one or more peaks selected from the group consisting of 4.9±0.2 degrees, 8.3±0.2 degrees, 9.8±0.2 degrees, 11.6±0.2 degrees, 18.1±0.2 degrees, 18.7±0.2 degrees, 21.1±0.2 degrees, and 24.0±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form T is characterized by a peak at 4.9±0.2 degrees, a peak at 8.3±0.2 degrees, a peak at 9.8±0.2 degrees, a peak at 11.6±0.2 degrees, a peak at 18.1±0.2 degrees, a peak at 18.7±0.2 degrees, a peak at 21.1±0.2 degrees, and a peak at 24.0±0.2 degrees on a 2θ scale in an X-ray powder diffraction pattern. In a further embodiment, the X-ray powder diffraction pattern is obtained using Cu K alpha radiation ($\lambda=1.5418$ Å).

In a further embodiment of this aspect, crystalline solvate Form T is characterized by one or more peaks selected from the group consisting of 4.9±0.2 degrees, 7.8±0.2 degrees, 8.3±0.2 degrees, 8.5±0.2 degrees, 9.8±0.2 degrees, 11.6±0.2 degrees, 14.2±0.2 degrees, 15.2±0.2 degrees, 15.7±0.2 degrees, 17.3±0.2 degrees, 18.1±0.2 degrees, 18.7±0.2 degrees, 19.9±0.2 degrees, 21.1±0.2 degrees, 21.3±0.2 degrees, 23.0±0.2 degrees, 23.7±0.2 degrees, 24.0±0.2 degrees, 25.0±0.2 degrees, and 25.6±0.2 degrees on a 2θ scale in an X-ray powder diffraction pattern. In a further embodiment, the X-ray powder diffraction pattern is obtained using Cu K alpha radiation.

In a further embodiment of this aspect, crystalline solvate Form T is characterized by a peak at 4.9±0.2 degrees, a peak at 7.8±0.2 degrees, a peak at 8.3±0.2 degrees, a peak at 8.5±0.2 degrees, a peak at 9.8±0.2 degrees, a peak at 11.6±0.2 degrees, a peak at 14.2±0.2 degrees, a peak at 15.2±0.2 degrees, a peak at 15.7±0.2 degrees, a peak at 17.3±0.2 degrees, a peak at 18.1±0.2 degrees, a peak at 18.7±0.2 degrees, a peak at 19.9±0.2 degrees, a peak at 21.1±0.2 degrees, a peak at 21.3±0.2 degrees, a peak at 23.0±0.2 degrees, a peak at 23.7±0.2 degrees, a peak at 24.0±0.2 degrees, a peak at 25.0±0.2 degrees, and a peak at 25.6±0.2 degrees on a 2θ scale in an X-ray powder diffraction pattern. In a further embodiment, the X-ray powder diffraction pattern is obtained using Cu K alpha radiation.

Figure 35:
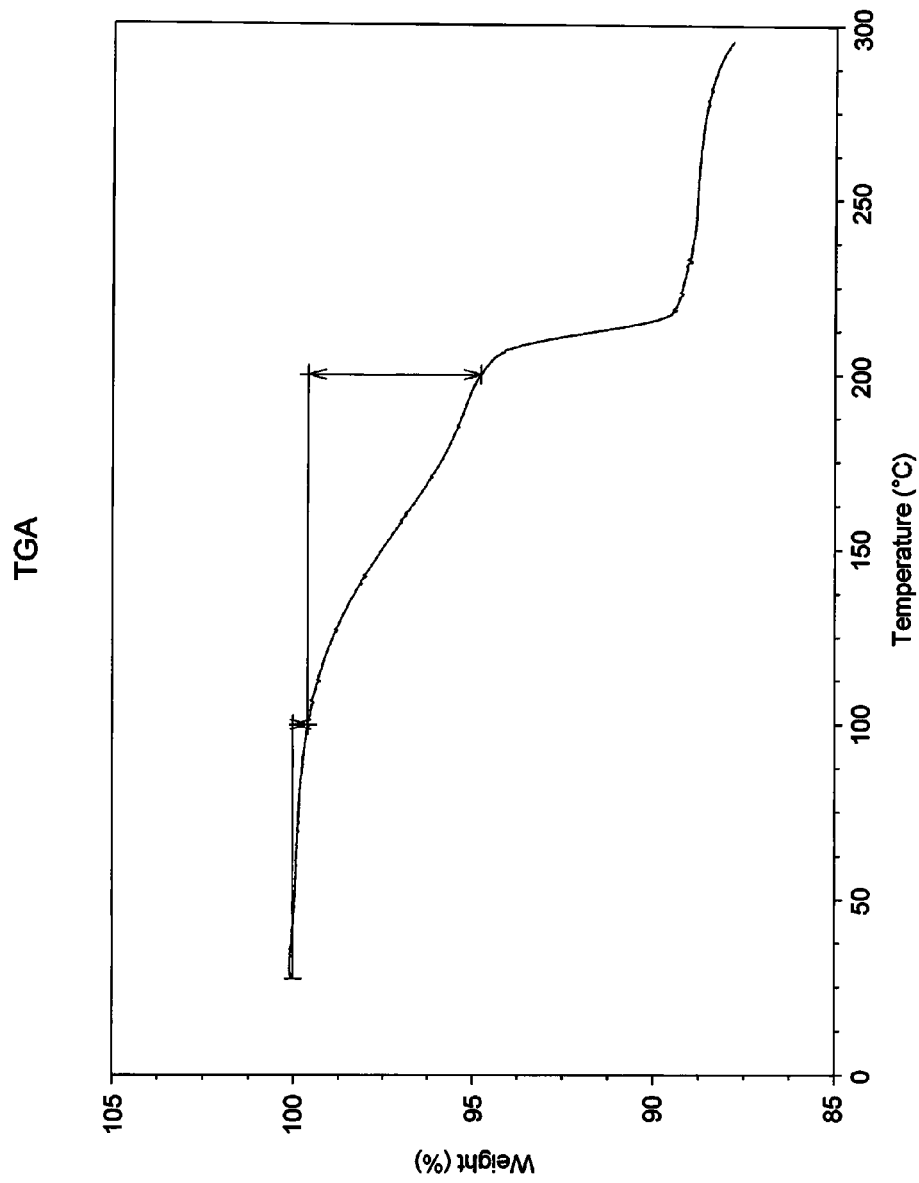
FIG. 35 is a thermogravimetric trace of Form T of Compound 1.

A thermogravimetric trace of Form T is provided as FIG. 35.

A single crystal was obtained for Form T, which has the following unit cell dimensions:

Space Group: C2/c

Cell Lengths: a=32.5478(13), b=22.5036(9), c=22.5540(9)

Cell Angles: α=90.00, β32 112.725(2), γ=90.00

Cell Volume: 15237.1 Å

Figure 36:
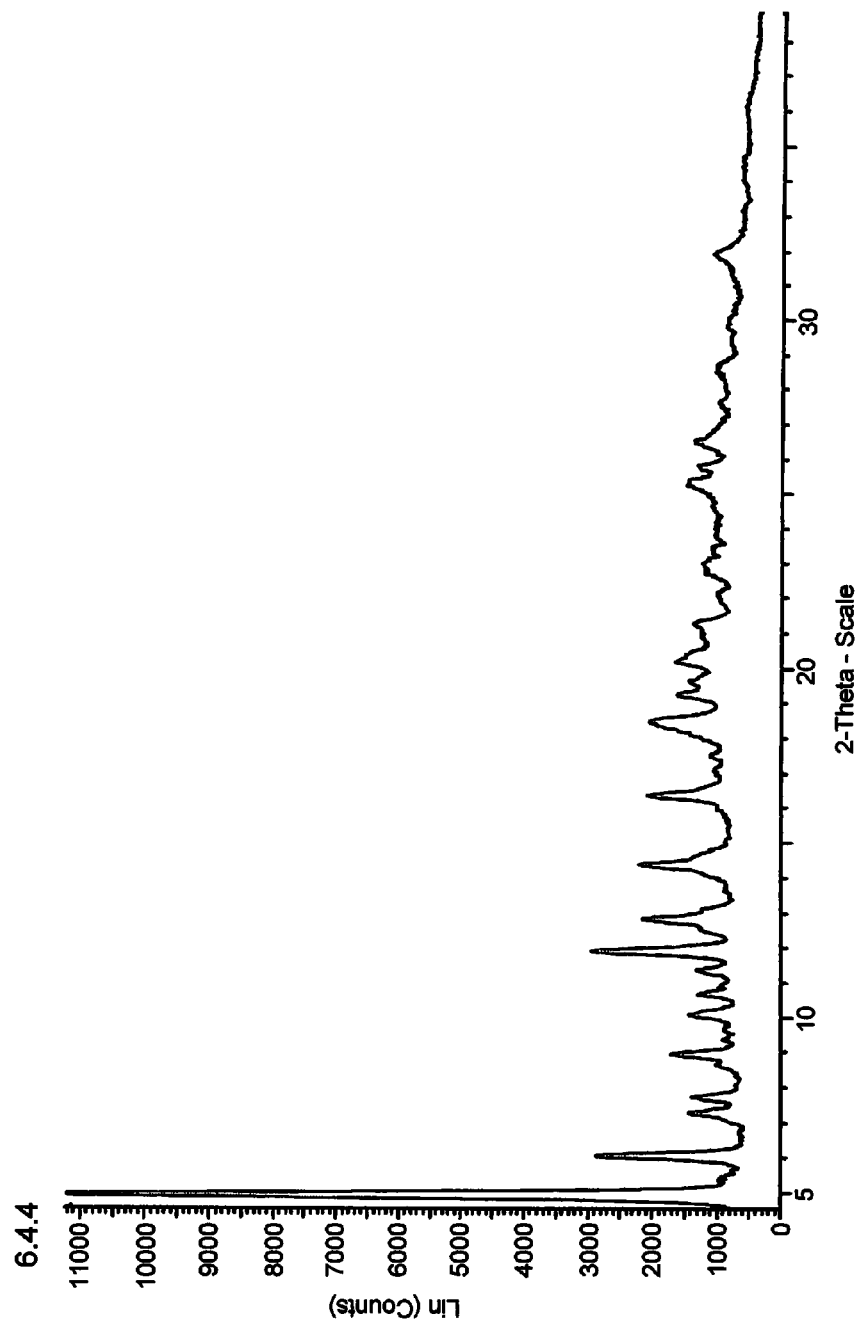
FIG. 36 is an XRPD pattern of Hydrate B of Compound 1.

In another aspect, the invention provides a crystalline solvate of Compound 1 designated as Hydrate B, which has an XRPD pattern as depicted in FIG. 36.

In a further embodiment of this aspect, Hydrate B is characterized by one or more peaks selected from the group consisting of 4.9±0.2 degrees, 6.0±0.2 degrees, 7.2±0.2 degrees, 8.9±0.2 degrees, 10.1±0.2 degrees, 10.7±0.2 degrees, 11.3±0.2 degrees, and 11.9±0.2 degrees on a 2θ scale in an X-ray powder diffraction pattern. In a further embodiment, the X-ray powder diffraction pattern is obtained using Cu K alpha radiation.

In a further embodiment of this aspect, Hydrate B is characterized by a peak at 4.9±0.2 degrees, a peak at 6.0±0.2 degrees, a peak at 7.2±0.2 degrees, a peak at 8.9±0.2 degrees, a peak at 10.1±0.2 degrees, a peak at 10.7±0.2 degrees, a peak at 11.3±0.2 degrees, and a peak at 11.9±0.2 degrees on a 2θ scale in an X-ray powder diffraction pattern. In a further embodiment, the X-ray powder diffraction pattern is obtained using Cu K alpha radiation.

Figure 37:
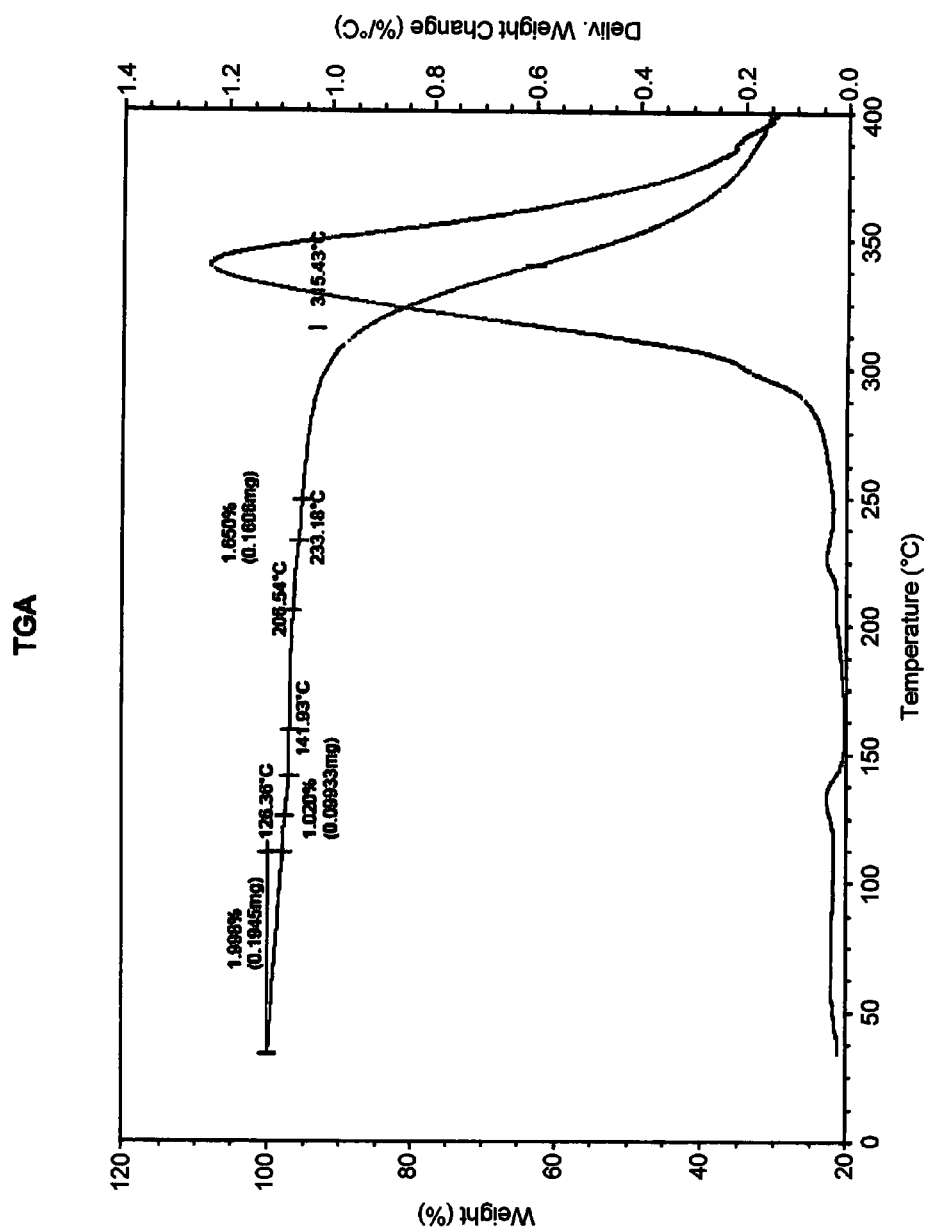
FIG. 37 is a thermogravimetric trace of Hydrate B of Compound 1.

A thermogravimetric trace of Hydrate B is provided as FIG. 37.

Figure 38:
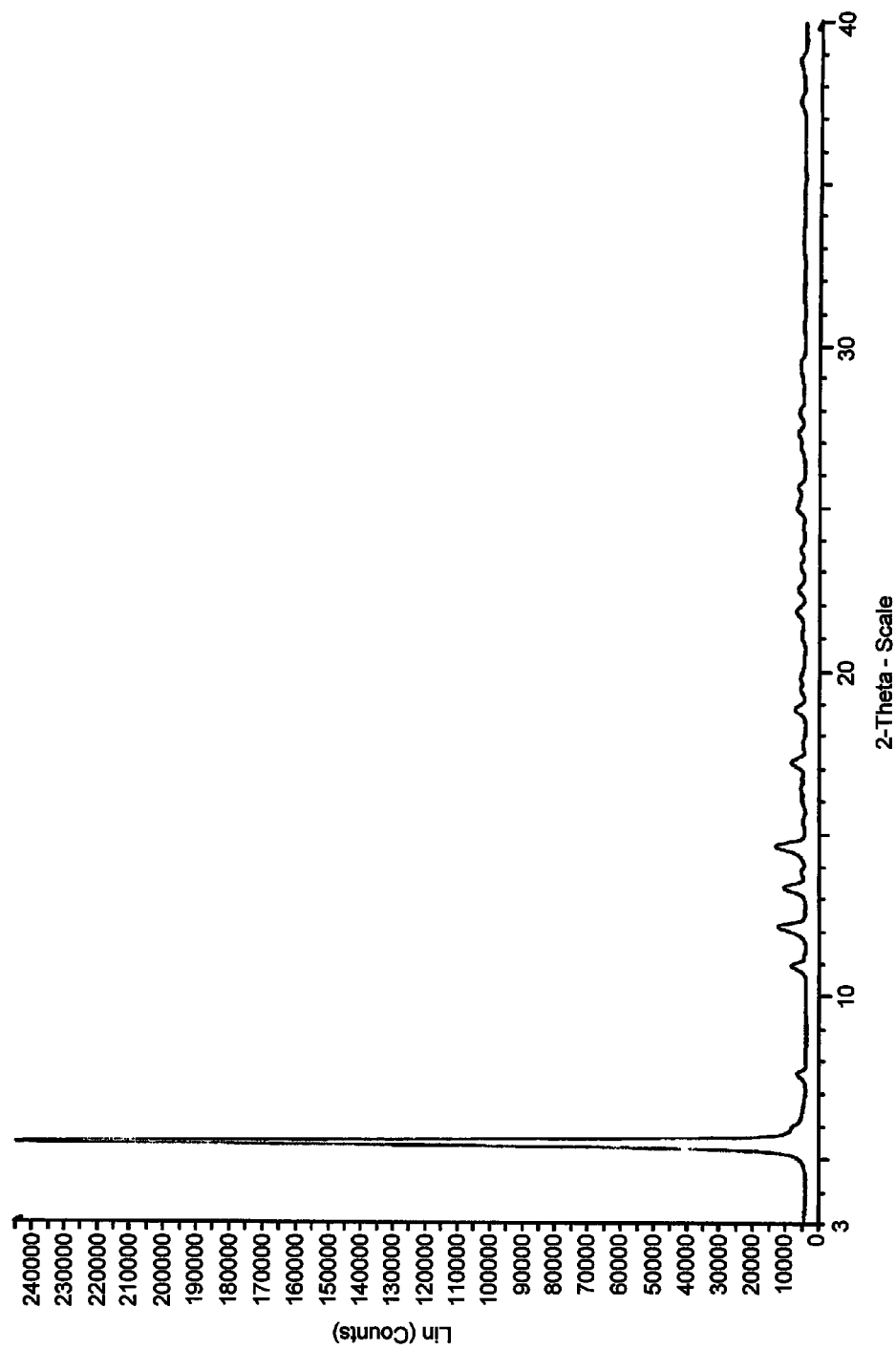
FIG. 38 is an XRPD pattern of Form W of Compound 1.

In another aspect, the invention provides a crystalline solvate of Compound 1 designated as Form W, which has an XRPD pattern as depicted in FIG. 38.

In a further embodiment of this aspect, Form W is characterized by one or more peaks selected from the group consisting of 5.5±0.2 degrees, 10.9±0.2 degrees, 12.1±0.2 degrees, 13.3±0.2 degrees, 14.6±0.2 degrees, 17.2±0.2 degrees, 18.8±0.2 degrees, and 21.8±0.2 degrees on a 2θ scale in an X-ray powder diffraction pattern. In a further embodiment, the X-ray powder diffraction pattern is obtained using Cu K alpha radiation.

In a further embodiment of this aspect, Form W is characterized by a peak at 5.5±0.2 degrees, a peak at 10.9±0.2 degrees, a peak at 12.1±0.2 degrees, a peak at 13.3±0.2 degrees, a peak at 14.6±0.2 degrees, a peak at 17.2±0.2 degrees, a peak at 18.8±0.2 degrees, and a peak at 21.8±0.2 degrees on a 2θ scale in an X-ray powder diffraction pattern. In a further embodiment, the X-ray powder diffraction pattern is obtained using Cu K alpha radiation.

In a further embodiment of this aspect, Form W is characterized by one or more peaks selected from the group consisting of 5.5±0.2 degrees, 5.9±0.2 degrees, 7.6±0.2 degrees, 10.9±0.2 degrees, 12.1±0.2 degrees, 13.3±0.2 degrees, 14.6±0.2 degrees, 17.2±0.2 degrees, 18.8±0.2 degrees, 21.8±0.2 degrees, 22.5±0.2 degrees, 23.2±0.2 degrees, 23.7±0.2 degrees, 25.0±0.2 degrees, and 25.6±0.2 degrees on a 2θ scale in an X-ray powder diffraction pattern. In a further embodiment, the X-ray powder diffraction pattern is obtained using Cu K alpha radiation.

In a further embodiment of this aspect, Form W is characterized by a peak at 5.5±0.2 degrees, a peak at 5.9±0.2 degrees, a peak at 7.6±0.2 degrees, a peak at 10.9±0.2 degrees, a peak at 12.1±0.2 degrees, a peak at 13.3±0.2 degrees, a peak at 14.6±0.2 degrees, a peak at 17.2±0.2 degrees, a peak at 18.8±0.2 degrees, a peak at 21.8±0.2 degrees, a peak at 22.5±0.2 degrees, a peak at 23.2±0.2 degrees, a peak at 23.7±0.2 degrees, a peak at 25.0±0.2 degrees, and a peak at 25.6±0.2 degrees on a 2θ scale in an X-ray powder diffraction pattern. In a further embodiment, the X-ray powder diffraction pattern is obtained using Cu K alpha radiation.

Figure 39:
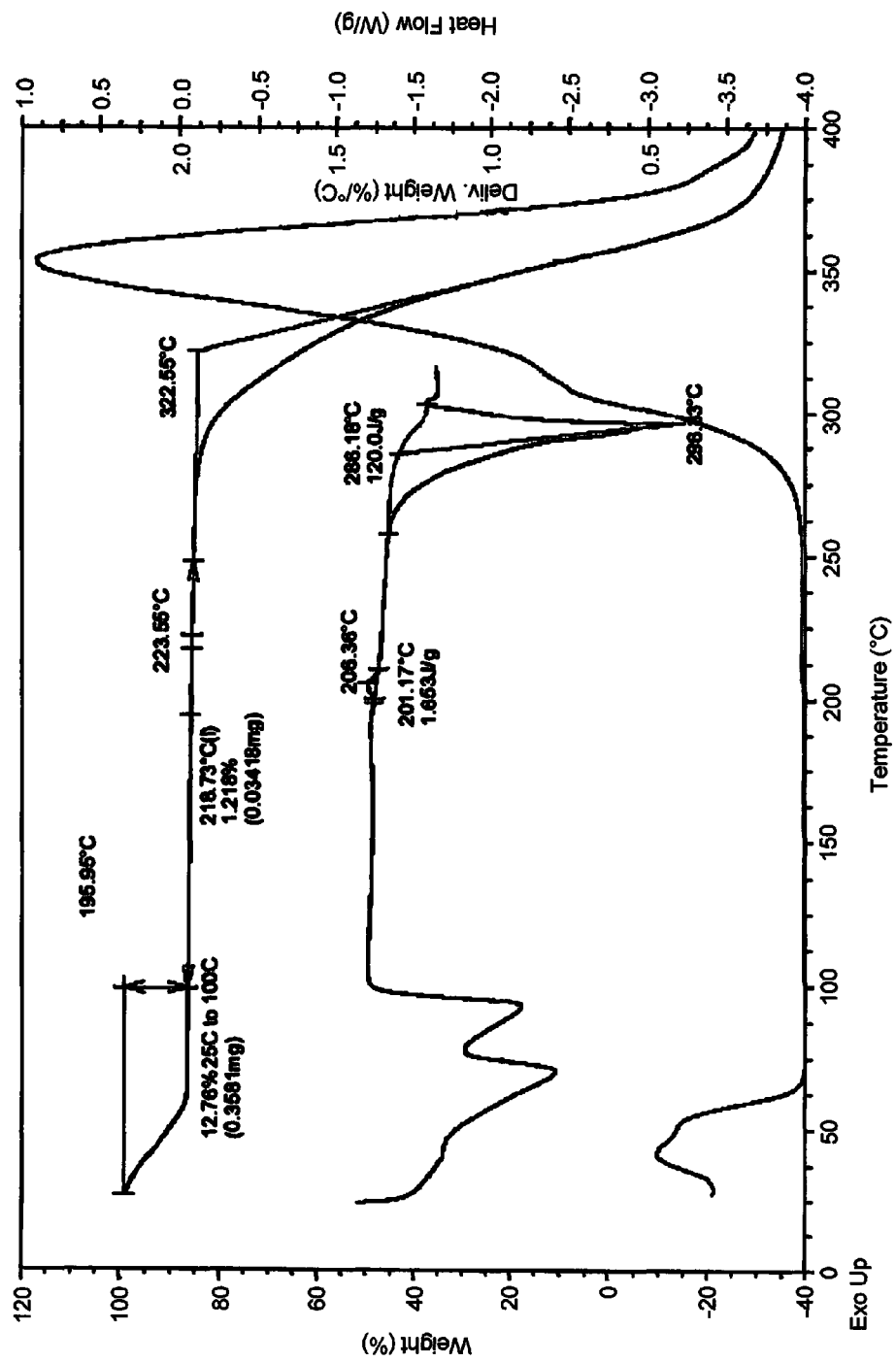
FIG. 39 is a thermogravimetric trace of Form W of Compound 1.

A thermogravimetric trace of Form W is provided as FIG. 39.

Processes for Making Crystalline Solvate Forms

In another aspect, the invention provides a process for making a crystalline solvate Form D of Compound 1 comprising:
 a) dissolving Form XX of Compound 1 in at least one solvent to form a mixture;
 b) heating the mixture until the solid has dissolved;
 c) precipitating Form D by cooling the mixtures; and
 d) isolating the Form D.

In one embodiment of this aspect, at least one of the solvents is acetonitrile.

In another embodiment of this aspect, the solvent is acetonitrile/water 75/25.

In another aspect, the invention provides a process for making a crystalline solvate Form E of Compound 1 comprising:
 a) dissolving Form XX of Compound 1 in at least one solvent to form a mixture;
 b) heating the mixture until the solid has dissolved;
 c) precipitating Form E by cooling the mixtures; and
 d) isolating the Form E.

In one embodiment of this aspect, at least one of the solvents is MEK.

In another embodiment of this aspect, the solvent is MEK/water.

In a further embodiment of this aspect, the solvent is MEK/water 99/1.

In a further embodiment of this aspect, the solvent is MEK/water 90/10.

In a further embodiment of this aspect, the solvent is MEK/water 80/20.

In another aspect, the invention provides a process for making a crystalline solvate Form E of Compound 1 comprising:
 a) slurrying Form XX of Compound 1 in acetonitrile containing water to form a mixture;
 b) removing the residual solid from the mixture by filtration;
 c) removing the solvent by rapid evaporation; and
 d) isolating the Form E.

In one embodiment of this aspect, the solvent is MEK/water 90/10.

In a further embodiment of this aspect, the solvent is MEK/water 80/20.

In another aspect, the invention provides a process for making a crystalline solvate Form E of Compound 1 comprising:
 a) slurrying amorphous Compound 1 in isopropyl acetate containing water to form a mixture;
 b) removing the residual solid from the mixture by filtration;
 c) removing the solvent by rapid evaporation; and
 d) isolating the Form E.

In one embodiment of this aspect, the solvent is MEK/water 90/10.

In a further embodiment of this aspect, the solvent is MEK/water 80/20.

In another aspect, the invention provides a process for making a crystalline solvate Form F of Compound 1 comprising:
 a) slurrying Form XX of Compound 1 in acetonitrile containing water to form a mixture;
 b) removing the residual solvent from the mixture by filtration;
 c) removing the solvent by rapid evaporation; and
 d) isolating the Form F.

In one embodiment of this aspect, the solvent is acetonitrile water 75/25.

In another aspect, the invention provides a process for making a semi-crystalline solvate Form G of Compound 1 comprising:
 a) slurrying Form XX of Compound 1 in isopropyl acetate to form a mixture;
 b) removing the residual solid from the mixture by filtration;
 c) removing the solvent by rapid evaporation; and
 d) isolating the Form G.

In one embodiment of this aspect, the solvent is isopropyl acetate.

In another aspect, the invention provides a process for making a crystalline solvate Form H of Compound 1 comprising:
  a) slurrying Form XX of Compound 1 in isopropyl acetate containing water to form a mixture;
  b) removing the residual solid from the mixture by filtration;
  c) removing the solvent by rapid evaporation; and
  d) isolating the Form H.

In one embodiment of this aspect, the solvent is isopropyl acetate/water 95/5. In another aspect, the invention provides a process for making a crystalline solvate Form I of Compound 1 comprising:
  a) slurrying Form XX of Compound 1 in methylethyl ketone to form a mixture;
  b) removing the residual solid from the mixture by filtration;
  c) removing the solvent by rapid evaporation; and
  d) isolating the Form I.

In another aspect, the invention provides a process for making a crystalline solvate Form J of Compound 1 comprising:
  a) slurrying Form XX of Compound 1 in methylethyl ketone containing water to form a mixture;
  b) removing the residual solid from the mixture by filtration;
  c) removing the solvent by rapid evaporation; and
  d) isolating the Form J.

In one embodiment of this aspect, the solvent is MEK/water 99/1.

In another aspect, the invention provides a process for making a crystalline solvate Form K of Compound 1 comprising:
  a) slurrying Form XX of Compound 1 in methylethyl ketone containing 0 percent to 30 percent water to form a mixture;
  b) removing the residual solid from the mixture by filtration;
  c) adding an antisolvent to the mixture to induce precipitation; and
  d) isolating the Form K.

In one embodiment of this aspect, at least one of the solvents is MEK.

In another embodiment of this aspect, the solvent is MEK/water.

In a further embodiment of this aspect, the solvent is MEK/water 99/1.

In a further embodiment of this aspect, the solvent is MEK/water 90/10.

In a further embodiment of this aspect, the solvent is MEK/water 80/20.

When the solvent is MEK or MEK/water, the antisolvent is a non-polar hydrocarbon solvent such as pentane hexane, heptane, octane, nonane, or the like. More particularly, the antisolvent is n-hexane.

In another aspect, the invention provides a process for making a crystalline solvate Form L of Compound 1 comprising:
  a) slurrying amorphous Compound 1 in isopropyl acetate containing water at 25° C. for 6 hours to 4 weeks to form a mixture;
  b) removing the residual solvent from the mixture by filtration;
  c) removing the solvent by rapid evaporation; and
  d) isolating the Form L.

In one embodiment of this aspect, the solvent is isopropyl acetate/water 95/5.

In another embodiment of this aspect, the process occurs from 12 hours to 3 weeks.

In another embodiment of this aspect, the process occurs from 24 hours to 2 weeks.

In another aspect, the invention provides a process for making a crystalline solvate Form M of Compound 1 comprising:
  a) at 25° C., slurrying amorphous Compound 1 in methylethyl ketone containing 0 percent to 1 percent water for 12 hours to a month to form a mixture;
  b) removing the residual solid from the mixture by filtration; and
  c) isolating the Form M.

In one aspect of this embodiment, the mixture further comprises one or more polymeric additives.

In another embodiment of this aspect, the additives are selected from hydroxypropyl methyl cellulose (HPMC) and sodium lauryl sulfate (SLS).

In another aspect, the invention provides a process for making a crystalline solvate Form N of Compound 1 comprising:
  a) at 25° C., slurrying amorphous Compound 1 in methylethyl ketone containing 10 percent to 20 percent water for 12 hours to a month to form a mixture;
  b) removing the residual solid from the mixture by filtration; and
  c) isolating the Form N.

In one aspect of this embodiment, the mixture further comprises one or more polymeric additives.

In another embodiment of this aspect, the additives are selected from HPMC and SLS.

In another aspect, the invention provides a process for making a crystalline solvate Form O of Compound 1 comprising:
  a) at 70° C., slurrying amorphous Compound 1 in methylethyl ketone containing 0 percent to 1 percent water for 6 hours to 4 weeks to form a mixture;
  b) heating the mixture at approximately 70° C. for 1 to 30 hours;
  c) removing the residual solid from the mixture by filtration; and
  d) isolating the Form O.

In one aspect of this embodiment, the mixture further comprises one or more polymeric additives.

In another embodiment of this aspect, the additives are HPMC and SLS.

In another embodiment of this aspect, the solvent is MEK. When the solvent is MEK, the slurry is heated at 70° C. for from 12 hours to 3 weeks, more preferably from 24 hours to 2 weeks.

In another embodiment of this aspect, the solvent is MEK/$H_2O$ 99/1. When the solvent is MEK/$H_2O$ 99/1, the slurry is heated at 70° C. for from 6 hours to 1 week, more preferably from 12 hours to 24 hours.

In another aspect, the invention provides a process for making a crystalline solvate Form P of Compound 1 comprising:
  a) at 70° C., slurrying amorphous Compound 1 in methylethyl ketone containing 10 percent to 20 percent water for 12 to 24 hours to form a mixture;
  b) heating the mixture at approximately 70° C. for 1 to 30 hours;
  c) removing the residual solid from the mixture by filtration; and
  d) isolating the Form P.

In one aspect of this embodiment, the mixture further comprises one or more polymeric additives.

In another embodiment of this aspect, the additives are HPMC and SLS.

In another aspect, the invention provides a process for making a crystalline solvate Form Q of Compound 1 comprising:
 a) at 70° C., slurrying amorphous Compound 1 in methylethyl ketone containing 10 percent to 20 percent water for 2 days to 3 weeks to form a mixture;
 b) heating the mixture at approximately 70° C. for 1 to 30 hours;
 c) removing the residual solid from the mixture by filtration; and
 d) isolating the Form Q.

In one aspect of this embodiment, the mixture further comprises one or more polymeric additives.

In another embodiment of this aspect, the additives are HPMC and SLS.

In another aspect, the invention provides a process for making a crystalline solvate Form R of Compound 1 comprising:
 a) drying the Form D of Compound 1 in a vacuum oven at a temperature between room temperature and 45° C.; and
 b) isolating the Form R.

In another aspect, the invention provides a process for making a crystalline solvate Form S of Compound 1 comprising:
 a) drying Form K of Compound 1 in a vacuum oven at a temperature between room temperature and 45° C.; and
 b) isolating the Form R.

In another aspect, the invention provides a process for making a crystalline solvate Form T of Compound 1 comprising:
 a) slurrying Form XX of Compound 1 in methylethyl ketone containing 0 percent to 30 percent water to form a mixture;
 b) removing the residual solid from the mixture by filtration;
 c) adding an antisolvent to the mixture to induce precipitation; and
 d) isolating the Form T.

In another aspect, the invention provides a process for making a crystalline solvate Hydrate B of Compound 1.

In one embodiment of this aspect, the process for making a crystalline solvate Hydrate B comprises:
 a) slurrying amorphous Compound 1 in in simulated fluids (FeSSIF);
 b) removing the residual solid from the mixture by filtration;
 c) isolating the Hydrate Form B.

In another embodiment of this aspect, the process for making a crystalline solvate Hydrate B comprises:
 a) heating a mixture of amorphous Compound 1 and water;
 b) removing the residual solid from the mixture by filtration;
 c) isolating the Hydrate Form B.

In a further embodiment, the ratio of amorphous Compound 1 and water is about 1:1.

In another aspect, the invention provides a crystalline solvate of Compound 1, wherein the solvent is a polar solvent, more preferably a polar aprotic solvent. The polar aprotic solvent is acetonitrile, MEK, or isopropyl acetate.

In another aspect, the invention provides a crystalline solvate of Compound 1, wherein the solvent is a polar solvent, more preferably a polar aprotic solvent, optionally additionally comprising water.

In another aspect, the invention provides a crystalline solvate of Compound 1, wherein the solvent is selected from the group consisting of acetonitrile, acetonitrile/water, isopropyl acetate, isopropyl acetate/water, methylethyl ketone, and methylethyl ketone/water.

In one aspect of this embodiment, the solvent is acetonitrile.

In another aspect of this embodiment, the solvent is acetonitrile/water 75/25.

In another aspect of this embodiment, the solvent is isopropyl acetate.

In another aspect of this embodiment, the solvent is isopropyl acetate/water 95/5.

In another aspect of this embodiment, the solvent is MEK.

In another aspect of this embodiment, the solvent is MEK/water 99/1.

In another aspect of this embodiment, the solvent is MEK/water 90/10.

In another aspect of this embodiment, the solvent is MEK/water 80/20.

In one embodiment of this aspect, the solvent is acetonitrile or acetonitrile/water and the crystalline solvate is Form D, Form F, or Form R, as described above.

In another embodiment of this aspect, the solvent is isopropyl acetate or isopropyl acetate/water and the crystalline solvate, which is Form G, Form H, Form L, or Form T.

In a further embodiment of this aspect, the solvent is methylethyl ketone or methylethyl ketone/water and the crystalline solvate is Form E, Form I, Form J, Form K, Form M, Form N, Form O, Form P, or Form S.

In another aspect, the invention provides a process for making a crystalline solvate of Compound 1 comprising:
 a) dissolving Form XX of Compound 1 in at least one solvent to form a mixture;
 b) heating the mixture until the solid has dissolved;
 c) precipitating the crystalline solvate by cooling the mixtures; and
 d) isolating the crystalline solvate.

In one embodiment of this aspect, the solvent is acetonitrile or acetonitrile/water and the crystalline solvate is Form D.

In another embodiment of this aspect, the solvent is methylethyl ketone or methylethyl ketone/water and the crystalline solvate is Form E.

In another aspect, the invention provides a process for making a crystalline solvate of Compound 1 comprising:
 a) dissolving Form XX of Compound 1 in at least one solvent to form a mixture;
 b) removing the residual solvent from the mixture by filtration;
 c) removing the solvent by rapid evaporation; and
 d) isolating the crystalline solvate.

In one embodiment of this aspect, the solvent is acetonitrile/water and the crystalline solvate is Form F.

In another embodiment of this aspect, the solvent is isopropyl acetate and the crystalline solvate is Form G.

In another embodiment of this aspect, the solvent isopropyl acetate/water and the crystalline solvate is Form H.

In another embodiment of this aspect, the solvent methylethyl ketone and the crystalline solvate is Form I.

In another aspect of this embodiment, the solvent is methylethyl ketone/water and the crystalline solvate is Form J or Form E.

In another aspect, the invention provides a process for making a crystalline solvate of Compound 1 comprising:
a) slurrying amorphous of Compound 1 in at least one solvent;
b) removing the residual solid from the mixture by filtration;
c) adding an antisolvent to the mixture to induce precipitation; and
d) isolating the crystalline solvate.

In one embodiment of this aspect, the solvent is methylethyl ketone containing 0 to 30 percent water and the crystalline solvate is Form K.

In another embodiment of this aspect, the solvent is isopropyl acetate/water and the crystalline solvate is Form T.

In another aspect, the invention provides a process for making a crystalline solvate of Compound 1 comprising:
a) slurrying amorphous Compound 1 in at least one solvent;
b) removing the residual solvent from the mixture by filtration;
c) removing the solvent by rapid evaporation; and
d) isolating the crystalline solvate.

In one embodiment of this aspect, the solvent is isopropyl acetate containing water and the crystalline solvate is Form L.

In another aspect, the invention provides a process for making a crystalline solvate of Compound 1 comprising:
a) slurrying at room temperature amorphous Compound 1 in at least one solvent further in the presence of HPMC and sodium lauryl sulfate to form a mixture;
b) removing the residual solid from the mixture by filtration;
c) allowing the crystalline solvate to precipitate from the solvent; and
d) isolating the crystalline solvate.

In one embodiment of this aspect, the crystalline solvate is Form M or Form N.

In another aspect, the invention provides a process for making a crystalline solvate of Compound 1 comprising:
a) slurrying at 70° C. amorphous Compound 1 in at least one solvent further in the presence of HPMC and sodium lauryl sulfate to form a mixture;
b) removing the residual solid from the mixture by filtration;
c) allowing the crystalline solvate to precipitate from the solvent; and
d) isolating the crystalline solvate.

In one embodiment of this aspect, the crystalline solvate is solvate is Form O, Form P, or Form Q.

In another aspect, the invention provides a process for making a crystalline solvate of Compound 1 comprising:
a) drying solvate Form Compound 1 in a vacuum oven at a temperature between room temperature and 45° C.; and
b) isolating the crystalline solvate.

In one aspect of this embodiment, the solvate form used in step (a) is Form D and the solvate form isolated is Form R.

In another aspect of this embodiment, the solvate form used in step (a) is Form K and the solvate form isolated is Form S.

In another aspect, the invention provides crystalline solvate Form D of Compound 1 prepared by the process comprising
a) dissolving Form XX of Compound 1 in at least one solvent to form a mixture;
b) heating the mixture until the solid has dissolved;
c) precipitating Form D by cooling the mixtures; and
d) isolating the Form D.

In one embodiment of this aspect, at least one of the solvents is acetonitrile.

In another embodiment of this aspect, the solvent is acetonitrile/water 75/25.

In another aspect, the invention provides crystalline solvate Form E of Compound 1 prepared by the process comprising:
a) dissolving Form XX of Compound 1 in at least one solvent to form a mixture;
b) heating the mixture until the solid has dissolved;
c) precipitating Form E by cooling the mixtures; and
d) isolating the Form E.

In one embodiment of this aspect, at least one of the solvents is MEK.

In another embodiment of this aspect, the solvent is MEK/water.

In a further embodiment of this aspect, the solvent is MEK/water 99/1.

In a further embodiment of this aspect, the solvent is MEK/water 90/10.

In a further embodiment of this aspect, the solvent is MEK/water 80/20.

In another aspect, the invention provides crystalline solvate Form E of Compound 1 prepared by the process comprising:
a) slurrying Form XX of Compound 1 in acetonitrile containing water to form a mixture;
b) removing the residual solid from the mixture by filtration;
c) removing the solvent by rapid evaporation; and
d) isolating the Form E.

In one embodiment of this aspect, the solvent is MEK/water 90/10.

In a further embodiment of this aspect, the solvent is MEK/water 80/20.

In another aspect, the invention provides crystalline solvate Form E of Compound 1 prepared by the process comprising:
a) slurrying amorphous Compound 1 in isopropyl acetate containing water to form a mixture;
b) removing the residual solid from the mixture by filtration;
c) removing the solvent by rapid evaporation; and
d) isolating the Form E.

In one embodiment of this aspect, the solvent is MEK/water 90/10.

In a further embodiment of this aspect, the solvent is MEK/water 80/20.

In another aspect, the invention provides crystalline solvate Form F of Compound 1 prepared by the process comprising:
a) slurrying Form XX of Compound 1 in acetonitrile containing water to form a mixture;
b) removing the residual solvent from the mixture by filtration;
c) removing the solvent by rapid evaporation; and
d) isolating the Form F.

In one embodiment of this aspect, the solvent is acetonitrile water 75/25.

In another aspect, the invention provides crystalline solvate Form G of Compound 1 prepared by the process comprising:
a) slurrying Form XX of Compound 1 in isopropyl acetate to form a mixture;
b) removing the residual solid from the mixture by filtration;
c) removing the solvent by rapid evaporation; and
d) isolating the Form G.

In one embodiment of this aspect, the solvent is isopropyl acetate.

In another aspect, the invention provides crystalline solvate Form H of Compound 1 prepared by the process comprising:
a) slurrying Form XX of Compound 1 in isopropyl acetate containing water to form a mixture;

b) removing the residual solid from the mixture by filtration;
c) removing the solvent by rapid evaporation; and
d) isolating the Form H.

In one embodiment of this aspect, the solvent is isopropyl acetate/water 95/5. In another aspect, the invention provides crystalline solvate Form I of Compound 1 prepared by the process comprising:
a) slurrying Form XX of Compound 1 in methylethyl ketone to form a mixture;
b) removing the residual solid from the mixture by filtration;
c) removing the solvent by rapid evaporation; and
d) isolating the Form I.

In another aspect, the invention provides crystalline solvate Form J of Compound 1 prepared by the process comprising:
a) slurrying Form XX of Compound 1 in methylethyl ketone containing water to form a mixture;
b) removing the residual solid from the mixture by filtration;
c) removing the solvent by rapid evaporation; and
d) isolating the Form J.

In one embodiment of this aspect, the solvent is MEK/water 99/1.

In another aspect, the invention provides crystalline solvate Form K of Compound 1 prepared by the process comprising:
a) slurrying Form XX of Compound 1 in methylethyl ketone containing 0 percent to 30 percent water to form a mixture;
b) removing the residual solid from the mixture by filtration;
c) adding an antisolvent to the mixture to induce precipitation; and
d) isolating the Form K.

In one embodiment of this aspect, at least one of the solvents is MEK.

In another embodiment of this aspect, the solvent is MEK/water.

In a further embodiment of this aspect, the solvent is MEK/water 99/1.

In a further embodiment of this aspect, the solvent is MEK/water 90/10.

In a further embodiment of this aspect, the solvent is MEK/water 80/20.

When the solvent is MEK or MEK, the antisolvent is a non-polar hydrocarbon solvent such as pentane hexane, heptane, octane, nonane, or the like. More particularly, the antisolvent is n-hexane.

In another aspect, the invention provides crystalline solvate Form L of Compound 1 prepared by the process: comprising:
a) slurrying amorphous Compound 1 in isopropyl acetate containing water at 25° C. for 6 hours to 4 weeks to form a mixture;
b) removing the residual solvent from the mixture by filtration;
c) removing the solvent by rapid evaporation; and
d) isolating the Form L.

In one embodiment of this aspect, the solvent is isopropyl acetate/water 95/5.

In another embodiment of this aspect, the process occurs from 12 hours to 3 weeks.

In another embodiment of this aspect, the process occurs from 24 hours to 2 weeks.

In another aspect, the invention provides crystalline solvate Form M of Compound 1 prepared by the process comprising:
a) at 25° C., slurrying amorphous Compound 1 in methylethyl ketone containing 0 percent to 1 percent water for 12 hours to a month to form a mixture;
b) removing the residual solid from the mixture by filtration; and
c) isolating the Form M.

In one aspect of this embodiment, the mixture further comprises one or more polymeric additives.

In another embodiment of this aspect, the additives are selected from hydroxypropyl methyl cellulose (HPMC) and sodium lauryl sulfate (SLS).

In another aspect, the invention provides crystalline solvate Form N of Compound 1 prepared by the process comprising:
a) at 25° C., slurrying amorphous Compound 1 in methylethyl ketone containing 10 percent to 20 percent water for 12 hours to a month to form a mixture;
b) removing the residual solid from the mixture by filtration; and
c) isolating the Form N.

In one aspect of this embodiment, the mixture further comprises one or more polymeric additives.

In another embodiment of this aspect, the additives are selected from HPMC and SLS.

In another aspect, the invention provides crystalline solvate Form O of Compound 1 prepared by the process comprising:
a) at 70° C., slurrying amorphous Compound 1 in methylethyl ketone containing 0 percent to 1 percent water for 6 hours to 4 weeks to form a mixture;
b) heating the mixture at approximately 70° C. for 1 to 30 hours;
c) removing the residual solid from the mixture by filtration; and
d) isolating the Form O.

In one aspect of this embodiment, the mixture further comprises one or more polymeric additives.

In another embodiment of this aspect, the additives are HPMC and SLS.

In another embodiment of this aspect, the solvent is MEK. When the solvent is MEK, the slurry is heated at 70° C. for from 12 hours to 3 weeks, more preferably from 24 hours to 2 weeks.

In another embodiment of this aspect, the solvent is MEK/$H_2O$ 99/1. When the solvent is MEK/$H_2O$ 99/1, the slurry is heated at 70° C. for from 6 hours to 1 week, more preferably from 12 hours to 24 hours.

In another aspect, the invention provides crystalline solvate Form P of Compound 1 prepared by the process comprising:
a) at 70° C., slurrying amorphous Compound 1 in methylethyl ketone containing 10 percent to 20 percent water for 12 to 24 hours to form a mixture;
b) heating the mixture at approximately 70° C. for 1 to 30 hours;
c) removing the residual solid from the mixture by filtration; and
d) isolating the Form P.

In one aspect of this embodiment, the mixture further comprises one or more polymeric additives.

In another embodiment of this aspect, the additives are HPMC and SLS.

In another aspect, the invention provides crystalline solvate Form Q of Compound 1 prepared by the process comprising:
a) at 70° C., slurrying amorphous Compound 1 in methylethyl ketone containing 10 percent to 20 percent water for 2 days to 3 weeks to form a mixture;
b) heating the mixture at approximately 70° C. for 1 to 30 hours;

c) removing the residual solid from the mixture by filtration; and
d) isolating the Form Q.

In one aspect of this embodiment, the mixture further comprises one or more polymeric additives.

In another embodiment of this aspect, the additives are HPMC and SLS.

In another aspect, the invention provides crystalline solvate Form R of Compound 1 prepared by the process comprising:
a) drying the Form D of Compound 1 in a vacuum oven at a temperature between room temperature and 45° C.; and
b) isolating the Form R.

In another aspect, the invention provides crystalline solvate Form S of Compound 1 prepared by the process comprising:
a) drying Form K of Compound 1 in a vacuum oven at a temperature between room temperature and 45° C.; and
b) isolating the Form R.

In another aspect, the invention provides crystalline solvate Form T of Compound 1 prepared by the process comprising:
a) slurrying Form XX of Compound 1 in methylethyl ketone containing 0 percent to 30 percent water to form a mixture;
b) removing the residual solid from the mixture by filtration;
c) adding an antisolvent to the mixture to induce precipitation; and
d) isolating the Form T.

OTHER ASPECTS OF THE INVENTION

Uses, Formulation and Administration

Pharmaceutically Acceptable Compositions

In one aspect of the present invention, pharmaceutically acceptable compositions are provided, wherein these compositions comprise Forms D, E, F, G, H, I, J, K, L, M, N, O, P, Q, R, S, T, W, or Hydrate B as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In one aspect, the invention provides a method of treating or lessening the severity of a disease in a patient comprising administering to said patient form D, E, F, G, H, I, J, K, L, M, N, O, P, Q, R, S, T, W, or Hydrate B, or any combination of these forms, as described herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Sträussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In some embodiments, the method includes treating or lessening the severity of cystic fibrosis in a patient comprising administering to said patient form D, E, F, G, H, I, J, K, L, M, N, O, P, Q, R, S, T, W, or Hydrate B, or any combination of these forms, as described herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient form D, E, F, G, H, I, J, K, L, M, N, O, P, Q, R, S, T, W, or Hydrate B, or any combination of these forms, as described herein. In one embodiment, the method includes treating or lessening the severity of cystic fibrosis in a patient possessing the G551D mutation of human CFTR comprising administering to said patient form D, E, F, G, H, I, J, K, L, M, N, O, P, Q, R, S, T, W, or Hydrate B, or any combination of these forms, as described herein. In one embodiment, the method includes treating or lessening the severity of cystic fibrosis in a patient possessing the ΔF508 mutation of human CFTR on at least one allele comprising administering to said patient form D, E, F, G, H, I, J, K, L, M, N, O, P, Q, R, S, T, W, or Hydrate B, or any combination of these forms, as described herein. In one embodiment, the method includes treating or lessening the severity of cystic fibrosis in a patient possessing the ΔF508 mutation of human CFTR on both alleles comprising administering to said patient form D, E, F, G, H, I, J, K, L, M, N, O, P, Q, R, S, T, W, or Hydrate B, or any combination of these forms, as described herein. In one embodiment, the method includes treating or lessening the severity of cystic fibrosis in a patient possessing the G551D mutation of human CFTR on at least one allele comprising administering to said patient form D, E, F, G, H, I, J, K, L, M, N, O, P, Q, R, S, T, W, or Hydrate B, or any combination of these forms, as described herein. In one embodiment, the method includes treating or lessening the severity of cystic fibrosis in a patient possessing the G551D mutation of human CFTR on both alleles comprising administering to said patient form D, E, F, G, H, I, J, K, L, M, N, O, P, Q, R, S, T, W, or Hydrate B, or any combination of these forms, as described herein.

In yet another aspect, the present invention provides a method of treating or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising forms D, E, F, G, H, I, J, K, L, M, N, O, P, Q, R, S, T, W, or Hydrate B, or any combination of these forms as described herein, to a subject, preferably a mammal, in need thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma, comprising administering to said patient form D, E, F, G, H, I, J, K, L, M, N, O, P, Q, R, S, T, W, or Hydrate B, or any combination of these forms, as described herein.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gastroesophageal reflux disease, gastrointestinal malignancies, inflammatory bowel disease, constipation, diabetes, arthritis, osteoporosis, and osteopenia, comprising administering to said patient form D, E, F, G, H, I, J, K, L, M, N, O, P, Q, R, S, T, W, or Hydrate B, or any combination of these forms, as described herein.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Sträussler-Scheinker syndrome, Gorham's Syndrome, chloride channelopathies, myotonia congenita (Thomson and Becker forms), Bartter's syndrome type III, Dent's disease, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of. Forms D, E, F, G, H, I, J, K, L, M, N, O, P, Q, R, S, T, W, or Hydrate B, or any combination of these forms, as described herein.

According to an alternative preferred embodiment, the present invention provides a method of treating cystic fibrosis comprising the step of administering to said mammal a composition comprising the step of administering to said mammal an effective amount of a composition comprising Forms D, E, F, G, H, I, J, K, L, M, N, O, P, Q, R, S, T, W, or Hydrate B, or any combination of these forms, described herein.

According to the invention an "effective amount" of Forms D, E, F, G, H, I, J, K, L, M, N, O, P, Q, R, S, T, W, or Hydrate B, any combination of these forms, or a pharmaceutically acceptable composition thereof is that amount effective for treating or lessening the severity of one or more of the diseases, disorders or conditions as recited above.

Forms D, E, F, G, H, I, J, K, L, M, N, O, P, Q, R, S, T, W, or Hydrate B, or any combination of these forms, or a pharmaceutically acceptable composition thereof may be administered using any amount and any route of administration effective for treating or lessening the severity of one or more of the diseases, disorders or conditions as recited above.

In certain embodiments, Forms D, E, F, G, H, I, J, K, L, M, N, O, P, Q, R, S, T, W, or Hydrate B, any combination of these forms, or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, $\Delta$F508.

In another embodiment, Forms D, E, F, G, H, I, J, K, L, M, N, O, P, Q, R, S, T, W, or Hydrate B, or any combination of these forms, described herein or a pharmaceutically acceptable composition thereof, is useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, Forms D, E, F, G, H, I, J, K, L, M, N, O, P, Q, R, S, T, W, or Hydrate B, or any combination of these forms, described herein, or a pharmaceutically acceptable composition thereof, is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Forms D, E, F, G, H, I, J, K, L, M, N, O, P, Q, R, S, T, W, or Hydrate B, or any combination of these forms described herein or a pharmaceutically acceptable composition thereof, is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection.

This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the Forms D, E, F, G, H, I, J, K, L, M, N, O, P, Q, R, S, T, W, or Hydrate B, or any combination thereof described herein or a pharmaceutically acceptable composition thereof can be employed in combination therapies, that is, Forms D, E, F, G, H, I, J, K, L, M, N, O, P, Q, R, S, T, W, or Hydrate B, or any combination thereof described herein or a pharmaceutically acceptable composition thereof, can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodilator, an anti-biotic, an anti-infective agent, an anti-inflammatory agent, a CFTR modulator other than a compound of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodilator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[[(3S,5R)-5-(4-amino-2-oxopyrimidin-1-yl)-3-hydroxyoxolan-2-yl]methoxy-hydroxyphosphoryl] [[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example in PCT Publication No. WO2009/074575, the entire contents of which are incorporated herein in their entirety.

Amongst other diseases described herein, combinations of CFTR modulators, such as Forms D, E, F, G, H, I, J, K, L, M, N, O, P, Q, R, S, T, W, or Hydrate B, and agents that reduce the activity of ENaC are used for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as Forms D, E, F, G, H, I, J, K, L, M, N, O, P, Q, R, S, T, W, or Hydrate B, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as Forms D, E, F, G, H, I, J, K, L, M, N, O, P, Q, R, S, T, W, or Hydrate B, and agents that reduce the activity of ENaC are useful for the treatment of bronchitis of whatever type or genesis including, e.g., acute, arachidic, catarrhal, croupus, chronic or phthinoid bronchitis.

In another embodiment, the additional agent is a CFTR modulator other than Form XX, Forms D, E, F, G, H, I, J, K, L, M, N, O, P, Q, R, S, T, W, or Hydrate B, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R, 7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl) cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In one embodiment, the additional agent is a CFTR modulator other than a compound of the present invention.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Forms D, E, F, G, H, I, J, K, L, M, N, O, P, Q, R, S, T, W, or Hydrate B, or any combination thereof described herein or a pharmaceutically acceptable composition thereof, may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with Forms D, E, F, G, H, I, J, K, L, M, N, O, P, Q, R, S, T, W, or Hydrate B, or any combination thereof described herein or a pharmaceutically acceptable composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with Forms D, E, F, G, H, I, J, K, L, M, N, O, P, Q, R, S, T, W, or Hydrate B, or any combination thereof described herein or a pharmaceutically acceptable composition thereof. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with Forms D, E, F, G, H, I, J, K, L, M, N, O, P, Q, R, S, T, W, or Hydrate B, or any combination thereof described herein or a pharmaceutically acceptable composition thereof.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." Biophys J 69(4): 1272-80, and Gonzalez, J. E. and R. Y. Tsien (1997); "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising Forms D, E, F, G, H, I, J, K, L, M, N, O, P, Q, R, S, T, W, or Hydrate B, or any combination thereof or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of Forms D, E, F, G, H, I, J, K, L, M, N, O, P, Q, R, S, T, W, or Hydrate B, or any combination thereof described herein. In preferred embodiments, the kit is used to measure the density of CFTR.

In another aspect, the invention provides a kit for use in measuring the activity of CFTR or a fragment thereof in a biological sample in vitro or in vivo, comprising:
(i) a composition comprising crystalline solvate Form D, E, F, G, H, I, J, K, L, M, N, O, P, Q, R, S, T, W, or Hydrate B, or combinations thereof;
(ii) instructions for:
 (a) contacting the composition with the biological sample;
 (b) measuring activity of said CFTR or a fragment thereof.

In one embodiment, the kit further comprises instructions for:
i. contacting an additional composition with the biological sample;
ii. measuring the activity of said CFTR, or a fragment thereof, in the presence of said additional compound; and
iii. comparing the activity of the CFTR, or fragment thereof, in the presence of the additional compound with the density of CFTR, or fragment thereof, in the presence of a crystalline solvate Form D, E, F, G, H, I, J, K, L, M, N, O, P, Q, R, S, T, W, or Hydrate B, or combination thereof.

In another embodiment, the step of comparing the activity of said CFTR, or fragment thereof, provides a measure of the density of said CFTR, or fragment thereof In order that the invention described herein may be more fully understood, the following examples are set forth. It should be understood that these examples are for illustrative purposes only and are not to be construed as limiting this invention in any manner.

EXAMPLES

Polymorphic screening of Compound 1 was conducted within the process crystallization (acetonitrile, isopropyl acetate, water) and spray-drying (methyl ethyl ketone, water)

solvent systems in order to understand its polymorphic behavior under process relevant conditions.

Materials and Methods

Crystalline Compound 1 of Form XX was used in the evaporation, antisolvent addition and crash cooling experiments described below.

Amorphous Compound 1 or neat amorphous Compound 1 was used for slurry experiments in acetonitrile/water and isopropyl acetate/water solvent systems as well as in methyl ethyl ketone (MEK)/water solvent systems.

Spray-dried dispersion containing amorphous Compound 1 in the presence of the polymeric additives that include hypromellose acetate succinate (HPMCAS), and sodium lauryl sulfate (SLS) Fischer Scientific, was used for slurry experiments in the MEK/water spray-drying solvent systems.

Preparation of Crystalline Compound 1 of Form XX

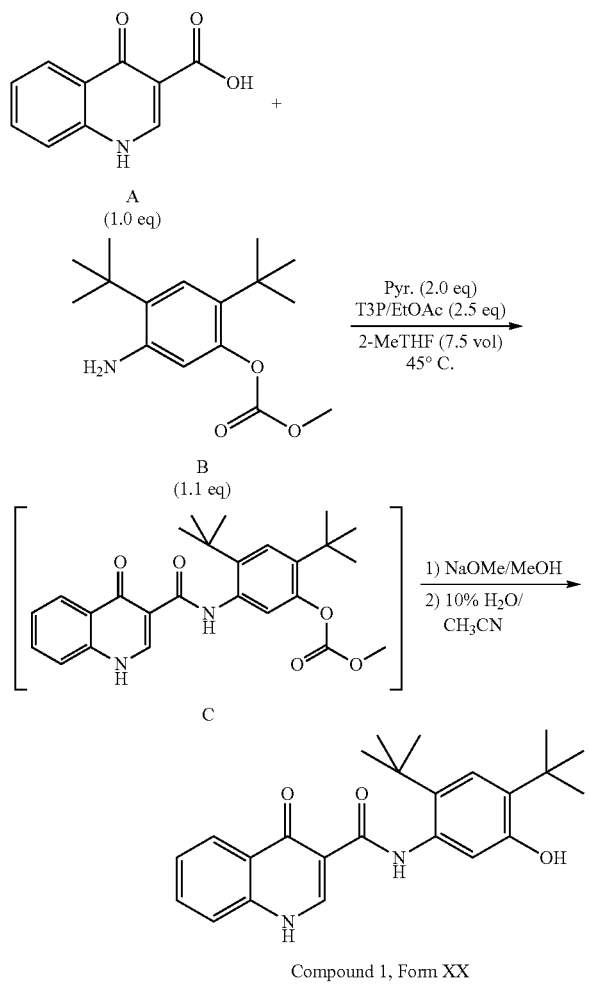

Compound A (1.0 eq.) and Compound B (1.1 eq.) were charged to a reactor. 2-MeTHF (4.0 vol., relative to Compound A) was added followed by T3P® 50% solution in EtOAc (2.5 eq.). The T3P charge vessel was washed with 2-MeTHF (3.5 vol.). Pyridine (2.0 eq.) was then charged. The resulting suspension was heated to 45.0 to 50.0° C. and held at this temperature for 15 hours. A sample was taken and checked for completion by HPLC. Once complete, the resulting mixture was cooled to 20.0° C.+/−5.0° C. 2-MeTHF was charged (12.5 vol.) to dilute the mixture. The reaction mixture was washed with water (10.0 vol.) 3 times. 2-MeTHF was charged to bring the total volume of reaction to 40.0 vol. (−16.5 vol. charged). Residual water was removed by continuous distillation at 35.0° C.+/−5° C. from 40 vol. to 30 vol. with 2-MeTHF until in-process control testing using the Karl Fisher method shows the water content to be no more than 1.0% w/w. The solution was cooled to 20.0° C.+/−5.0° C. To this solution was charged NaOMe/MeOH (1.7 equiv) to perform the hydrolysis of the carbonate. The reaction was stirred for no less than 1.0 hours, and checked for completion by HPLC. Once complete, the reaction was quenched with 1 N HCl/$H_2O$ (10.0 vol.), and washed with 0.1; N HCl (10.0 vol.). The organic solution was polish filtered to remove any particulates and placed in a second flask. The filtered solution was concentrated at 25.0° C.+/−5.0° C. under reduced pressure to 20 vol. $CH_3CN$ was added to 40 vol. and the solution concentrated at 25.0° C.+/−5.0° C. to 20 vol. The addition of $CH_3CN$ and concentration was repeated 2 more times for a total of 3 additions of $CH_3CN$ and 4 concentrations to 20 vol. After the final concentration to 20 vol., 16.0 vol. of $CH_3CN$ was charged followed by 4.0 vol. of $H_2O$ to make a final concentration of 40 vol. of 10% $H_2O$/$CH_3CN$ relative to Compound A. This slurry was refluxed for 5 hours. The slurry was cooled to 20.0° C.+/−5° C. and filtered. The cake was washed with $CH_3CN$ (5 vol.)$_2$ times. The resulting solid was dried in a vacuum oven at 50.0° C.+/−5.0° C. until a constant weight is attained.

Preparation of Amorphous Compound 1 (also referred to as Neat Amorphous Compound 1)

The following suspension was prepared by stirring Compound 1, Form XX into 90% MEK/10% water according to Table A.

TABLE A

| (MEK/Water = 90/10) | Weight (g) |
|---|---|
| MEK | 162.00 |
| Water | 18.00 |
| Compound 1, Form XX | 20.00 |
| Total Solution Weight | 200.00 |
| Solids Loading | 20.00 |

Spray drying was performed on a Buchi Mini Spray Dryer B-290 with dehumidifier B-296 and Inert Loop B-295 using the parameters used in Table B.

TABLE B

| Spray Drying Parameters | |
|---|---|
| INLET Temperature | 150° C. |
| OUTLET Temperature | 60° C. |
| Nitrogen Pressure | 120 psi |
| Aspirator | 100% |
| Pump Rate | 25% |
| Nozzle Cleaner Setting | 0 |
| Rotameter | 40 mm |
| Filter Pressure | 11 mbar |
| Condenser Temperature | 5° C. |
| Run Time | 37 min. |

The system was saturated with solvent that was to be sprayed, and inlet and outlet temperatures were allowed to equilibrate before spray drying.

Preparation of Spray Dried Dispersion (SDD) Containing Amorphous Compound 1

A solvent system of MEK and DI water, formulated according to the ratio 90 wt % MEK/10 wt % DI water, was heated to a temperature of 20-30° C. in a reactor, equipped with a portable agitator and thermal circuit. Into this solvent system, hypromellose acetate succinate polymer (HPMCAS) (HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 12.5 wt % solids. The actual amounts of ingredients and solvents used to generate this mixture are recited in Table C, below:

TABLE C

Solid Spray Dispersion Ingredients

|  | Units | Batch |
| --- | --- | --- |
| N-[2,4-Bis(1,1-dimethylethyl)-5-hydroxyphenyl]-1,4-dihydro-4-oxoquinoline-3-carboxamide (Form XX) | Kg | 24.00 |
| HPMCAS | Kg | 5.850 |
| SLS | Kg | 0.1500 |
| Total Solids | Kg | 30.00 |
| MEK | Kg | 189.0 |
| Water | Kg | 21.00 |
| Total Solvents | Kg | 210.0 |
| Total Spray Solution Weight | Kg | 240.0 |

The mixture was maintained at a temperature of 22-26° C. and mixed until it was substantially homogenous and all components were substantially dissolved.

A spray drier, Niro Production Minor Spray Dryer, fitted with pressure nozzle (Spraying Systems Maximum Free Passage (MFP) SK series nozzle having orifice size 72 and core size number 16), was used in closed cycle mode (i.e., with recirculation of the drying gas), following the dry spray process parameters recited in Table C2, below. The spray nozzle was situated approximately 5 cm from the top of the spray drying vessel. The solution was manually agitated during spray drying using a HDPE spatula.

TABLE C2

Dry spray process parameters.

| Parameter | Target Value |
| --- | --- |
| Feed Pressure | 30-44 bar |
| Feed Flow Rate | 15-21 Kg/hr |
| Inlet Temperature | 78-84° C. |
| Outlet Temperature | 45-47° C. |
| Vacuum Dryer Temperature (Drying Time) | 60° C. (+/−5° C.) and 80° C. (+/−5° C.) (see below) |
| Vacuum Drying Time | 112 hours total |

A high efficiency cyclone separated the wet product from the spray gas and solvent vapors. The wet product was transferred to a tray vacuum dryer for drying to reduce residual solvents to a level of less than about 5000 ppm. During post-drying, the jacket temperature was kept at 60° C. for the first 8 hours and then increased to 80° C.

XPRD Analysis:

The XRPD patterns were acquired with either a Bruker D8 Discover or Bruker D8 Advance diffractometer. The Bruker D8 Advance system was used to characterize the starting materials and the results of the slurry experiments in the MEK/water solvent system in the presence of the polymeric additives that include hyromellose acetate succinate (HPMCAS), and sodium lauryl sulfate (SLS) Fischer Scientific. The Bruker D8 Discover system was used for all other XRPD acquisitions. All XRPD diffractograms were evaluated using DIFFRAC$^{plus}$ released 2006, EVA version 12.0 revision 0 software.

Bruker D8 Advance System:

The XRPD patterns were recorded at room temperature in reflection mode using a Bruker D8 Advance diffractometer equipped with a sealed tube Cu source and a Vantec PSD detector (Bruker AXS, Madison, Wis.). The X-ray generator was operating at a voltage of 40 kV and a current of 40 mA. The powder sample was placed in a silicon or PMM holder. The data were recorded in a θ-θ scanning mode over the range of 4°-45° 2θ with a step size of 0.014° and a dwell time of 1 s per step. Fixed divergence slits of 0.2 mm were used.

Bruker D8 Discover System:

The XRPD patterns were acquired at room temperature in reflection mode using a Bruker D8 Discover diffractometer equipped with a sealed tube source and a Hi-Star area detector (Bruker AXS, Madison, Wis.). The X-Ray generator was operating at a voltage of 40 kV and a current of 35 mA. The powder sample was placed in an aluminum holder. Two frames were registered with an exposure time of 120 s each. The data were subsequently integrated over the range of 4°-40° 2θ with a step size of 0.02° and merged into one continuous pattern.

Thermogravimetric Analysis (TGA):

TGA was conducted on a TA Instruments model Q5000 V3.8 thermogravimetric analyzer. Approximately 1-4 mg of solid sample was placed in a platinum sample pan and heated in a 90 mL/min nitrogen stream at 10° C./min to 300° C. All thermograms were analyzed using TA Instruments Universal Analysis 2000 software V4.4A.

Single-Crystal Analysis:

Single crystal diffraction was performed on a Bruker APEX II CCD diffractometer, with Cu Kα radiation by using single crystals picked from mother liquors and mounted on glass fibers. Oscillation photos were taken around u axis at 4 φ angles. The data were indexed, integrated, and scaled with APEX software. The structures were solved and refined with the SHELX-TL package. The data collection was performed at a temperature of 100 Kelvin.

Polymorph Screening

A polymorph screen was conducted in the methylethyl ketone (MEK)/water solvent systems, as well as in the acetonitrile (ACN), ACN/water and isopropyl acetate solvent systems. Polymorph screening techniques included crash cooling, solvent evaporation, antisolvent addition, and slurry experiments. A range of solvent ratios were investigated for each technique and are listed in Tables 1A, 1B, 9, 12 and 14. Slurry experiments were performed on an IKA RCT hot plate with magnetic stirring set to 710 rpm. The temperature was controlled with an IKA ETS-D5 thermocouple. Solvent volumes were measured and transferred with Gibson Pipetteman volumetric pipettes. New forms that were identified as solvates were subjected to desolvation under two potential conditions: (1) drying in a vacuum oven at 40° C. and (2) sitting undisturbed under ambient conditions in a fume hood. Physical characterization of all forms proceeded by X-ray powder diffraction (XRPD) and thermogravimetric analysis (TGA).

Experiment 1

Crash Cooling

A saturated solution of Compound 1, Form XX was made by preparing 1 mL slurries using acetonitrile (ACN), ACN-water (75:25), methylethyl ketone (MEK), or MEK-water (99:1, 90:10, or 80:20) in vials. After 24 hours in capped HPLC vials, the slurries were then filtered to remove residual solids. Approximately 2 additional milligrams of Compound 1 was added to each vial containing a saturated solution. Next, the vials were heated to 70° C. with stirring until all of the material was completely dissolved. Immediately after, the samples were submerged into an ice bath. The product, which precipitated as a white powder within 1 minute, was isolated by filtration and analyzed by XRPD and TGA.

The results of the crash cooling experiments are listed in Table 1A.

TABLE 1A

Crash Cooling Results.

| Solvent System | Solvate Polymorph |
|---|---|
| Acetonitrile | Form D |
| Acetonitrile/H$_2$O | Form D |
| MEK | Form E |
| MEK/H$_2$O (99:1) | Form E |
| MEK/H$_2$O (90:10) | Form E |
| MEK/H$_2$O (80:20) | Form E |
| Water | not soluble |

A white powder precipitated from the ACN and ACN/water samples within a few seconds of submerging the heated samples in an ice bath. XRPD analysis of the ACN and ACN/Water samples showed the same unique powder patterns indicating that both solvent systems produce isostructural forms. TGA showed a weight loss of 1.3% upon heating to 200° C. (FIG. 3). Additionally, the weight loss began immediately upon heating in the TGA (at 27° C.), indicating that the solvent is likely loosely bound in the lattice. As a consequence the precipitate was determined to be a new form of Compound 1, designated as Form D, on the basis of its unique XRPD pattern. Form D is likely a solvate based on the TGA data. The peak list for Form D is provided in Table 2. In some embodiments, Form D is characterized by one or more peaks in an XRPD spectrum selected from the peaks listed in Table 2.

TABLE 2

Form D Peak List

| Peak Number | Angle (2-theta ± 0.2) | Intensity (%) |
|---|---|---|
| 1 | 5.6 | 100.0 |
| 2 | 6.0 | 41.5 |
| 3 | 7.8 | 9.4 |
| 4 | 13.5 | 6.8 |
| 5 | 14.1 | 7.5 |
| 6 | 14.7 | 6.9 |
| 7 | 16.2 | 9.7 |

A white powder also precipitated from MEK and MEK/water solvent systems within a few seconds of submerging the heated samples in an ice bath. XRPD analysis showed the same unique powder patterns (see, e.g., FIG. 4) for the MEK and all MEK/water ratio samples, indicating that all four solvent systems produce the same isostructural form upon crash cooling regardless of water concentration. TGA of the precipitate showed a 4.8% weight loss upon heating to 200° C. (FIG. 5). The precipitate was thus determined to be a new form of Compound I, designated Form E, on the basis of its unique XRPD pattern. Form E is likely a solvate based on the TGA data. The peak list for Form E is provided in Table 3. In some embodiments, Form E is characterized by one or more peaks in an XRPD spectrum selected from the peaks listed in Table 3.

TABLE 3

Form E Peak List

| Peak Number | Angle (2-theta ± 0.2) | Intensity (%) |
|---|---|---|
| 1 | 6.8 | 32.4 |
| 2 | 8.0 | 33.4 |
| 3 | 8.6 | 34.1 |
| 4 | 10.1 | 61.4 |
| 5 | 10.7 | 61.0 |
| 6 | 11.0 | 100.0 |
| 7 | 11.9 | 41.8 |
| 8 | 12.9 | 27.1 |
| 9 | 14.0 | 29.1 |
| 10 | 15.9 | 31.6 |
| 11 | 16.5 | 35.2 |
| 12 | 17.1 | 34.1 |
| 13 | 18.1 | 39.6 |
| 14 | 20.2 | 19.7 |
| 15 | 21.1 | 11.4 |
| 16 | 23.8 | 17.3 |
| 17 | 24.3 | 23.9 |
| 18 | 24.7 | 22.8 |
| 19 | 25.5 | 20.9 |
| 20 | 26.6 | 25.7 |

Experiment 2

Solvent Evaporation

A saturated solution was made by slurrying Compound 1, Form XX in 5 mL of solvent (ACN, isopropyl acetate (IPAc), or MEK) or 1 mL of solvent for the MEK/Water solvent system. After 24 hours, the residual solids were removed by filtration. The saturated solutions were then subjected to rapid solvent evaporation by blowing nitrogen (N$_2$) gas over the samples with a Pierce Model 18780 Reacti-Vap evaporating unit for four hours. The product precipitated as a white powder and the form was analyzed by XRPD and TGA.

The results of the Solvent Evaporation experiment are listed in Table 1B.

TABLE 1B

Solvent Evaporation Results.

| Solvent System | Solvent Evaporation |
|---|---|
| Acetonitrile/H$_2$O | Form F |
| IPAc | Form G |
| | Semi-crystalline |
| IPAc/H$_2$O | Form H |
| MEK | Form I |
| MEK/H$_2$O (99:1) | Form J |
| MEK/H$_2$O (90:10) | Form E |
| MEK/H$_2$O (80:20) | Form E |
| Water | not soluble |

Figure 1:
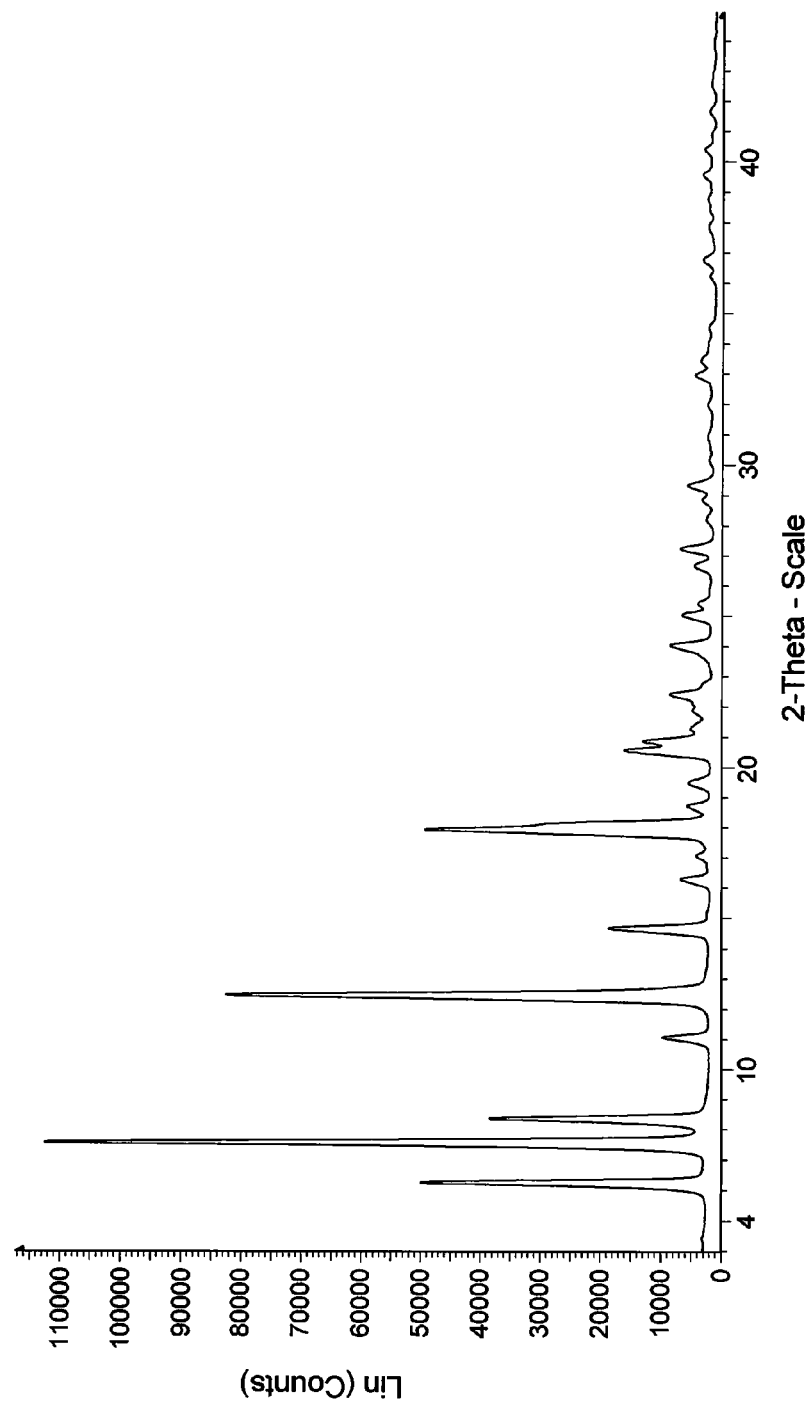
FIG. 1 is an XRPD pattern of Form XX of Compound 1.

A white powder precipitated from the ACN and ACN/water samples upon solvent evaporation. XRPD analysis of the powder collected from the ACN sample is consistent with the powder pattern of neat crystalline Compound, Form XX (FIG. 1).

The powder isolated from the ACN/water sample yielded a unique XRPD pattern indicating precipitation of a new form (FIG. 6). TGA showed a 3.1% weight loss upon heating to 200° C., consistent with solvate formation (FIG. 7). The precipitate from the ACN/water solvent system evaporation was determined to be a new form of Compound 1, designated Form F, on the basis of its unique XRPD pattern. Form F is likely a solvate based on the TGA data. The peak list for Form F is provided in Table 4. In some embodiments, Form F is characterized by one or more peaks in an XRPD spectrum selected from the peaks listed in Table 4.

TABLE 4

Form F Peak List.

| Peak Number | Angle (2-theta ± 0.2) | Intensity (%) |
| --- | --- | --- |
| 1 | 7.2 | 55.3 |
| 2 | 7.8 | 56.5 |
| 3 | 9.4 | 100.0 |
| 4 | 10.7 | 50.4 |
| 5 | 11.7 | 52.6 |
| 6 | 12.1 | 65.0 |
| 7 | 12.8 | 56.4 |
| 8 | 13.2 | 55.7 |
| 9 | 14.1 | 75.6 |
| 10 | 14.7 | 63.1 |
| 11 | 15.6 | 38.5 |
| 12 | 17.0 | 41.4 |
| 13 | 18.3 | 39.3 |
| 14 | 18.9 | 42.7 |
| 15 | 20.0 | 27.1 |
| 16 | 20.6 | 30.0 |
| 17 | 21.3 | 20.6 |
| 18 | 25.5 | 39.5 |
| 19 | 26.0 | 33.8 |
| 20 | 27.4 | 32.4 |

A white powder precipitated from the IPAc and IPAc/water samples upon solvent evaporation. Each sample produced a separate unique XRPD pattern indicating that different forms of Compound 1 were produced from IPAc and water saturated IPAc upon solvent evaporation (FIGS. 8 and 10). TGA showed a 2.3% weight loss upon heating the form precipitated from IPAc to 200° C., which is attributed to loss of solvent (FIG. 9). TGA of the form precipitated from water saturated IPAc resulted in an 11.6% weight loss upon heating to 200° C., which is attributed to loss of solvent and a further 1.8% step-wise weight loss between 200° C. and 250° C. (FIG. 11). As a consequence, each of the unique forms were determined to be new forms of Compound 1 designated as Form G from IPAc and Form H from IPAc/water on the basis of the unique XRPD patterns. Form G and Form H are likely solvates based on the TGA results. The peak list for Form G is provided in Table 5. In some embodiments, Form G is characterized by one or more peaks in an XRPD spectrum selected from the peaks listed in Table 5.

TABLE 5

Form G Peak List

| Peak Number | Angle (2-theta ± 0.2) | Intensity (%) |
| --- | --- | --- |
| 1 | 6.3 | 69.6 |
| 2 | 7.3 | 100.0 |
| 3 | 12.4 | 79.1 |

The peak list for Form H is provided in Table 6. In some embodiments, Form H is characterized by one or more peaks in an XRPD spectrum selected from the peaks listed in Table 6.

TABLE 6

Form H Peak List

| Peak Number | Angle (2-theta ± 0.2) | Intensity (%) |
| --- | --- | --- |
| 1 | 5.9 | 20.1 |
| 2 | 7.9 | 64.1 |

TABLE 6-continued

Form H Peak List

| Peak Number | Angle (2-theta ± 0.2) | Intensity (%) |
| --- | --- | --- |
| 3 | 9.9 | 100.0 |
| 4 | 10.4 | 69.7 |
| 5 | 10.9 | 38.4 |
| 6 | 11.6 | 43.3 |
| 7 | 12.1 | 50.4 |
| 8 | 13.2 | 35.9 |
| 9 | 13.8 | 37.3 |
| 10 | 14.8 | 66.8 |
| 11 | 16.0 | 52.8 |
| 12 | 17.4 | 38.1 |
| 13 | 17.9 | 40.6 |
| 14 | 19.6 | 34.5 |
| 15 | 20.6 | 33.1 |
| 16 | 21.6 | 14.1 |
| 17 | 22.5 | 17.2 |
| 18 | 23.8 | 17.7 |
| 19 | 24.8 | 35.7 |
| 20 | 26.9 | 25.3 |

A white powder precipitated from the MEK and MEK/water solvent systems upon solvent evaporation. XRPD analysis of the powder collected from the MEK/Water (90:10) and MEK/Water (80:20) samples yielded a powder pattern that matches the powder pattern of Form E (FIG. 4). Isostructural forms are thus produced from crash cooling Compound 1 from MEK and MEK/water and rapid solvent evaporation from MEK/water (90:10) and MEK/water (80:20).

The powder harvested from the MEK and MEK/water (99:1) samples produced two unique XRPD patterns, indicating the precipitation of two new forms (FIGS. 12 and 14). TGA showed a 6.2% weight loss upon heating the form precipitated from MEK out to 250° C., which is attributed to loss of solvent (FIG. 13). TGA of the form precipitated from MEK/water (99:1) shows a 3.5% weight loss upon heating to 200° C., and a further 3.7% loss between 200° C. and 275° C., both losses of which are attributed to loss of solvent (FIG. 15). As a consequence, the forms precipitated from MEK and MEK/Water (99:1) were determined to be new forms of Compound 1, designated as Form I from MEK and Form J from MEK/water (99:1) on the basis of the unique XRPD patterns. Form I and Form J are likely solvates based on the TGA results. The peak list for Form I is provided in Table 7. In some embodiments, Form I is characterized by one or more peaks in an XRPD spectrum selected from the peaks listed in Table 7.

TABLE 7

Form I Peak List

| Peak Number | Angle (2-theta ± 0.2) | Intensity (%) |
| --- | --- | --- |
| 1 | 5.8 | 49.0 |
| 2 | 6.8 | 92.8 |
| 3 | 7.2 | 47.5 |
| 4 | 8.4 | 100.0 |
| 5 | 8.8 | 51.2 |
| 6 | 9.4 | 49.4 |
| 7 | 10.2 | 54.8 |
| 8 | 11.4 | 50.2 |
| 9 | 12.7 | 41.3 |
| 10 | 13.7 | 48.3 |
| 11 | 14.8 | 44.8 |
| 12 | 15.7 | 45.4 |
| 13 | 17.1 | 53.6 |
| 14 | 17.8 | 54.2 |
| 15 | 18.3 | 64.3 |

TABLE 7-continued

Form I Peak List

| Peak Number | Angle (2-theta ± 0.2) | Intensity (%) |
|---|---|---|
| 16 | 18.8 | 61.4 |
| 17 | 20.2 | 27.4 |
| 18 | 21.3 | 25.8 |
| 19 | 23.9 | 21.2 |
| 20 | 25.2 | 30.4 |

The peak list for Form J is provided in Table 8. In some embodiments, Form J is characterized by one or more peaks in an XRPD spectrum selected from the peaks listed in Table 8.

TABLE 8

Form J Peak List

| Peak Number | Angle (2-theta ± 0.2) | Intensity (%) |
|---|---|---|
| 1 | 6.0 | 89.0 |
| 2 | 6.8 | 37.7 |
| 3 | 7.9 | 78.6 |
| 4 | 8.4 | 42.3 |
| 5 | 8.8 | 100.0 |
| 6 | 9.9 | 85.4 |
| 7 | 11.8 | 93.8 |
| 8 | 12.6 | 31.3 |
| 9 | 13.6 | 41.9 |
| 10 | 15.7 | 73.9 |
| 11 | 16.7 | 41.0 |
| 12 | 17.7 | 93.7 |
| 13 | 18.0 | 95.0 |
| 14 | 18.5 | 78.4 |
| 15 | 19.3 | 73.7 |
| 16 | 20.7 | 50.7 |
| 17 | 22.6 | 23.3 |
| 18 | 26.8 | 44.7 |
| 19 | 29.4 | 22.5 |

Experiment 3

Antisolvent Addition

A saturated solution of Compound 1, Form XX was made by slurrying either in 5 mL of solvent in the ACN, IPAc, and MEK solvent systems, 2 mL total solvent for IPAc/water, or 1 mL total solvent for the MEK/water solvent systems. After 24 hours, the residual solids were removed by filtration. 20 mL of antisolvent was then quickly added to the saturated solutions to induce precipitation. Hexane was used as the antisolvent in the MEK and IPAc solvent systems, and MTBE was used as the antisolvent in the ACN solvent systems, as a consequence of the immiscibility between ACN and hexane. The product precipitated as a white powder and the form was analyzed by XRPD and TGA. The results of rapid antisolvent addition into saturated solutions of Compound 1 are listed in Table 9.

TABLE 9

Antisolvent Addition

| Solvent System | Antisolvent Addition |
|---|---|
| IPAc/H$_2$O | Form T |
| MEK | Form K |
| MEK/H$_2$O (99:1) | Form K |
| MEK/H$_2$O (90:10) | Form K |

TABLE 9-continued

Antisolvent Addition

| Solvent System | Antisolvent Addition |
|---|---|
| MEK/H$_2$O (80:20) | Form K |
| Water | not soluble |

A precipitate was not initially obtained from hexane antisolvent addition into a saturated solution of Compound 1 in IPAc. A precipitate was not initially obtained from hexane antisolvent addition into a saturated solution of Compound 1 in IPAc/water. The clear solution was allowed to stand in a capped vial for several days after which clear rod shaped single crystals grew at the bottom of the vial. The single crystal structure solution showed a centrosymmetric structure with space group C2/c. Disordered solvent was apparent within pockets and propagated through channels in the structure. The degree of disorder was such that no attempt was made to assign the atom identities and so the solvent was simply modeled as disordered electron density. TGA of the single crystals resulted in a 0.4% weight loss upon heating to 100° C. with a further 4.8% weight loss between 100° C. and 200° C. as a result of desolvation (FIG. 35). Simulation of the XRPD pattern from the single crystal data resulted in a unique pattern (FIG. 34). As a consequence the form that was obtained as single crystals from hexane addition to a saturated solution of Compound 1 in IPAc/Water was ultimately designated as Form T on the basis of the single crystal structure solution and TGA data. The peak list for Form T is provided in Table 10. In some embodiments, Form T is characterized by one or more peaks in an XRPD spectrum selected from the peaks listed in Table 10.

TABLE 10

Form T Peak List.

| Peak Number | Angle (2-theta ± 0.2) | Intensity (%) |
|---|---|---|
| 1.0 | 4.9 | 100.0 |
| 2.0 | 7.8 | 6.3 |
| 3.0 | 8.3 | 17.3 |
| 4.0 | 8.5 | 17.2 |
| 5.0 | 9.8 | 29.8 |
| 6.0 | 11.6 | 16.7 |
| 7.0 | 14.2 | 7.4 |
| 8.0 | 15.2 | 10.8 |
| 9.0 | 15.7 | 10.8 |
| 10.0 | 17.3 | 7.4 |
| 11.0 | 18.1 | 11.1 |
| 12.0 | 18.7 | 17.0 |
| 13.0 | 19.9 | 10.3 |
| 14.0 | 21.1 | 12.3 |
| 15.0 | 21.3 | 10.4 |
| 16.0 | 23.0 | 6.8 |
| 17.0 | 23.7 | 15.5 |
| 18.0 | 24.0 | 25.8 |
| 19.0 | 25.0 | 4.4 |
| 20.0 | 25.6 | 5.6 |

A white powder instantly precipitated from the MEK and MEK/water solvent systems upon hexane addition. XRPD analysis of the precipitate collected from the MEK, MEK/Water (99:1), MEK/Water (90:10) and MEK/Water (80:20) resulted in the same unique powder pattern for all four solvent system samples (See, e.g., FIG. 16). All four solvent systems produced the same isostructural form upon antisolvent addition, regardless of water concentration. TGA of the precipitate showed a 13.4% weight loss upon heating to 175° C., attributable to loss of solvent and a further 1.3% weight loss between 175° C. and 200° C. (FIG. 17). As a consequence, the form obtained from antisolvent addition into saturated solutions of Compound 1 in the MEK and MEK/Water solvent systems was determined to be a new form of Compound 1 designated Form K on the basis of its unique XRPD pattern. Form K is likely a solvate judging from TGA. The peak list for Form K is provided in Table 11. In some embodiments, Form K is characterized by one or more peaks in an XRPD spectrum selected from the peaks listed in Table 11.

TABLE 11

Form K Peak List.

| Peak Number | Angle (2-theta ± 0.2) | Intensity (%) |
| --- | --- | --- |
| 1 | 8.0 | 21.2 |
| 2 | 8.5 | 11.1 |
| 3 | 10.0 | 100.0 |
| 4 | 11.8 | 24.1 |
| 5 | 12.3 | 7.1 |
| 6 | 14.2 | 11.1 |
| 7 | 14.8 | 6.9 |
| 8 | 15.4 | 15.5 |
| 9 | 15.9 | 11.9 |
| 10 | 16.9 | 11.7 |
| 11 | 18.0 | 16.7 |
| 12 | 18.5 | 8.7 |
| 13 | 19.8 | 7.8 |
| 14 | 20.2 | 3.5 |
| 15 | 20.7 | 3.7 |
| 16 | 21.0 | 4.1 |
| 17 | 21.5 | 2.5 |
| 18 | 22.7 | 1.3 |
| 19 | 29.5 | 5.7 |

Experiment 4

Slurry Experiments with Neat Amorphous Compound 1

The slurry experiments were carried out using neat amorphous compound 1 in 1 mL of total solvent in capped HPLC vials at 25° C. and 70° C. for either 24 hours or 2 weeks. The XRPD patterns of the resulting solids were acquired with either a Bruker D8 Discover or Bruker D8 Advance diffractometer. The results of neat Compound 1 slurry experiments are listed in Table 12.

TABLE 12

Slurry Experiments Using Neat, Amorphous Compound 1

| Solvent System | Slurry 24 hours 25° C. | Slurry 2 weeks 25° C. | Slurry 24 hours 70° C. | Slurry 2 weeks 70° C. |
| --- | --- | --- | --- | --- |
| Acetonitrile | Form XX | Form XX | Form XX | Form XX |
| Acetonitrile/H$_2$O | Form XX | Form XX | Form XX | Form XX |
| IPAc | Form XX | Form XX | Form XX | Form XX |
| IPAc/H$_2$O | Form L | Form L | Form XX | Form XX |
| MEK | Form XX | Form XX | Form XX | Form XX |
| MEK/H$_2$O (99:1) | Form XX | Form XX | Form XX | Form XX |
| MEK/H$_2$O (90:10) | Form E | Form E | Form XX | Form XX |
| MEK/H$_2$O (80:20) | Form E | Form E | Form XX | Form XX |
| Water | Hydrate | Hydrate | Hydrate | Form XX |

A white powder was collected by filtration from 24 hour and 2 week slurry experiments conducted at 25° C. and 70° C. in ACN and ACN/water. XRPD analysis of the samples results in peaks consistent with neat crystalline Form XX. When neat amorphous Compound 1 was slurried for 24 hours and 2 weeks in ACN and ACN/water at 25° C. and 70° C. neat Form XX was produced.

A white powder was collected by filtration from 24 hour and 2 week slurry experiments conducted at 25° C. and 70° C. in IPAc and IPAc/water. XRPD analysis of the powder collected from the IPAc and IPAc/water samples slurried at 70° C. and IPAc slurried at 25° C. results in peaks consistent with neat crystalline Form XX. When neat amorphous Compound 1 was slurried for 24 hours and 2 weeks in IPAc and IPAc/water at 70° C. and in IPAc for 24 hours and 2 weeks at 25° C., neat Form XX was produced. The powder harvested from samples slurried in IPAc/water at 25° C. for 24 hours and 2 weeks resulted in the same unique XRPD pattern for these two samples, indicating the precipitation of isostructural forms. TGA of the precipitate showed a 14.1% weight loss upon heating to 200° C., attributable to loss of solvent with a further 0.8% weight loss between 200° C. and 250° C. (FIG. 19). The powder harvested at 24 hours and 2 weeks after slurrying neat amorphous Compound 1 in IPAc/water at 25° C. and 70° C. is determined to be a new form of Compound 1 designated Form L (FIG. 18). Form L is likely a solvate based on the TGA results. The peak list for Form L is provided in Table 13. In some embodiments, Form L is characterized by one or more peaks in an XRPD spectrum selected from the peaks listed in Table 13.

TABLE 13

Form L Peak List

| Peak Number | Angle (2-theta ± 0.2) | Intensity (%) |
| --- | --- | --- |
| 1 | 7.9 | 63.6 |
| 2 | 10.0 | 77.1 |
| 3 | 10.4 | 100.0 |
| 4 | 10.9 | 57.5 |
| 5 | 12.1 | 94.1 |
| 6 | 13.2 | 36.0 |
| 7 | 13.8 | 41.1 |
| 8 | 14.8 | 52.9 |
| 9 | 16.0 | 49.6 |
| 10 | 16.9 | 27.2 |
| 11 | 17.4 | 31.7 |
| 12 | 18.6 | 63.6 |
| 13 | 19.7 | 35.9 |
| 14 | 20.5 | 49.8 |
| 15 | 21.6 | 21.2 |
| 16 | 22.1 | 21.1 |
| 17 | 22.5 | 32.0 |
| 18 | 24.8 | 35.3 |
| 19 | 25.2 | 34.0 |

A white powder was collected by filtration from the 24 hour and 2 week slurry experiments conducted at 25° C. and 70° C. in MEK, MEK/water (99:1), MEK/water (90:10) and MEK/water (80:20). XRPD analysis of the powder collected from MEK/Water (90:10) and MEK/Water (80:20) samples at 25° C. after 24 hours and 2 weeks yielded a powder pattern that matched the powder pattern of Form E, indicating the precipitation of isostructural forms. The powder collected from MEK/water (90:10) and MEK/water (80:20) slurried at 70° C. yielded XRPD patterns consistent with neat crystalline Form XX. Slurrying of neat amorphous Compound 1 in MEK/water (90:10) and MEK/water (80:20) for 24 hours and 2 weeks produced Form XX at 70° C. and Form E at 25° C. In contrast, the powder collected from slurrying neat amorphous Compound 1 in the solvent systems with lower water content—MEK and MEK/water (99:1)—produced only neat crystalline Form XX as determined from their XRPD patterns at 25° C. and 70° C. after 24 hours and 2 weeks.

A white powder was collected by filtration from 24 hour and 2 week slurry experiments conducted at 25° C. and 70° C. in water. XRPD analysis of the powder collected from samples slurried at 25° C. for 24 hours and 2 weeks in water resulted in powder patterns consistent with the known form of Hydrate A of Compound 1. XRPD analysis of the powder collected from samples slurried at 70° C. demonstrated Compound 1, Hydrate A formation after 24 hours and Compound 1, Form XX after 2 weeks. When neat amorphous Compound 1 was slurried in water at 25° C., Hydrate A was formed. When it was slurried at 70° C., Hydrate A was observed after 24 hours and Form XX was observed after 2 weeks.

Experiment 5

Slurry Experiments with Compound 1 Spray-Dried Dispersion in the Presence of HPMC-AS and SLS Spray dried dispersion containing amorphous Compound 1, along with the polymeric additives HPMC-AS (Hovione) and sodium lauryl sulfate (SLS, Fischer Scientific), was used for the slurry experiments in ACN/water and IPAc/water MEK/water solvent system in the methyl ethyl ketone/water solvent systems. The experiments were carried out in 1 mL of total solvent in capped HPLC vials at 25° C. and 70° C. for either 24 hours or 2 weeks. The XRPD patterns of the resulting solids were acquired with either a Bruker D8 Discover or Bruker D8 Advance diffractometer. The results of these slurry experiments with HPMC-AS and SLS are listed in Table 14.

TABLE 14

Slurry Experiments with Spray Dried Dispersion Containing Amorphous Compound 1 in the Presence of the Polymeric Additives HPMC-AS and SLS.

| Solvent System | Slurry 24 hours 25° C. | Slurry 2 weeks 25° C. | Slurry 24 hours 70° C. | Slurry 2 weeks 70° C. |
|---|---|---|---|---|
| MEK | Form M | Form M | Form O | Form O |
| MEK/H2O (99:1) | Form M | Form M | Form O | Form XX |
| MEK/H2O (90:10) | Form N | Form N | Form P | Form XX |
| MEK/H2O (80:20) | Form N | Form N | Form P | Form Q |

A white powder was collected by filtration from the 24 hour and 2 week slurry experiments conducted at 25° C. and 70° C. in MEK, MEK/water (99:1), MEK/water (90:10) and MEK/water (80:20). Analysis of the powder collected from samples slurried in MEK and MEK/water (99:1) at 25° C. for 24 hours and 2 weeks yielded the same unique XRPD pattern for all four samples, indicating the synthesis of isostructural forms (FIG. 20). TGA of the precipitate showed a 1.2% weight loss upon heating to 100° C. and a further 11.3% weight loss upon further heating between 100° C. and 200° C., attributable to loss of solvent (FIG. 21). As such, the powder collected from samples slurried in MEK and MEK/water (99:1) at 25° C. for 24 hours and 2 weeks is determined to be a new form of Compound 1 designated Form M. Form M is likely a solvate based on the TGA results. The peak list for Form M is provided in Table 15. In some embodiments, Form M is characterized by one or more peaks in an XRPD spectrum selected from the peaks listed in Table 15.

TABLE 15

Form M Peak List.

| Peak Number | Angle (2-theta ± 0.2) | Intensity (%) |
|---|---|---|
| 1 | 5.2 | 77.3 |
| 2 | 6.0 | 55.5 |
| 3 | 6.9 | 100.0 |
| 4 | 8.0 | 33.4 |
| 5 | 8.9 | 40.1 |
| 6 | 10.7 | 93.6 |
| 7 | 12.3 | 53.6 |
| 8 | 13.0 | 33.7 |
| 9 | 13.5 | 29.2 |
| 10 | 14.4 | 36.2 |
| 11 | 16.8 | 35.1 |
| 12 | 17.3 | 43.2 |
| 13 | 17.6 | 47.3 |
| 14 | 18.3 | 55.0 |
| 15 | 18.7 | 53.8 |
| 16 | 19.8 | 35.9 |
| 17 | 20.4 | 28.6 |
| 18 | 21.1 | 40.5 |
| 19 | 22.0 | 40.5 |
| 20 | 23.4 | 39.1 |

Increasing the water content in the solvent system to MEK/water (90:10) and MEK/water (80:20) in slurries carried out at 25° C. produced a different form from MEK and MEK/Water (99:1) as judged from XRPD analysis at 24 hour and 2 week time points. The same XRPD pattern was produced from MEK/water (90:10) and MEK/water (80:20) slurries after 24 hours and 2 weeks at 25° C., indicating the precipitation of new isostructural forms (FIG. 22). TGA of the precipitate resulted in a 1.0% weight loss upon heating to 75° C. and a further 3.7% weight loss upon heating between 100° C. and 200° C. (FIG. 23). As a consequence, the powder collected from samples slurried in MEK/water (90:10) and MEK/water (80:20) at 25° C. for 24 hours and 2 weeks was determined to be a new form of Compound 1 designated Form N. Form N is likely a solvate based on the TGA results. The peak list for Form N is provided in Table 16. In some embodiments, Form N is characterized by one or more peaks in an XRPD spectrum selected from the peaks listed in Table 16.

TABLE 16

Form N Peak List.

| Peak Number | Angle (2-theta ± 0.2) | Intensity (%) |
|---|---|---|
| 1 | 6.4 | 20.4 |
| 2 | 7.6 | 26.5 |
| 3 | 8.2 | 56.8 |
| 4 | 9.1 | 27.2 |
| 5 | 9.7 | 63.3 |
| 6 | 10.2 | 47.3 |
| 7 | 10.6 | 100.0 |
| 8 | 11.5 | 48.2 |
| 9 | 12.4 | 41.6 |
| 10 | 14.1 | 18.4 |
| 11 | 15.4 | 23.1 |
| 12 | 16.6 | 49.2 |
| 13 | 17.0 | 37.3 |
| 14 | 17.6 | 35.1 |
| 15 | 18.8 | 31.9 |
| 16 | 21.4 | 26.0 |
| 17 | 23.3 | 30.8 |
| 18 | 23.8 | 34.5 |
| 19 | 24.2 | 17.0 |
| 20 | 25.7 | 21.8 |

Slurry experiments conducted at 70° C. on a spray dried dispersion containing amorphous Compound 1 in the presence of HPMC-AS and SLS yielded different results from those conducted at 25° C., as provided in Table 12. Analysis of the powder diffraction patterns of spray dried dispersion containing amorphous Compound 1 slurried in MEK at 70° C. showed the same unique XRPD pattern at the 24 hour and 2 week time points, indicating precipitation of the same new form (FIG. 24). TGA of the precipitate showed a weight loss of 0.8% upon heating to 150° C. and a further 2.0% weight loss upon heating between 150° C. and 200° C. (FIG. 25). The powder collected from the 24 hour and 2 week slurries at 70° C. in MEK was determined to be a new form of Compound 1 designated Form O. The peak list for Form O is provided in Table 17. In some embodiments, Form O is characterized by one or more peaks in an XRPD spectrum selected from the peaks listed in Table 17.

TABLE 17

Form O Peak List

| Peak Number | Angle (2-theta ± 0.2) | Intensity (%) |
|---|---|---|
| 1 | 5.7 | 100.0 |
| 2 | 7.5 | 41.1 |
| 3 | 8.5 | 88.1 |
| 4 | 9.5 | 62.5 |
| 5 | 11.4 | 67.9 |
| 6 | 13.2 | 22.7 |
| 7 | 15.3 | 55.0 |
| 8 | 16.3 | 21.5 |
| 9 | 17.2 | 64.5 |
| 10 | 17.5 | 63.2 |
| 11 | 18.0 | 42.3 |
| 12 | 18.9 | 52.3 |
| 13 | 20.3 | 43.4 |
| 14 | 20.6 | 25.4 |
| 15 | 22.2 | 68.3 |
| 16 | 23.1 | 15.7 |
| 17 | 23.5 | 17.7 |
| 18 | 26.4 | 31.1 |

XRPD of a spray dried dispersion containing amorphous Compound 1 with HPMC-AS and SLS slurried in MEK/water (99:1) at 70° C. yielded a diffraction pattern consistent with Form O after 24 hours and a diffraction pattern consistent with Form XX after 2 weeks. XRPD of a spray dried dispersion containing amorphous Compound 1 slurried in MEK/water (90:10) at 70° C. yielded a unique diffraction pattern after 24 hours, indicating the synthesis of a new form of Compound 1 (FIG. 26), designated Form P and a diffraction pattern consistent with Form XX after 2 weeks. TGA of Form P showed a 2.4% weight loss upon heating to 100° C. with a further 4.7% weight loss upon heating between 100° C. and 200° C., indicating that Form P is likely a solvate (FIG. 27). The peak list for Form P is provided in Table 18. In some embodiments, Form P is characterized by one or more peaks in an XRPD spectrum selected from the peaks listed in Table 18.

TABLE 18

Form P Peak List

| Peak Number | Angle (2-theta ± 0.2) | Intensity (%) |
|---|---|---|
| 1 | 6.1 | 38.9 |
| 2 | 7.4 | 27.9 |
| 3 | 8.2 | 81.7 |
| 4 | 9.1 | 26.4 |
| 5 | 9.7 | 21.9 |
| 6 | 10.6 | 23.8 |
| 7 | 10.9 | 23.8 |
| 8 | 11.5 | 34.1 |
| 9 | 12.3 | 100.0 |

TABLE 18-continued

Form P Peak List

| Peak Number | Angle (2-theta ± 0.2) | Intensity (%) |
|---|---|---|
| 10 | 16.1 | 19.7 |
| 11 | 16.7 | 57.9 |
| 12 | 17.0 | 45.2 |
| 13 | 17.7 | 30.9 |
| 14 | 18.9 | 16.0 |
| 15 | 21.9 | 16.7 |
| 16 | 23.3 | 12.7 |
| 17 | 23.8 | 11.9 |
| 18 | 24.9 | 10.3 |
| 19 | 25.8 | 16.2 |

XRPD of a spray dried dispersion containing amorphous Compound 1 with HPMC-AS and SLS slurried in MEK/water (80:20) at 70° C. for 24 hours yielded a diffraction pattern consistent with Form P and a unique diffraction pattern after 2 weeks (FIG. 28), indicating the synthesis of a new form of Compound 1 designated Form Q. TGA of Form Q showed a 1.1% weight loss upon heating to 100° C., with a further 2.4% weight loss upon heating between 100° C. and 200° C., indicating that Form Q is likely a solvate (FIG. 29). The peak list for Form Q is provided in Table 19. In some embodiments, Form Q is characterized by one or more peaks in an XRPD spectrum selected from the peaks listed in Table 19.

TABLE 19

Form Q Peak List

| Peak Number | Angle (2-theta ± 0.2) | Intensity (%) |
|---|---|---|
| 1 | 6.3 | 34.6 |
| 2 | 7.6 | 100.0 |
| 3 | 8.4 | 25.9 |
| 4 | 11.1 | 15.4 |
| 5 | 11.7 | 9.4 |
| 6 | 12.5 | 79.0 |
| 7 | 14.7 | 14.5 |
| 8 | 16.4 | 14.8 |
| 9 | 16.9 | 21.5 |
| 10 | 17.3 | 12.9 |
| 11 | 18.0 | 79.6 |
| 12 | 18.8 | 11.0 |
| 13 | 20.6 | 11.8 |
| 14 | 21.0 | 13.0 |
| 15 | 22.2 | 11.1 |
| 16 | 24.1 | 10.7 |
| 17 | 25.1 | 11.7 |
| 18 | 27.4 | 8.4 |

Experiment 6

Desolvation

New forms of Compound 1 obtained in the polymorph screen suspected of being solvates were subjected to further form investigation through attempted desolvation. Forms D, E, F, G, H, I, J, K, L and Hydrate A were left to stand open to the atmosphere under ambient conditions and or were placed in a vacuum oven. Forms E, F, I, J and Hydrate A yielded the same XRPD patterns after standing under ambient conditions and after sitting in the vacuum oven.

Form G became x-ray amorphous after standing in the vacuum oven for one month.

Form H produced the same Form H pattern after standing under ambient conditions for one month but converted to a semi-crystalline form after standing in the vacuum oven for one month.

Form L produced the same Form L pattern after standing under ambient conditions for two weeks but converted to x-ray amorphous after standing in the vacuum oven for 24 hours.

Forms D and K produced new crystalline XRPD patterns following desolvation. XRPD analysis of Form D, after standing under ambient conditions and standing in the vacuum oven for approximately 1 month, showed a unique diffraction pattern, indicating that Form D had converted to a new crystalline form of Compound 1 designated Form R (FIG. 30). TGA of Form R showed a 2.1% weight loss upon heating to 200° C., indicating that Form R had retained some solvent (FIG. 31). The peak list for Form R is provided in Table 20. In some embodiments, Form R is characterized by one or more peaks in an XRPD spectrum selected from the peaks listed in Table 20.

TABLE 20

| Form R Peak List | | |
| --- | --- | --- |
| Peak Number | Angle (2-theta ± 0.2) | Intensity (%) |
| 1 | 6.7 | 100.0 |
| 2 | 7.7 | 15.6 |
| 3 | 13.2 | 23.0 |
| 4 | 15.1 | 16.3 |
| 5 | 17.8 | 13.9 |

XRPD analysis of Form K after standing under ambient conditions and standing in the vacuum oven for 2 months showed a unique diffraction pattern, indicating that Form K had converted to a new crystalline form of Compound 1 designated Form S (FIG. 32). TGA of Form S showed three separate weight losses. Form S underwent a 1.2% weight loss upon heating to 150° C. and a further 0.7% weight loss upon heating between 150° C. and 200° C., and finally a 1.0% weight loss upon heating between 200° C. and 250° C., indicating that Form S has retained some solvent (FIG. 33). The peak list for Form S is provided in Table 21. In some embodiments, Form S is characterized by one or more peaks in an XRPD spectrum selected from the peaks listed in Table 21.

TABLE 21

| Form S Peak List | | |
| --- | --- | --- |
| Peak Number | Angle (2-theta ± 0.2) | Intensity (%) |
| 1.0 | 4.8 | 78.1 |
| 2.0 | 5.7 | 7.9 |
| 3.0 | 7.7 | 13.7 |
| 4.0 | 8.2 | 46.7 |
| 5.0 | 8.6 | 11.3 |
| 6.0 | 9.6 | 100.0 |
| 7.0 | 11.3 | 10.4 |
| 8.0 | 11.6 | 35.4 |
| 9.0 | 12.3 | 5.9 |
| 10.0 | 13.9 | 8.7 |
| 11.0 | 15.1 | 11.0 |
| 12.0 | 15.5 | 8.1 |
| 13.0 | 15.9 | 5.4 |
| 14.0 | 16.5 | 6.6 |
| 15.0 | 17.6 | 9.8 |
| 16.0 | 18.3 | 14.6 |
| 17.0 | 19.4 | 8.3 |
| 18.0 | 19.7 | 8.8 |
| 19.0 | 20.7 | 6.3 |
| 20.0 | 23.6 | 11.6 |

Hydrate B is a hydrated form of Compound 1 made from a slurry of amorphous Compound 1 in simulated fluids (FeSSIF). The XRPD pattern for Hydrate B is given in FIG. 36. A thermogravimetric analysis spectrum (TGA) of Hydrate B is shown in FIG. 37. The peak list for Hydrate B is provided in Table 22. In some embodiments, Hydrate B is characterized by one or more peaks in an XRPD spectrum selected from the peaks listed in Table 22.

TABLE 22

| Hydrate B Peak List | | |
| --- | --- | --- |
| Peak Number | Angle (2-theta ± 0.2) | Intensity (%) |
| 1 | 4.9 | 100.0 |
| 2 | 6.0 | 25.6 |
| 3 | 7.2 | 12.9 |
| 4 | 8.9 | 15.2 |
| 5 | 10.1 | 12.8 |
| 6 | 10.7 | 11.5 |
| 7 | 11.3 | 11.5 |
| 8 | 11.9 | 26.2 |

Form W is a solvated form from 10% water/90% acetonitrile. Form W is prepared by crystallization/slurry conversion of Compound 1, Form XX in 90% acetonitrile/10% water below 10 degrees Celsius. The XRPD pattern for Form W is shown in FIG. 38. A thermogravimetric analysis spectrum (TGA) of Form W overlayed with a Differential Scanning calorimetry plot (DSC) of Form W is shown in FIG. 39. The peak list for Form W is provided in Table 23.

TABLE 23

| Form W Peak List | | |
| --- | --- | --- |
| Peak Number | Angle (2-theta ± 0.2) | Intensity (%) |
| 1 | 5.5 | 100.0 |
| 2 | 5.9 | 5.4 |
| 3 | 7.6 | 4.6 |
| 4 | 10.9 | 5.3 |
| 5 | 12.1 | 7.0 |
| 6 | 13.3 | 6.2 |
| 7 | 14.6 | 7.2 |
| 8 | 17.2 | 5.3 |
| 9 | 18.8 | 4.9 |
| 10 | 21.8 | 4.7 |
| 11 | 22.5 | 4.5 |
| 12 | 23.2 | 4.3 |
| 13 | 23.7 | 4.3 |
| 14 | 25.0 | 4.7 |
| 15 | 25.6 | 4.6 |

Single Crystal Analysis of Form T:

Single Crystal Analysis was Done on a crystal of Form T as described above. The unit cell dimensions and space group were found to be:

Space Group: C2/c

Cell Lengths: a=32.5478(13), b=22.5036(9), c=22.5540 (9)

Cell Angles: α=90.00, β=112.725(2), γ=90.00

Cell Volume: 15237.1 Å

Assays

A. Protocol 1

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 (above) are substituted with gluconate salts.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at 20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 µM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, EGTA, 10 HEPES, and 240 µg/mL amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 µM forskolin and 20 µM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, ε-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dot, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 CaCl$_2$, 2 MgCl$_2$, and 10 HEPES (pH adjusted to 7.35 with Tris base). The bath contained (in mM): 150 NMDG-Cl, 2 MgCl$_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Activity of the Compound 1

Compounds of the invention are useful as modulators of ATP binding cassette transporters. Table 1-3 below illustrates the EC50 and relative efficacy of certain embodiments in Table 1. In Table 1-3 below, the following meanings apply. EC50: "+++" means <10 uM; "++" means between 10 uM to 25 uM; "+" means between 25 uM to 60 uM. % Efficacy: "+" means <25%; "++" means between 25% to 100%, "+++" means >100%.

TABLE 1-3

| Cmpd # | EC50 (uM) | % Activity |
|---|---|---|
| 1 | +++ | ++ |

B. Protocol 2

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}=0$ mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic Δ508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around –30 mV, which is the calculated $E_{Cl}$ (–28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The following clauses describe additional embodiments and/or subject matters of the present invention.

1. A process for making a crystalline solvate form of Compound 1, selected from Form D or Form E comprising:
   a) dissolving Form XX of Compound 1 in at least one solvent to form a mixture;
   b) heating the mixture until the solid has dissolved;
   c) precipitating the solid form by cooling the mixtures; and
   d) isolating the solid form.
2. The process of clause 1, wherein at least one of the solvents is acetonitrile.
3. The process of clause 1, wherein the solvent is a mixture of MEK and water, wherein the mixture is 99% MEK and 1% water, 90% MEK and 10% water, or 80% MEK and 20% water.
4. A process for making a crystalline solvate form of Compound 1, selected from Form F or Form E comprising:
   a) slurrying Form XX of Compound 1 in acetonitrile optionally containing water to form a mixture;
   b) removing residual solid from the mixture by filtration;
   c) removing the solvent by rapid evaporation; and
   d) isolating the solid form.
5. The process of clause 4, wherein the solvent is acetonitrile.
6. A process for making a crystalline solvate Form G of Compound 1 comprising:
   a) slurrying Form XX of Compound 1 in isopropyl acetate to form a mixture;
   b) removing the residual solid from the mixture by filtration;
   c) removing the solvent by rapid evaporation; and
   d) isolating the Form G.
7. A process for making a crystalline solvate Form H of Compound 1 comprising:
   a) slurrying Form XX of Compound 1 in isopropyl acetate containing water to form a mixture;
   b) removing the residual solid from the mixture by filtration;
   c) removing the solvent by rapid evaporation; and
   d) isolating the Form H.
8. The process of clause 7, wherein, the solvent is isopropyl acetate/water 95/5.
9. A process for making a crystalline solvate Form I of Compound 1 comprising:
   a) slurrying Form XX of Compound 1 in methylethyl ketone to form a mixture;
   b) removing the residual solid from the mixture by filtration;
   c) removing the solvent by rapid evaporation; and
   d) isolating the Form I.
10. A process for making a crystalline solvate Form J of Compound 1 comprising:
    a) slurrying Form XX of Compound 1 in methylethyl ketone containing water to form a mixture;
    b) removing the residual solid from the mixture by filtration;

c) removing the solvent by rapid evaporation; and
d) isolating the Form J.
11. The process of clause 10, wherein the solvent comprises MEK in an amount of about 99% and water in an amount of about 1%, MEK in an amount of about 90% and water in an amount of about 10%, or MEK in an amount of about 80% and water in an amount of about 20%.
12. A process for making a crystalline solvate Form K of Compound 1 comprising:
 a) slurrying Form XX of Compound 1 in methylethyl ketone containing 0 percent to 30 percent water to form a mixture;
 b) removing the residual solid from the mixture by filtration;
 c) adding an antisolvent to the mixture to induce precipitation; and
 d) isolating the Form K.
13. The process of clause 12, wherein the antisolvent is hexane.
14. A process for making a crystalline solvate Form L of Compound 1 comprising:
 a) slurrying amorphous Compound 1 in isopropyl acetate containing water to form a mixture;
 b) removing the residual solid from the mixture by filtration;
 c) removing the solvent by rapid evaporation; and
 d) isolating the Form L.
15. The process of clause 14, wherein the solvent comprises isopropyl acetate in an amount of about 95% and water in an amount of about 5%.
16. A process for making a crystalline solvate Form M of Compound 1 comprising:
 a) at 25° C., slurrying amorphous Compound 1 in methylethyl ketone containing 0 percent to 1 percent water for 12 hours to a month to form a mixture;
 b) removing the residual solid from the mixture by filtration; and
 c) isolating the Form M.
17. The process of clause 16, wherein the mixture further comprises one or more polymeric additives selected from HPMC and sodium lauryl sulfate.
18. A process for making a crystalline solvate Form N of Compound 1 comprising:
 a) at 25° C., slurrying amorphous Compound 1 in methylethyl ketone containing 10 percent to 20 percent water for 12 hours to a month to form a mixture;
 b) removing the residual solid from the mixture by filtration; and
 c) isolating the Form N.
19. The process of clause 18, wherein the mixture further comprises one or more polymeric additives selected from HPMC and sodium lauryl sulfate.
20. A process for making a crystalline solvate Form O of Compound 1 comprising:
 a) at 70° C., slurrying amorphous Compound 1 in methylethyl ketone containing 0 percent to 1 percent water for 12 hours to 24 hours to form a mixture;
 b) heating the mixture at approximately 70° C. for 1 to 30 hours;
 c) removing the residual solid from the mixture by filtration; and
 d) isolating the Form O.
21. The process of clause 20, wherein the mixture further comprises one or more polymeric additives selected from HPMC and sodium lauryl sulfate.
22. A process for making a crystalline solvate Form P of Compound 1 comprising:
 a) at 70° C., slurrying amorphous Compound 1 in methylethyl ketone containing 10 percent to 20 percent water for 12 to 24 hours to form a mixture;
 b) heating the mixture at approximately 70° C. for 1 to 30 hours;
 c) removing the residual solid from the mixture by filtration; and
 d) isolating the Form P.
23. The process of clause 22, wherein the mixture further comprises one or more polymeric additives selected from HPMC and sodium lauryl sulfate.
24. A process for making a crystalline solvate Form Q of Compound 1 comprising:
 a) at 70° C., slurrying amorphous Compound 1 in methylethyl ketone containing 10 percent to 20 percent water for 2 days to 3 weeks to form a mixture;
 b) heating the mixture at approximately 70° C. for 1 to 30 hours;
 c) removing the residual solid from the mixture by filtration; and
 d) isolating the Form Q.
25. The process of clause 24, wherein the mixture further comprises one or more polymeric additives selected from HPMC and sodium lauryl sulfate.
26. A process for making a crystalline solvate Form R of Compound 1 comprising:
 a) drying the Form D of Compound 1 in a vacuum oven at a temperature between room temperature and 45° C.; and
 b) isolating the Form R.
27. A process for making a crystalline solvate Form S of Compound 1 comprising:
 a) drying Form K of Compound 1 in a vacuum oven at a temperature between room temperature and 45° C.; and
 d) isolating the Form S.
28. A process for making a crystalline solvate Form T of Compound 1 comprising:
 a) slurrying Form XX of Compound 1 in methylethyl ketone containing 0 percent to 30 percent water to form a mixture;
 b) removing the residual solid from the mixture by filtration;
 c) adding an antisolvent to the mixture to induce precipitation; and
 d) isolating the Form T.
29. A crystalline solvate of Compound 1, wherein the solvent is selected from the group consisting of acetonitrile, acetonitrile/water, isopropyl acetate, isopropyl acetate/water, methylethyl ketone, and methylethyl ketone/water.
30. The crystalline solvate of clause 29, wherein the solvent is acetonitrile or acetonitrile/water and the crystalline solvate is Form D, Form F, or Form R.
31. The crystalline solvate of clause 29, wherein the solvent is isopropyl acetate or isopropyl acetate/water and the crystalline solvate is Form G, Form H, Form L, or Form T.
32. The crystalline solvate of clause 29, wherein the solvent is methylethyl ketone or methylethyl ketone/water and the crystalline solvate is Form E, Form I, Form J, Form K, Form M, Form N, Form O, Form P, or Form S.
33. A kit for use in measuring the activity of CFTR or a fragment thereof in a biological sample in vitro or in vivo, comprising:
 (i) a composition comprising crystalline solvate Form D, E, F, G, H, I, J, K, L, M, N, O, P, Q, R, S, T, W, or Hydrate B, or combinations thereof, according to claim 1, (ii) instructions for:
(a) contacting the composition with the biological sample;
(b) measuring activity of said CFTR or a fragment thereof.

34. The kit of clause 33, further comprising instructions for:
   i. contacting an additional composition with the biological sample;
   ii. measuring the activity of said CFTR, or a fragment thereof, in the presence of said additional compound; and
   iii. comparing the activity of the CFTR, or fragment thereof, in the presence of the additional compound with the density of CFTR, or fragment thereof, in the presence of a crystalline solvate Form D, E, F, G, H, I, J, K, L, M, N, O, P, Q, R, S, T, W, or Hydrate B, or combination thereof.

35. The kit of clause 34, wherein the step of comparing the activity of said CFTR, or fragment thereof, provides a measure of the density of said CFTR, or fragment thereof.

36. A process for making a crystalline solvate Form W of Compound 1 comprising:
   a) slurrying Form XX of Compound 1 in acetonitrile containing 10% water to form a mixture.
   b) removing the residual solid from the mixture by filtration; and
   c) isolating Form W.

37. A process for making a crystalline solvate Hydrate B of Compound 1 comprising:
   a) slurrying neat amorphous Compound 1 in FeSSIF to form a mixture;
   b) removing the residual solid from the mixture by filtration; and
   c) isolating Hydrate B.

What is claimed is:

1. A crystalline solvate of N-[2,4-bis(1,1-dimethylethyl)-5-hydroxyphenyl]-1,4-dihydro-4-oxoquinoline-3-carboxamide (Compound 1), wherein the crystalline solvate is designated as a solid form selected from the group consisting of Form D, Form E, Form F, Form G, Form H, Form I, Form J, Form K, Form L, Form M, Form N, Form O, Form P, Form Q, Form R, Form S, Form T, Form W, and Hydrate B, wherein Form D is an acetonitrile solvate, or an acetonitrile/water 75/25 solvate, and is characterized by the following peaks in an X-ray powder diffraction pattern: 5.6±0.2 degrees, 6.0±0.2 degrees, 7.8±0.2 degrees, 13.5±0.2 degrees, 14.1±0.2 degrees, 14.7±0.2 degrees, and 16.2±0.2 degrees;

Form E is a methylethyl ketone (MEK) solvate, a MEK/water 99/1 solvate, a MEK/water 90/10 solvate, or a MEK/water 80/20 solvate, and is characterized by the following peaks in an X-ray powder diffraction pattern: 8.0±0.2 degrees, 8.6±0.2 degrees, 10.1±0.2 degrees, 11.0±0.2 degrees, 11.9±0.2 degrees, 16.5±0.2 degrees, 17.1±0.2 degrees, and 18.1±0.2 degrees;

Form F is an acetonitrile/water 75/25 solvate, and is characterized by the following peaks in an X-ray powder diffraction pattern: 7.2±0.2 degrees, 7.8±0.2 degrees, 9.4±0.2 degrees, 10.7±0.2 degrees, 12.1±0.2 degrees, 12.8±0.2 degrees, 14.1+0.2 degrees, and 14.7±0.2 degrees;

Form G is an isopropyl acetate solvate, and is characterized by the following peaks in an X-ray powder diffraction pattern: 6.3±0.2 degrees, 7.3±0.2 degrees, and 12.4±0.2 degrees;

Form H is an isopropyl acetate/water 95/5 solvate, and is characterized by the following peaks in an X-ray powder diffraction pattern: 7.9±0.2 degrees, 9.9±0.2 degrees, 10.4±0.2 degrees, 11.6±0.2 degrees, 12.1±0.2 degrees, 14.8±0.2 degrees, 16.0±0.2 degrees, and 17.9±0.2 degrees;

Form I is a MEK solvate, and is characterized by the following peaks in an X-ray powder diffraction pattern: 6.8±0.2 degrees, 8.4±0.2 degrees, 9.4±0.2 degrees, 10.2±0.2 degrees, 11.4±0.2 degrees, 17.1±0.2 degrees, 17.8±0.2 degrees, and 18.3±0.2 degrees;

Form J is a MEK/water 99/1 solvate, and is characterized by the following peaks in an X-ray powder diffraction pattern: 6.0±0.2 degrees, 7.9±0.2 degrees, 8.8±0.2 degrees, 9.9±0.2 degrees, 11.8±0.2 degrees, 17.7±0.2 degrees, 18.0±0.2 degrees, and 18.5±0.2 degrees;

Form K is a methylethyl ketone (MEK) solvate, a MEK/water 99/1 solvate, a MEK/water 90/10 solvate, or a MEK/water 80/20 solvate, and is characterized by the following peaks in an X-ray powder diffraction pattern: 8.0±0.2 degrees, 8.5±0.2 degrees, 10.0±0.2 degrees, 11.8±0.2 degrees, 15.4±0.2 degrees, 15.9±0.2 degrees, 16.9±0.2 degrees, and 18.0±0.2 degrees;

Form L is an isopropyl acetate/water 95/5 solvate, and is characterized by the following peaks in an X-ray powder diffraction pattern: 7.9±0.2 degrees, 10.4±0.2 degrees, 10.9±0.2 degrees, 12.1±0.2 degrees, 14.8±0.2 degrees, 16.0±0.2 degrees, 18.6±0.2 degrees, and 20.5±0.2 degrees;

Form M is a methylethyl ketone (MEK) solvate or a MEK/water 99/1 solvate, and is characterized by the following peaks in an X-ray powder diffraction pattern: 5.2±0.2 degrees, 6.0±0.2 degrees, 6.9±0.2 degrees, 10.7±0.2 degrees, 12.3±0.2 degrees, 17.6±0.2 degrees, 18.3±0.2 degrees, and 21.1±0.2 degrees;

Form N is a MEK/water 90/10 solvate or a MEK/water 80/20 solvate, and is characterized by the following peaks in an X-ray powder diffraction pattern: 8.2±0.2 degrees, 9.7±0.2 degrees, 10.6±0.2 degrees, 11.5±0.2 degrees, 12.4±0.2 degrees, 16.6±0.2 degrees, 17.6+0.2 degrees, and 23.8±0.2 degrees;

Form O is a methylethyl ketone (MEK) solvate, or a MEK/water 99/1 solvate, and is characterized by the following peaks in an X-ray powder diffraction pattern: 5.7±0.2 degrees, 8.5±0.2 degrees, 9.5±0.2 degrees, 11.4±0.2 degrees, 15.3±0.2 degrees, 17.2±0.2 degrees, 18.9±0.2 degrees, and 22.2±0.2 degrees;

Form P is a MEK/water 90/10 solvate or a MEK/water 80/20 solvate, and is characterized by the following peaks in an X-ray powder diffraction pattern: 6.1±0.2 degrees, 7.4±0.2 degrees, 8.2±0.2 degrees, 9.1±0.2 degrees, 11.5±0.2 degrees, 12.3±0.2 degrees, 16.7±0.2 degrees, and 17.7±0.2 degrees;

Form Q is a MEK/water 80/20 solvate, and is characterized by the following peaks in an X-ray powder diffraction pattern: 6.3±0.2 degrees, 7.6±0.2 degrees, 8.4±0.2 degrees, 11.1±0.2 degrees, 12.5±0.2 degrees, 16.4±0.2 degrees, 16.9±0.2 degrees, and 18.0±0.2 degrees;

Form R is an acetonitrile solvate, and is characterized by the following peaks in an X-ray powder diffraction pattern: 6.7±0.2 degrees, 7.7±0.2 degrees, 13.2±0.2 degrees., 15.1±0.2 degrees, and 17.8±0.2 degrees;

Form S is a MEK/water 80/20 solvate, and is characterized by the following peaks in an X-ray powder diffraction pattern: 4.8±0.2 degrees, 7.7±0.2 degrees, 8.2±0.2 degrees, 9.6±0.2 degrees, 11.6±0.2 degrees, 15.1±0.2 degrees, 18.3±0.2 degrees, and 23.6±0.2 degrees;

Form T is an isopropyl acetate/water 95/5 solvate, and is characterized by the following peaks in an X-ray powder diffraction pattern: 4.9±0.2 degrees, 8.3±0.2 degrees, 9.8±0.2 degrees, 11.6±0.2 degrees, 18.1±0.2 degrees, 18.7±0.2 degrees, 21.1±0.2 degrees, and 24.0±0.2 degrees;

Form W is a solvated form from 10% water/90% acetonitrile, and is characterized by the following peaks in an X-ray powder diffraction pattern: 5.5±0.2 degrees, 10.9±0.2 degrees, 12.1±0.2 degrees, 13.3±0.2 degrees, 14.6±0.2 degrees, 17.2±0.2 degrees, 18.8±0.2 degrees, and 21.8±0.2 degrees; and Hydrate B is a hydrated form of Compound 1, and is characterized by the following peaks in an X-ray powder diffraction pattern: 4.9±0.2 degrees, 6.0±0.2 degrees, 7.2±0.2 degrees, 8.9±0.2 degrees, 10.1±0.2 degrees, 10.7±0.2 degrees, 11.3±0.2 degrees, and 11.9±0.2 degrees, and wherein the peaks are measured on a 2θ scale.

2. The crystalline solvate Form D of claim 1, characterized by the following peaks in an X-ray powder diffraction pattern: 5.6±0.2 degrees, 6.0±0.2 degrees, 7.8±0.2 degrees, 13.5±0.2 degrees, 14.1±0.2 degrees, 14.7±0.2 degrees, and 16.2±0.2 degrees on a 2θ scale in an X-ray powder diffraction pattern.

3. The crystalline solvate Form E of claim 1, characterized by the following peaks in an X-ray powder diffraction pattern: 8.0±0.2 degrees, 8.6±0.2 degrees, 10.1±0.2 degrees, 11.0±0.2 degrees, 11.9±0.2 degrees, 16.5±0.2 degrees, 17.1±0.2 degrees, and 18.1±0.2 degrees on a 2θ scale in an X-ray powder diffraction pattern.

4. The crystalline solvate Form F of claim 1, characterized by the following peaks in an X-ray powder diffraction pattern: 7.2±0.2 degrees, 7.8±0.2 degrees, 9.4±0.2 degrees, 10.7±0.2 degrees, 12.1±0.2 degrees, 12.8±0.2 degrees, 14.1±0.2 degrees, and 14.7±0.2 degrees on a 2θ scale in an X-ray powder diffraction pattern.

5. The crystalline solvate Form G of claim 1, characterized by the following peaks in an X-ray powder diffraction pattern: 6.3±0.2 degrees, 7.3±0.2 degrees, and 12.4±0.2 degrees on a 2θ scale in an X-ray powder diffraction pattern.

6. The crystalline solvate Form H of claim 1, characterized by the following peaks in an X-ray powder diffraction pattern: 7.9±0.2 degrees, 9.9±0.2 degrees, 10.4±0.2 degrees, 11.6±0.2 degrees, 12.1±0.2 degrees, 14.8±0.2 degrees, 16.0±0.2 degrees, and 17.9±0.2 degrees on a 2θ scale in an X-ray powder diffraction pattern.

7. The crystalline solvate Form I of claim 1, characterized by the following peaks in an X-ray powder diffraction pattern: 6.8±0.2 degrees, 8.4±0.2 degrees, 9.4±0.2 degrees, 10.2±0.2 degrees, 11.4±0.2 degrees, 17.1±0.2 degrees, 17.8±0.2 degrees, and 18.3±0.2 degrees on a 2θ scale in an X-ray powder diffraction pattern.

8. The crystalline solvate Form J of claim 1, characterized by the following peaks in an X-ray powder diffraction pattern: 6.0±0.2 degrees, 7.9±0.2 degrees, 8.8±0.2 degrees, 9.9±0.2 degrees, 11.8±0.2 degrees, 17.7±0.2 degrees, 18.0±0.2 degrees, and 18.5±0.2 degrees on a 2θ scale in an X-ray powder diffraction pattern.

9. The crystalline solvate Form K of claim 1, characterized by the following peaks in an X-ray powder diffraction pattern: 8.0±0.2 degrees, 8.5±0.2 degrees, 10.0±0.2 degrees, 11.8±0.2 degrees, 15.4±0.2 degrees, 15.9±0.2 degrees, 16.9±0.2 degrees, and 18.0±0.2 degrees on a 2θ scale in an X-ray powder diffraction pattern.

10. The crystalline solvate Form L of claim 1, characterized by the following peaks in an X-ray powder diffraction pattern: 7.9±0.2 degrees, 10.4±0.2 degrees, 10.9±0.2 degrees, 12.1±0.2 degrees, 14.8±0.2 degrees, 16.0±0.2 degrees, 18.6±0.2 degrees, and 20.5±0.2 degrees on a 2θ scale in an X-ray powder diffraction pattern.

11. The crystalline solvate Form M of claim 1, characterized by the following peaks in an X-ray powder diffraction pattern: 5.2±0.2 degrees, 6.0±0.2 degrees, 6.9±0.2 degrees, 10.7±0.2 degrees, 12.3±0.2 degrees, 17.6±0.2 degrees, 18.3±0.2 degrees, and 21.1±0.2 degrees on a 2θ scale in an X-ray powder diffraction pattern.

12. The crystalline solvate Form N of claim 1, characterized by the following peaks in an X-ray powder diffraction pattern: 8.2±0.2 degrees, 9.7±0.2 degrees, 10.6±0.2 degrees, 11.5±0.2 degrees, 12.4±0.2 degrees, 16.6±0.2 degrees, 17.6±0.2 degrees, and 23.8±0.2 degrees on a 2θ scale in an X-ray powder diffraction pattern.

13. The crystalline solvate Form O of claim 1, characterized by the following peaks in an X-ray powder diffraction pattern: 5.7±0.2 degrees, 8.5±0.2 degrees, 9.5±0.2 degrees, 11.4±0.2 degrees, 15.3±0.2 degrees, 17.2±0.2 degrees, 18.9±0.2 degrees, and 22.2±0.2 degrees on a 2θ scale in an X-ray powder diffraction pattern.

14. The crystalline solvate Form P of claim 1, characterized by the following peaks in an X-ray powder diffraction pattern: 6.1±0.2 degrees, 7.4±0.2 degrees, 8.2±0.2 degrees, 9.1±0.2 degrees, 11.5±0.2 degrees, 12.3±0.2 degrees, 16.7±0.2 degrees, and 17.7±0.2 degrees on a 2θ scale in an X-ray powder diffraction pattern.

15. The crystalline solvate Form Q of claim 1, characterized by the following peaks in an X-ray powder diffraction pattern: 6.3±0.2 degrees, 7.6±0.2 degrees, 8.4±0.2 degrees, 11.1±0.2 degrees, 12.5±0.2 degrees, 16.4±0.2 degrees, 16.9±0.2 degrees, and 18.0±0.2 degrees on a 2θ scale in an X-ray powder diffraction pattern.

16. The crystalline solvate Form R of claim 1, characterized by the following peaks in an X-ray powder diffraction pattern: 6.7±0.2 degrees, 7.7±0.2 degrees, 13.2±0.2 degrees, 15.1±0.2 degrees, and 17.8±0.2 degrees on a 2θ scale in an X-ray powder diffraction pattern.

17. The crystalline solvate Form S of claim 1, characterized by the following peaks in an X-ray powder diffraction pattern: 4.8±0.2 degrees, 7.7±0.2 degrees, 8.2±0.2 degrees, 9.6±0.2 degrees, 11.6±0.2 degrees, 15.1±0.2 degrees, 18.3±0.2 degrees, and 23.6±0.2 degrees on a 2θ scale in an X-ray powder diffraction pattern.

18. The crystalline solvate Form T of claim 1, characterized by the following peaks in an X-ray powder diffraction pattern: 4.9±0.2 degrees, 8.3±0.2 degrees, 9.8±0.2 degrees, 11.6±0.2 degrees, 18.1±0.2 degrees, 18.7±0.2 degrees, 21.1±0.2 degrees, and 24.0±0.2 degrees on a 2θ scale in an X-ray powder diffraction pattern.

19. The crystalline Hydrate B of claim 1, characterized by the following peaks in an X-ray powder diffraction pattern: 4.9±0.2 degrees, 6.0±0.2 degrees, 7.2±0.2 degrees, 8.9±0.2 degrees, 10.1±0.2 degrees, 10.7±0.2 degrees, 11.3±0.2 degrees, and 11.9±0.2 degrees on a 2θ scale in an X-ray powder diffraction pattern.

20. The crystalline solvate Form W of claim 1, characterized by the following peaks in an X-ray powder diffraction pattern: 5.5±0.2 degrees, 10.9±0.2 degrees, 12.1±0.2 degrees, 13.3±0.2 degrees, 14.6±0.2 degrees, 17.2±0.2 degrees, 18.8±0.2 degrees, and 21.8±0.2 degrees on a 2θ scale in an X-ray powder diffraction pattern.

21. A pharmaceutical composition comprising a crystalline solvate of claim 1 of Form D, E, F, G, H, I, J, K, L, M, N, O, P, Q, R, S, T, W, or Hydrate B, or combinations thereof, and a pharmaceutical carrier or excipient.

22. The pharmaceutical composition according to claim 21, further comprising an additional agent selected from a mucolytic agent, a bronchodilator, an antibiotic, an anti-infective agent, an anti-inflammatory agent, a CFTR modulator other than a crystalline solvate Form D, E, F, G, H, I, J, K, L, M, N, O, P, Q, R, S, T, W, or Hydrate B, or combinations thereof.

23. The pharmaceutical composition according to claim 22, wherein said additional agent is a CFTR modulator other than crystalline solvate Form D, E, F, G, H, I, J, K, L, M, N, O, P, Q, R, S, T, W, or Hydrate B, or combinations thereof.

24. A method of treating or lessening the severity of a disease in a patient, wherein said disease is selected from cystic fibrosis, smoke induced COPD, pancreatitis, pancreatic insufficiency, hereditary emphysema, COPD, and dry-eye disease, said method comprising the step of administering to said patient an effective amount of a crystalline solvate of claim 1 of Form D, E, F, G, H, I, J, K, L, M, N, O, P, Q, R, S, T, W, or Hydrate B, or combinations thereof.

25. The method according to claim 24, wherein said disease is cystic fibrosis, hereditary emphysema, COPD, or dry-eye disease.

26. The method according to claim 25, wherein said disease is cystic fibrosis, hereditary emphysema, or dry-eye disease.

27. The method according to claim 26, wherein said disease is cystic fibrosis.

28. A crystalline hydrate of N-[2,4-bis(1,1-dimethylethyl)-5-hydroxyphenyl]-1,4-dihydro-4-oxoquinoline-3-carboxamide (Compound 1), wherein the crystalline solvate is designated as Hydrate B, and is characterized by the following peaks in an X-ray powder diffraction pattern: 4.9±0.2 degrees, 6.0±0.2 degrees, 7.2±0.2 degrees, 8.9±0.2 degrees, 10.1±0.2 degrees, 10.7±0.2 degrees, 11.3±0.2 degrees, and 11.9±0.2 degrees, and wherein the peaks are measured on a 2θ scale.

* * * * *